(12) United States Patent
Leimbach et al.

(10) Patent No.: US 10,314,563 B2
(45) Date of Patent: Jun. 11, 2019

(54) GRAPHICAL USER INTERFACE FOR BIOPSY DEVICE

(71) Applicant: Devicor Medical Products, Inc., Cincinnati, OH (US)

(72) Inventors: Jessica P. Leimbach, Cincinnati, OH (US); Kathryn M. Dodd, Cincinnati, OH (US); Melody L. Mitro, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 415 days.

(21) Appl. No.: 14/951,549

(22) Filed: Nov. 25, 2015

(65) Prior Publication Data

US 2016/0166331 A1 Jun. 16, 2016

Related U.S. Application Data

(60) Provisional application No. 62/084,634, filed on Nov. 26, 2014.

(51) Int. Cl.
*A61B 5/00* (2006.01)
*A61B 10/02* (2006.01)
(Continued)

(52) U.S. Cl.
CPC ...... *A61B 10/0266* (2013.01); *A61B 10/0275* (2013.01); *A61B 34/25* (2016.02);
(Continued)

(58) Field of Classification Search
CPC .......................... A61B 10/02; A61B 10/0233; A61B 10/0266; A61B 10/0275; A61B 10/0096; A61B 2010/0225; A61B 19/56
See application file for complete search history.

(56) References Cited

U.S. PATENT DOCUMENTS 3,844,272 A 10/1974 Banko
4,517,976 A 5/1985 Murakoshi et al.
(Continued)

FOREIGN PATENT DOCUMENTS

DE 3703218 A1 8/1988
EP 0 225 973 A2 6/1987
(Continued)

OTHER PUBLICATIONS

International Search Report and Written Opinion dated Mar. 15, 2016 for Application No. PCT/US2015/062580, 13 pgs.
(Continued)

*Primary Examiner* — Max F Hindenburg
(74) *Attorney, Agent, or Firm* — Frost Brown Todd LLC

(57) ABSTRACT

A biopsy system, including a probe set, a holster, and a user interface. The probe set includes a plurality of probes. Each probe of the probe set includes a probe body, a needle, a cutter, and a tissue sample holder. The tissue sample holder is in communication with the cutter to receive one or more tissue samples. The holster is selectively securable to each probe of the probe set. The user interface is in communication with the holster. The user interface includes a display. The user interface is configured to identify which probe of the probe set is secured to the holster when a selected probe of the probe set is secured to the holster.

15 Claims, 42 Drawing Sheets

(51) Int. Cl.
  *A61B 34/00* (2016.01)
  *A61B 10/00* (2006.01)
  *A61B 17/00* (2006.01)
(52) U.S. Cl.
  CPC ... *A61B 10/0096* (2013.01); *A61B 2010/0225* (2013.01); *A61B 2017/00199* (2013.01)

(56) References Cited

U.S. PATENT DOCUMENTS

| | | |
|---|---|---|
| 4,739,759 A | 4/1988 | Rexroth et al. |
| 4,769,850 A | 9/1988 | Itoh et al. |
| 4,878,493 A | 11/1989 | Pasternak et al. |
| 5,159,929 A | 11/1992 | Morris et al. |
| 5,335,671 A | 8/1994 | Clement |
| 5,400,267 A | 3/1995 | Denen et al. |
| 5,415,169 A | 5/1995 | Siczek et al. |
| 5,526,822 A | 6/1996 | Burbank et al. |
| 5,549,112 A | 8/1996 | Cockburn et al. |
| 5,609,152 A | 3/1997 | Pellegrino et al. |
| 5,617,857 A | 4/1997 | Chader et al. |
| 5,640,956 A | 6/1997 | Getzinger et al. |
| 5,643,255 A | 7/1997 | Organ |
| 5,658,819 A | 8/1997 | Humphrey et al. |
| 5,728,124 A | 3/1998 | Cockburn et al. |
| 5,749,869 A | 5/1998 | Lindenmeier et al. |
| 5,769,086 A | 6/1998 | Ritchart et al. |
| 5,772,659 A | 6/1998 | Becker et al. |
| 5,807,304 A | 9/1998 | Cockburn |
| 5,829,439 A | 11/1998 | Yokosawa et al. |
| 5,848,177 A | 12/1998 | Bauer et al. |
| 5,849,009 A | 12/1998 | Bernaz |
| 5,928,164 A | 7/1999 | Burbank et al. |
| 5,976,128 A | 11/1999 | Schilling et al. |
| 5,997,535 A | 12/1999 | Betsill et al. |
| 6,017,316 A | 1/2000 | Ritchart et al. |
| 6,022,325 A | 2/2000 | Siczek et al. |
| 6,022,347 A | 2/2000 | Lindemeier et al. |
| 6,036,681 A | 3/2000 | Hooven |
| 6,086,544 A | 4/2000 | Hibner et al. |
| 6,066,134 A | 5/2000 | Eggers et al. |
| 6,066,296 A | 5/2000 | Brady et al. |
| 6,117,126 A | 9/2000 | Appelbaum et al. |
| 6,162,187 A | 12/2000 | Buzzard et al. |
| 6,162,216 A | 12/2000 | Guziak et al. |
| 6,182,069 B1 | 1/2001 | Niblack |
| 6,216,029 B1 | 4/2001 | Paltieli |
| 6,217,510 B1 | 4/2001 | Ozawa et al. |
| 6,228,055 B1 | 5/2001 | Foerster et al. |
| 6,238,342 B1 | 5/2001 | Feleppa et al. |
| 6,246,782 B1 | 6/2001 | Shapiro et al. |
| 6,351,660 B1 | 2/2002 | Burke et al. |
| 6,370,411 B1 | 4/2002 | Osadchy et al. |
| 6,371,904 B1 | 4/2002 | Sirimanne et al. |
| 6,391,024 B1 | 5/2002 | Sun et al. |
| 6,432,065 B1 | 8/2002 | Burdorff et al. |
| 6,436,054 B1 | 8/2002 | Viola et al. |
| 6,458,121 B1 | 10/2002 | Rosenstock et al. |
| 6,585,664 B2 | 7/2003 | Burdorff et al. |
| 6,626,849 B2 | 9/2003 | Huitema et al. |
| 6,632,183 B2 | 10/2003 | Bowman et al. |
| 6,752,768 B2 | 6/2004 | Burdorff et al. |
| 6,783,523 B2 | 8/2004 | Qin et al. |
| 6,960,209 B2 | 11/2005 | Clague et al. |
| 6,981,941 B2 | 1/2006 | Whitman et al. |
| 6,993,175 B2 | 1/2006 | Samoszuk et al. |
| 6,993,375 B2 | 1/2006 | Burbank et al. |
| 6,996,433 B2 | 2/2006 | Burbank et al. |
| 7,044,957 B2 | 5/2006 | Foerster et al. |
| 7,047,063 B2 | 5/2006 | Burbank et al. |
| 7,060,063 B2 | 6/2006 | Marion et al. |
| 7,061,242 B2 | 6/2006 | Ochi et al. |
| 7,092,557 B2 | 8/2006 | Eisfeld et al. |
| 7,153,274 B2 | 12/2006 | Stephens et al. |
| 7,169,155 B2 | 1/2007 | Chu et al. |
| 7,184,582 B2 | 2/2007 | Giger et al. |
| 7,204,826 B2 | 4/2007 | Tremaglio, Jr. et al. |
| 7,229,417 B2 | 6/2007 | Foerster et al. |
| 7,257,244 B2 | 8/2007 | Miga |
| 7,274,810 B2 | 9/2007 | Reeves et al. |
| 7,344,533 B2 | 3/2008 | Pearson et al. |
| 7,347,829 B2 | 3/2008 | Mark et al. |
| 7,377,902 B2 | 5/2008 | Burbank et al. |
| 7,418,119 B2 | 8/2008 | Leichter et al. |
| 7,442,171 B2 | 10/2008 | Stephens et al. |
| 7,449,022 B2 | 11/2008 | Quick et al. |
| 7,465,090 B2 | 12/2008 | Haras |
| 7,465,279 B2 | 12/2008 | Beckman et al. |
| 7,474,407 B2 | 1/2009 | Gutin |
| 7,496,398 B2 | 2/2009 | Nields et al. |
| 7,517,322 B2 | 4/2009 | Weikel, Jr. et al. |
| 7,542,791 B2 | 6/2009 | Mire et al. |
| 7,598,088 B2 | 10/2009 | Balas |
| 7,648,466 B2 | 1/2010 | Stephens et al. |
| 7,660,623 B2 | 2/2010 | Hunter et al. |
| 7,693,567 B2 | 4/2010 | Tsonton et al. |
| 7,837,632 B2 | 11/2010 | Stephens et al. |
| 7,844,474 B2 | 11/2010 | Barth et al. |
| 7,854,706 B2 | 12/2010 | Hibner |
| 7,914,464 B2 | 3/2011 | Burdorff et al. |
| 7,918,803 B2 | 4/2011 | Ritchart et al. |
| 7,918,804 B2 | 4/2011 | Monson et al. |
| 7,938,786 B2 | 5/2011 | Ritchie et al. |
| 8,005,529 B2 | 8/2011 | Ramzipoor et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,371,443 B2 | 2/2013 | Nock et al. |
| 8,388,540 B2 | 3/2013 | Willis |
| 8,454,531 B2 | 6/2013 | Speeg et al. |
| 8,532,747 B2 | 9/2013 | Nock et al. |
| 8,532,748 B2 | 9/2013 | Leimbach et al. |
| 8,600,125 B2 | 12/2013 | Kaufman et al. |
| 8,622,907 B2 | 1/2014 | Malchow et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,271,797 B2* | 3/2016 | Adler .............. A61B 34/37 |
| 9,364,279 B2* | 6/2016 | Houser ........... A61B 17/00234 |
| 2003/0139700 A1 | 7/2003 | Elliott et al. |
| 2003/0181898 A1 | 9/2003 | Bowers |
| 2004/0153005 A1 | 8/2004 | Krueger |
| 2004/0181219 A1 | 9/2004 | Goble et al. |
| 2004/0202357 A1 | 10/2004 | Perz et al. |
| 2004/0267121 A1 | 12/2004 | Sarvazyan et al. |
| 2005/0004579 A1 | 1/2005 | Schneider et al. |
| 2005/0119646 A1 | 6/2005 | Scholl et al. |
| 2005/0159676 A1 | 7/2005 | Taylor et al. |
| 2006/0074345 A1 | 4/2006 | Hibner |
| 2008/0187095 A1 | 8/2008 | Boone et al. |
| 2008/0214955 A1 | 9/2008 | Speeg et al. |
| 2008/0221478 A1 | 9/2008 | Ritchie et al. |
| 2009/0131821 A1 | 5/2009 | Speeg et al. |
| 2009/0209854 A1 | 8/2009 | Parihar et al. |
| 2009/0216151 A1 | 8/2009 | Speeg et al. |
| 2010/0152610 A1 | 6/2010 | Parihar et al. |
| 2010/0160819 A1 | 6/2010 | Parihar et al. |
| 2011/0071391 A1 | 3/2011 | Speeg |
| 2011/0071423 A1 | 3/2011 | Speeg et al. |
| 2011/0152715 A1 | 6/2011 | Delap et al. |
| 2012/0283563 A1 | 11/2012 | Moore et al. |
| 2013/0053724 A1 | 2/2013 | Fiebig et al. |
| 2013/0150751 A1 | 6/2013 | Fiebig et al. |
| 2013/0218047 A1 | 8/2013 | Fiebig et al. |
| 2013/0324882 A1 | 12/2013 | Mescher |
| 2014/0039343 A1 | 2/2014 | Mescher et al. |
| 2014/0330113 A1 | 11/2014 | Daw et al. |
| 2015/0065913 A1 | 3/2015 | Keller et al. |

(56) References Cited

U.S. PATENT DOCUMENTS

FOREIGN PATENT DOCUMENTS

| EP | 1 051 948 A2 | 11/2000 |
|---|---|---|
| EP | 1 053 720 A1 | 11/2000 |
| EP | 1 082 945 A1 | 3/2001 |
| EP | 1 157 667 A2 | 11/2001 |
| EP | 1 519 472 A1 | 3/2005 |
| EP | 1 527 743 A2 | 5/2005 |
| EP | 1 816 966 A1 | 8/2007 |
| EP | 2 062 535 | 5/2009 |
| GB | 2146534 A | 4/1985 |
| JP | 2002-320325 A | 10/2002 |
| WO | WO 1993/15655 A1 | 8/1993 |
| WO | WO 1996/39088 A1 | 12/1996 |
| WO | WO 1998/07378 A1 | 2/1998 |
| WO | WO 1998/14129 A1 | 4/1998 |
| WO | WO 2002/24082 A2 | 3/2002 |
| WO | WO 2003/077778 A1 | 9/2003 |
| WO | WO 2004/019799 A2 | 3/2004 |
| WO | WO 2004/110294 A1 | 12/2004 |
| WO | WO 2005/060849 A1 | 7/2005 |
| WO | WO 2006/058302 A1 | 6/2006 |
| WO | WO 2013/158072 A1 | 10/2013 |
| WO | WO 2013/0181005 | 12/2013 |

OTHER PUBLICATIONS

U.S. Appl. No. 62/054,523, filed Sep. 24, 2014.
International Search Report and Written Opinion dated Apr. 5, 2006 for Application No. PCT/US2005/042966, 7 pgs.
Force FX™ Electrosurgical Generator with Instant Response Technology, Nov. 2011, accessed from: http://www.medtronic.com/content/dam/covidien/library/global/english/product/electrosurgical-hardware/generators-and-monitors/force-fx-electrosurgical-generator-c-with-instant-response-technology/force-fx-generator-brochure.pdf, pp. 1-8.
Force EZ™ Electrosurgical Generator with Instant Response Technology, Oct. 2002, accessed from http://www.medtronic.com/content/dam/covidien/library/global/en/product/electrosurgical-hardware/force-ez-generator-technical-specifications.pdf, pp. 1-4.
Amplifiemodule 1-30MHz 150Watts, LCF Enterprises RF Power Amplifiers, 1997, accessed from: www.lcfamps.com, 1 pg.
Extended European Search Report dated Jun. 6, 2018 for Application No. 15863319.8, 7 pages.

* cited by examiner

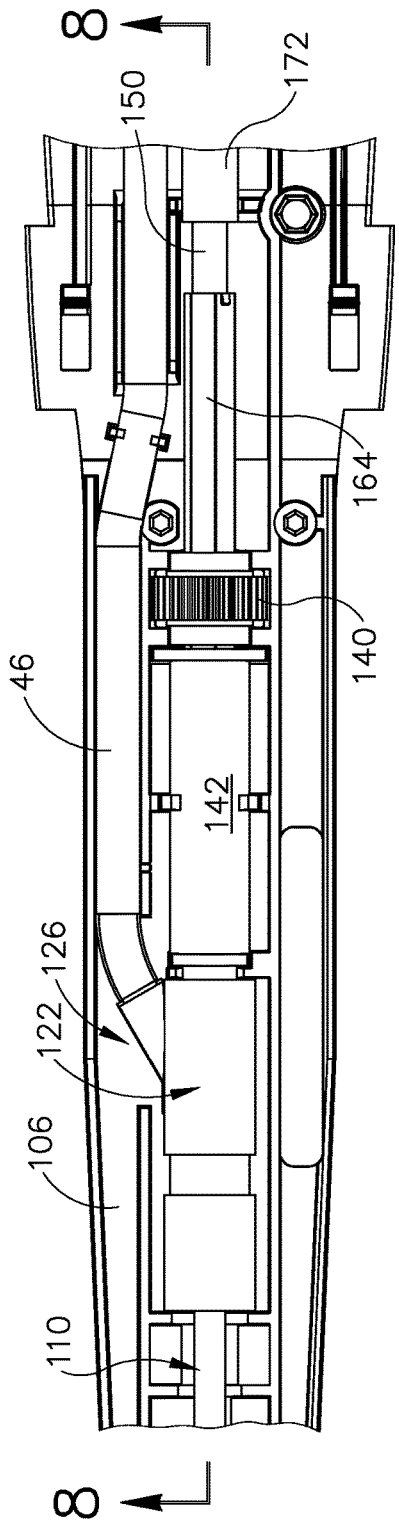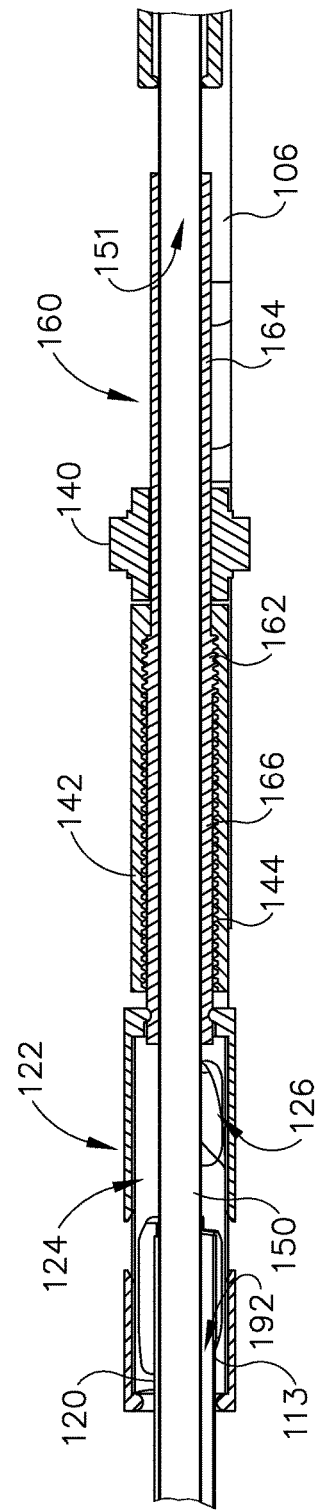

GRAPHICAL USER INTERFACE FOR BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. Patents is incorporated by reference herein.

Additional exemplary biopsy devices and biopsy system components are disclosed in U.S. Pub. No. 2006/0074345, entitled "Biopsy Apparatus and Method," published Apr. 6, 2006; U.S. Pub. No. 2008/0146962, entitled "Biopsy System with Vacuum Control Module," published Jun. 19, 2008; U.S. Pub. No. 2008/0214955, entitled "Presentation of Biopsy Sample by Biopsy Device," published Sep. 4, 2008; U.S. Pub. No. 2008/0221480, entitled "Biopsy Sample Storage," published Sep. 11, 2008; U.S. Pub. No. 2009/0131821, entitled "Graphical User Interface For Biopsy System Control Module," published May 21, 2009; U.S. Pub. No. 2009/0131820, entitled "Icon-Based User Interface on Biopsy System Control Module," published May 21, 2009; U.S. Pub. No. 2009/0216152, entitled "Needle Tip for Biopsy Device," published Aug. 27, 2009; U.S. Pub. No. 2010/0113973, entitled "Biopsy Device with Rotatable Tissue Sample Holder," published May 6, 2010; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0160824, entitled "Biopsy Device with Discrete Tissue Chambers," published Jun. 24, 2010; U.S. Pub. No. 2010/0317997, entitled "Tetherless Biopsy Device with Reusable Portion," published Dec. 16, 2010; U.S. Pub. No. 2012/0109007, entitled "Handheld Biopsy Device with Needle Firing," published May 3, 2012; U.S. Pub. No. 2012/0265095, entitled "Biopsy Device with Motorized Needle Firing," published Oct. 18, 2012; U.S. Pub. No. 2012/0283563, entitled "Biopsy Device with Manifold Alignment Feature and Tissue Sensor," published Nov. 8, 2012; U.S. Pub. No. 2012/0310110, entitled "Needle Assembly and Blade Assembly for Biopsy Device," published Dec. 6, 2012; U.S. Pub. No. 2013/0041256, entitled "Access Chamber and Markers for Biopsy Device," published Feb. 14, 2013; U.S. Pub. No. 2013/0053724, entitled "Biopsy Device Tissue Sample Holder with Bulk Chamber and Pathology Chamber," published Feb. 28, 2013; U.S. Pub. No. 2013/0150751, entitled "Biopsy Device with Slide-In Probe," published Jun. 13, 2013; U.S. Pub. No. 2013/0324882, entitled "Control for Biopsy Device," published Dec. 5, 2013; U.S. Pub. No. 2013/0218047, entitled "Biopsy Device Valve Assembly," published Aug. 22, 2013; and U.S. Pub. No. 2014/0039343, entitled "Biopsy System," published Feb. 6, 2014. The disclosure of each of the above-cited U.S. Patent Application Publications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMO-MARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun.

12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. Patents and U.S. Patent Application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts a partial top plan view of components of the probe of FIG. 4, with a top housing piece removed;

FIG. 8 depicts a side cross-sectional view of the components of FIG. 7, taken along line 8-8 of FIG. 7;

Figure 1:
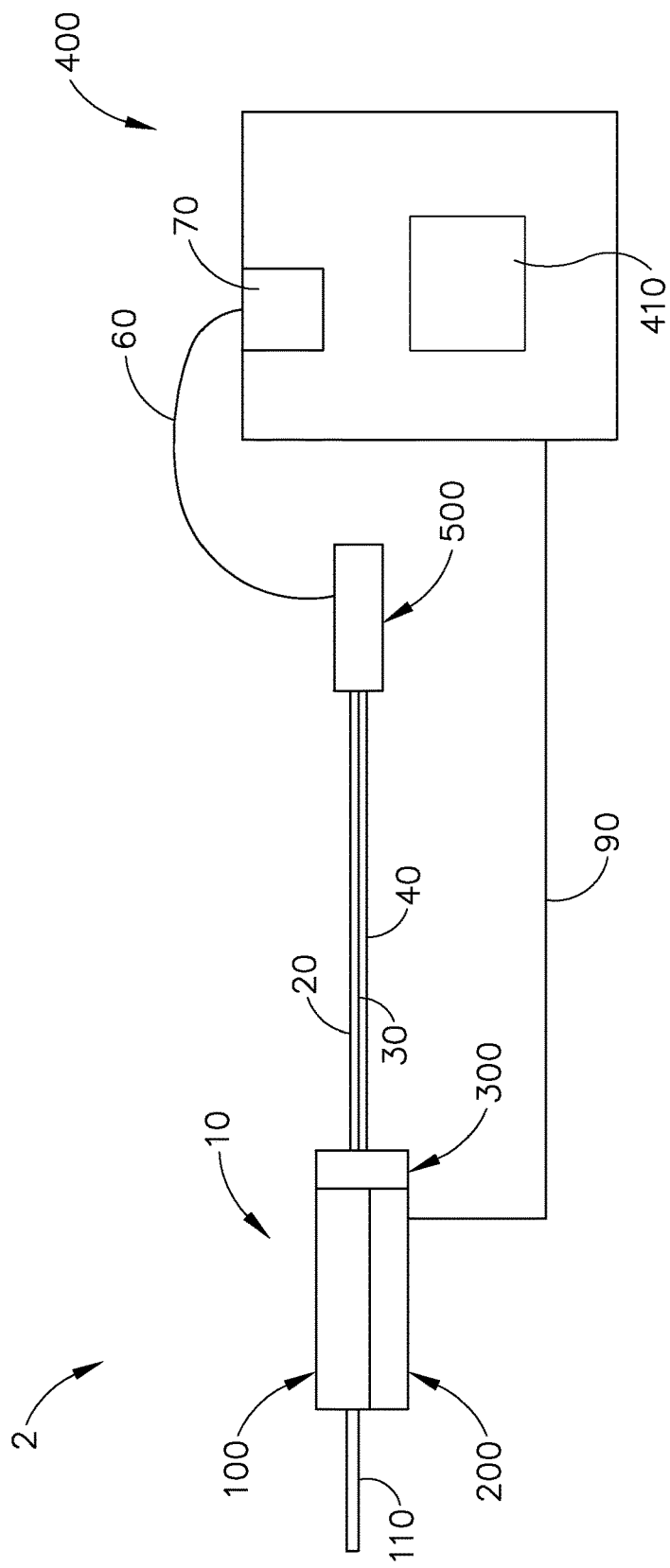
FIG. 1 depicts a schematic view of an exemplary biopsy system including a biopsy device and a vacuum control module.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

Figure 2:
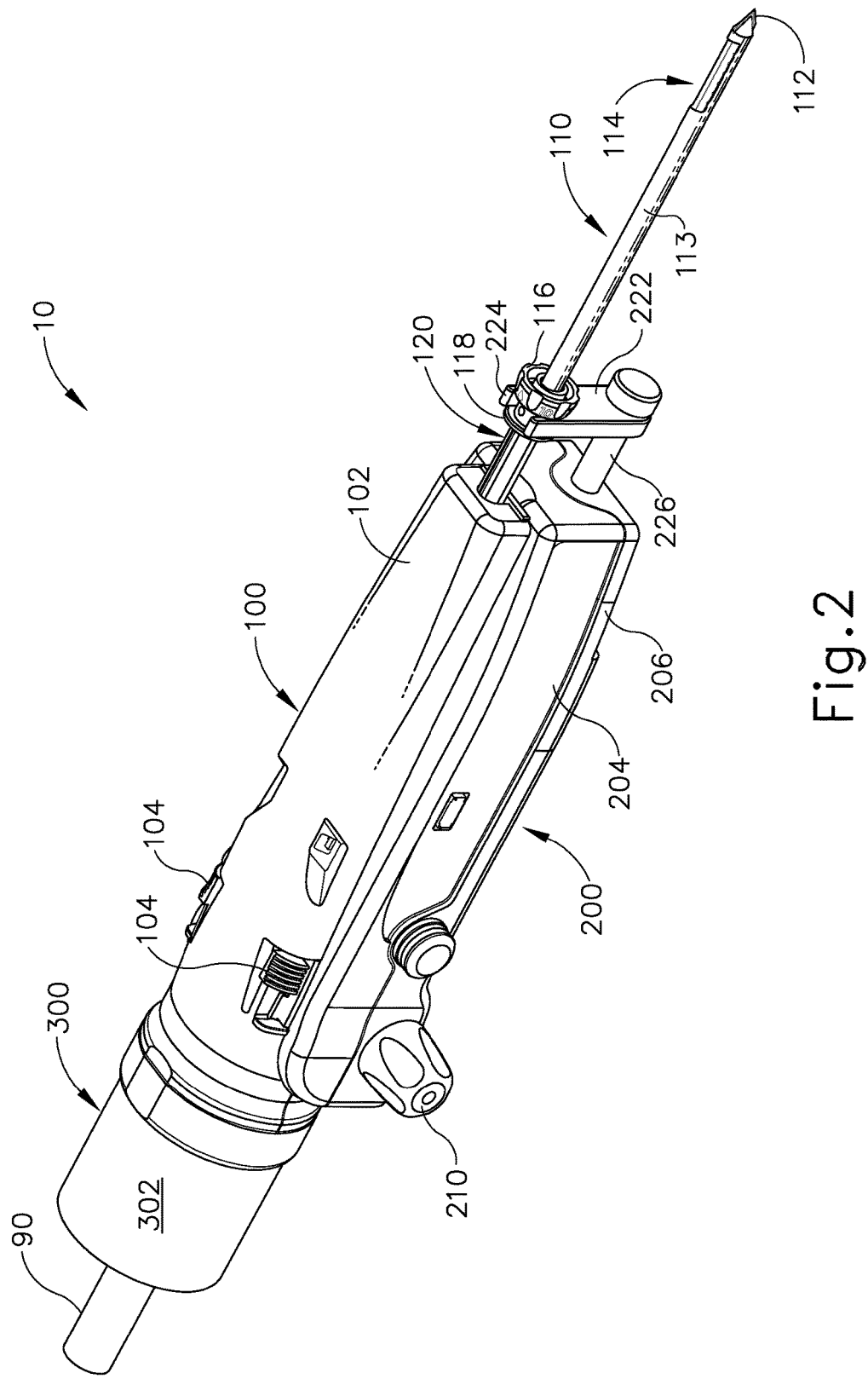
FIG. 2 depicts a perspective view of an exemplary biopsy device of the biopsy system of FIG. 1, including an exemplary probe coupled with an exemplary holster.
Figure 3:
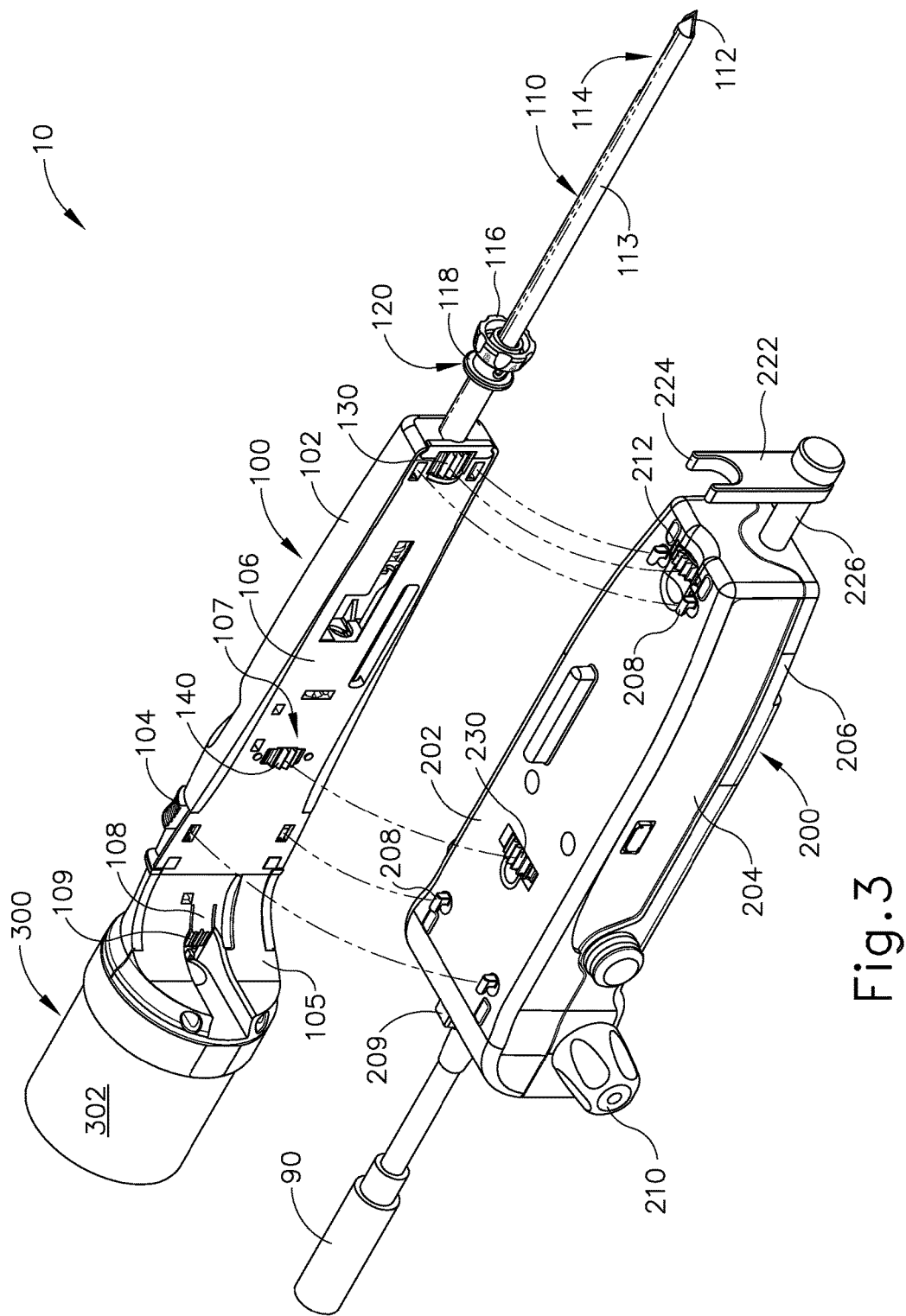
FIG. 3 depicts a perspective view of the biopsy device of FIG. 2, with the probe decoupled from the holster.

FIG. 1 depicts an exemplary biopsy system (2) comprising a biopsy device (10) and a vacuum control module (400). Biopsy device (10) of this example comprises a probe (100) and a holster (200), as shown in FIGS. 2-3. A needle (110) extends distally from probe (100), and is inserted into a patient's tissue to obtain tissue samples. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Holster

As shown in FIG. 3, holster (200) of the present example includes a top housing cover (202), side panels (204), and a housing base (206), which are fixedly secured together. Gears (212, 230) are exposed through top housing cover (202), and mesh with gears (130, 140) of probe (100) when probe (100) and holster (200) are coupled together. In particular, gears (230, 140) drive the actuation assembly of a cutter (150) within needle (110); while gears (212, 130) are employed to rotate needle (110). Gear (240) is located at the proximal end of holster (200) and meshes with gear (182) of probe (100) to rotate a manifold (310) of tissue sample holder (300).

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebeteween. Prongs (224) are positioned between annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224). Other suitable components, configurations, and relationships will be apparent to those of ordinary skill in the art in view of the teachings herein. The internal components of the needle firing mechanism of the present example are configured and arranged as described in U.S. Pat. No. 8,858,465, entitled "Biopsy Device with Motorized Needle Firing," issued Oct. 14, 2014, the disclosure of which is incorporated by reference herein.

Holster (200) includes motors (not shown) to drive gears (230, 240) to thereby rotate and translate cutter (150) and rotate manifold (310) of tissue sample holder (300). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). As will be described in greater detail below, such data may be used by control module (400) to display certain graphical user interface screens on a touchscreen (410) integrated into control module (400). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200). As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

III. Exemplary Probe

Probe (100) of the present example includes a needle (110) extending distally from probe (100) that is inserted into a patient's tissue to obtain tissue samples. These tissue samples are deposited in a tissue sample holder (300) at the proximal end of probe (100). As shown in FIG. 1, vacuum control module (400) is coupled with probe (100) via a valve assembly (500) and tubes (20, 30, 40, 60), which is operable to selectively provide vacuum, saline, atmospheric air, and venting to probe (100). The internal components of the valve assembly of the present example are configured and arranged as described in U.S. Pub. No. 2013/0218047, entitled "Biopsy Device Valve Assembly," published Aug. 22, 2013, the disclosure of which is incorporated by reference herein.

As shown in FIGS. 1-6, probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together.

A. Exemplary Needle Assembly

Needle (110) of the present example comprises a cannula (113) having a tissue piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," issued Aug. 12, 2014, the disclosure of which is incorporated by reference herein. As another merely illustrative example, tip (112) may be configured in accordance with at least some of the teachings in U.S. Pub. No. 2013/0150751, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
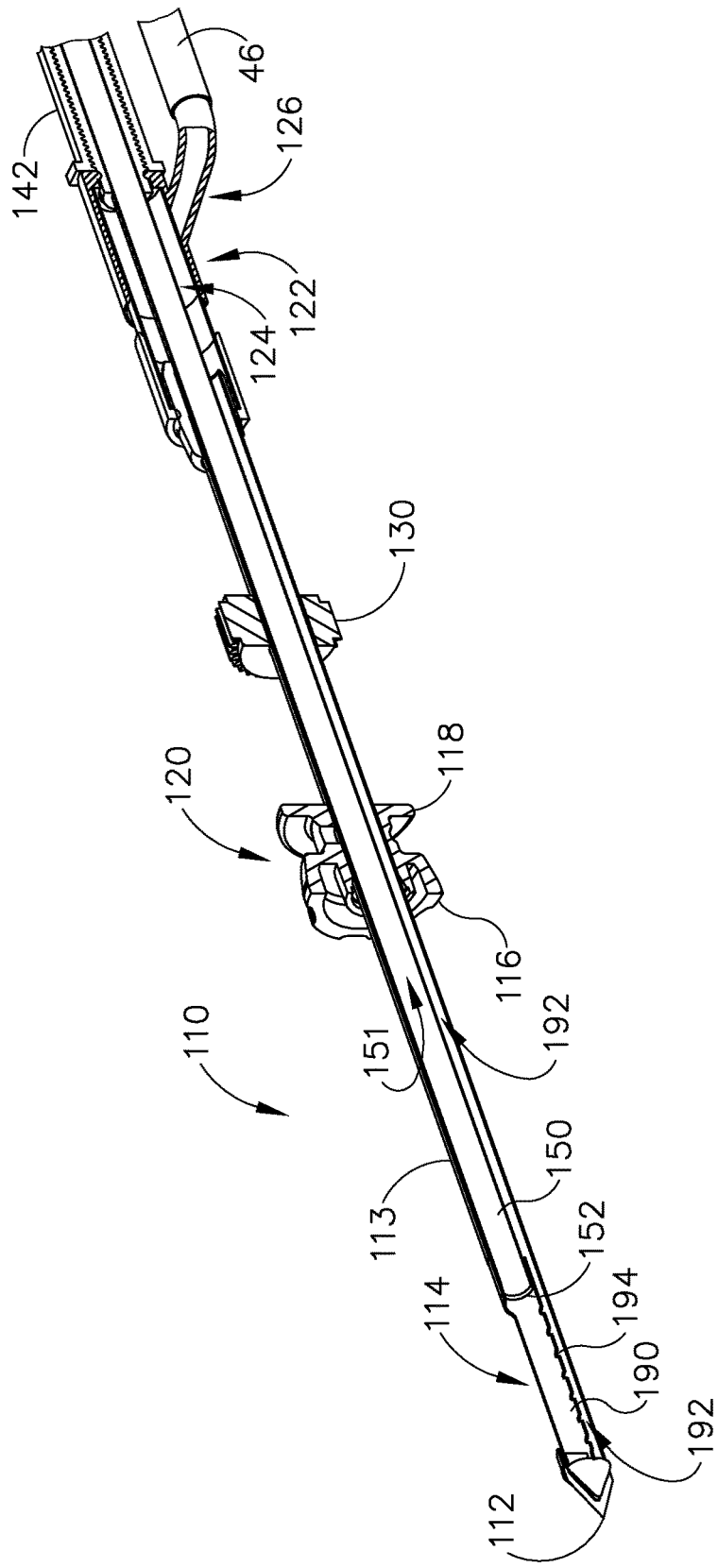
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212). Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively.

Figure 4:
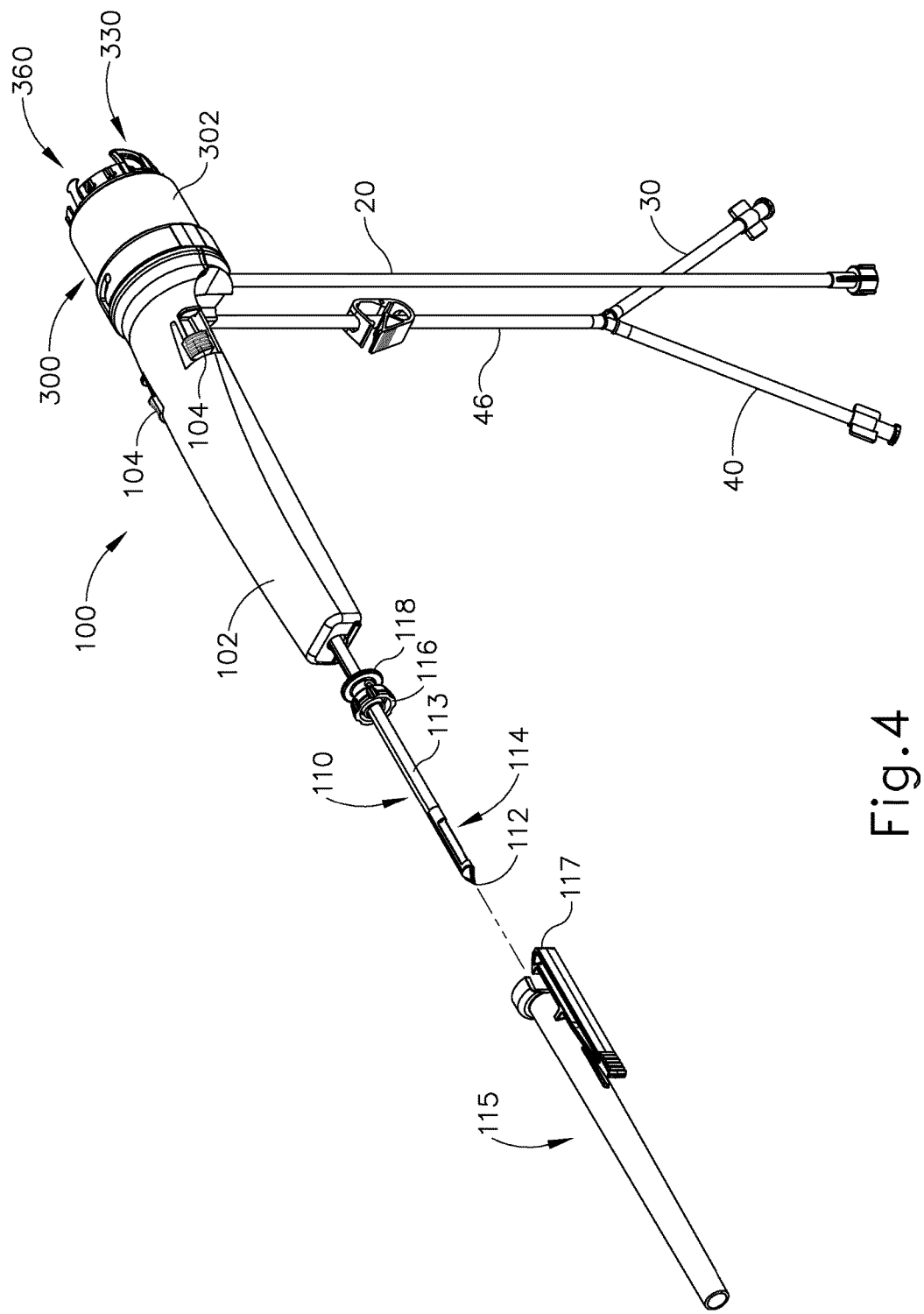
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Pub. No. 2013/0150751, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
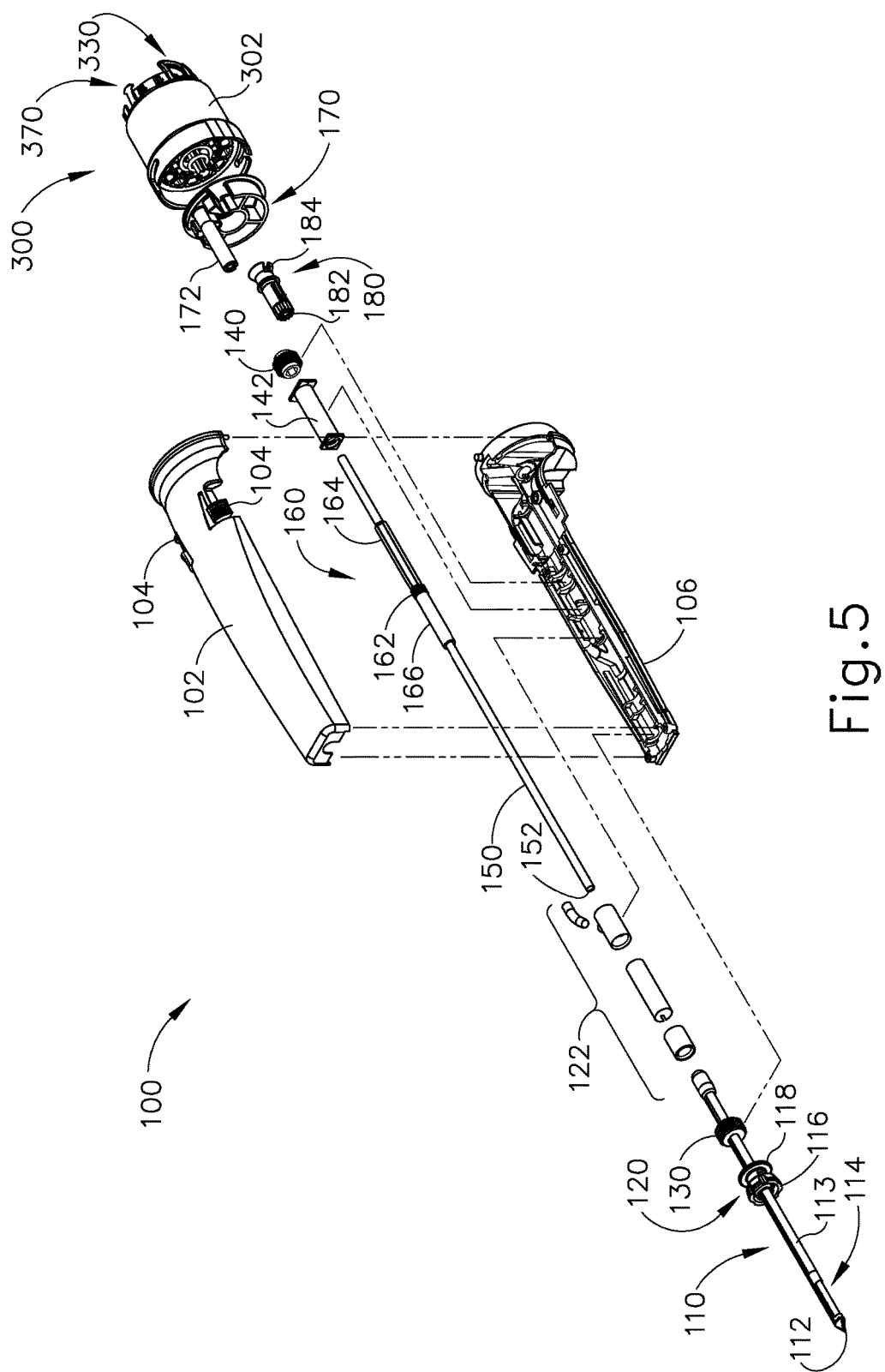
FIG. 5 depicts an exploded view of the probe of FIG. 4.

As noted above, cutter (150) is operable to simultaneously translate and rotate relative to needle (110) to sever a tissue sample from tissue protruding through lateral aperture (114). As best seen in FIGS. 5-7 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

A gear (140) is positioned on flats (164) and includes a set of internal flats (not shown) that complement flats (164). Thus, gear (140) rotates overmold (160) and cutter (150)

when gear (140) is rotated. However, overmold (160) is slidable relative to gear (140), such that cutter (150) may translate relative to chassis (160) despite gear (140) being longitudinally fixed relative to chassis (160). Gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a manifold (310). Manifold (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate manifold (310) to index tissue chambers relative to lumen (151) of cutter (150) as will be described in greater detail below. A transparent cover (302) is positioned about manifold (310) and is removably secured to chassis (106). While bayonet features provide coupling between cover (302) and chassis (106), it should be understood that any suitable type of coupling may be used. Manifold (310) is freely rotatable within cover (302). However, manifold (310) is engaged with cover (302) such that manifold (310) will decouple relative to chassis (106) when cover (302) is removed from chassis (106). In other words, manifold (310) may be selectively coupled with and removed relative to chassis (106) by coupling and removing cover (302) from chassis (106).

1. Exemplary Manifold

Figure 12:
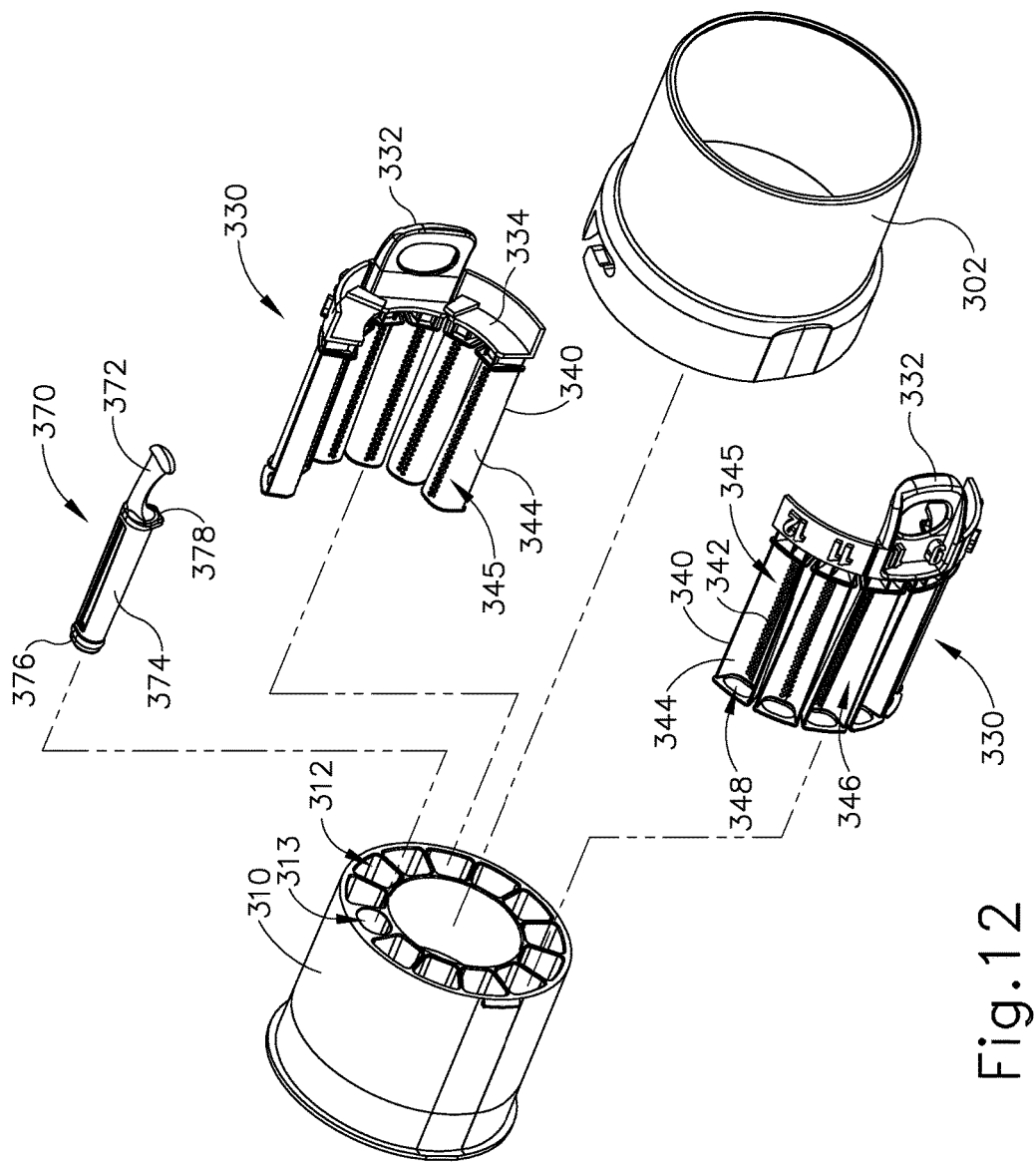
FIG. 12 depicts an exploded view of the tissue sample holder assembly of FIG. 9.
Figure 13:
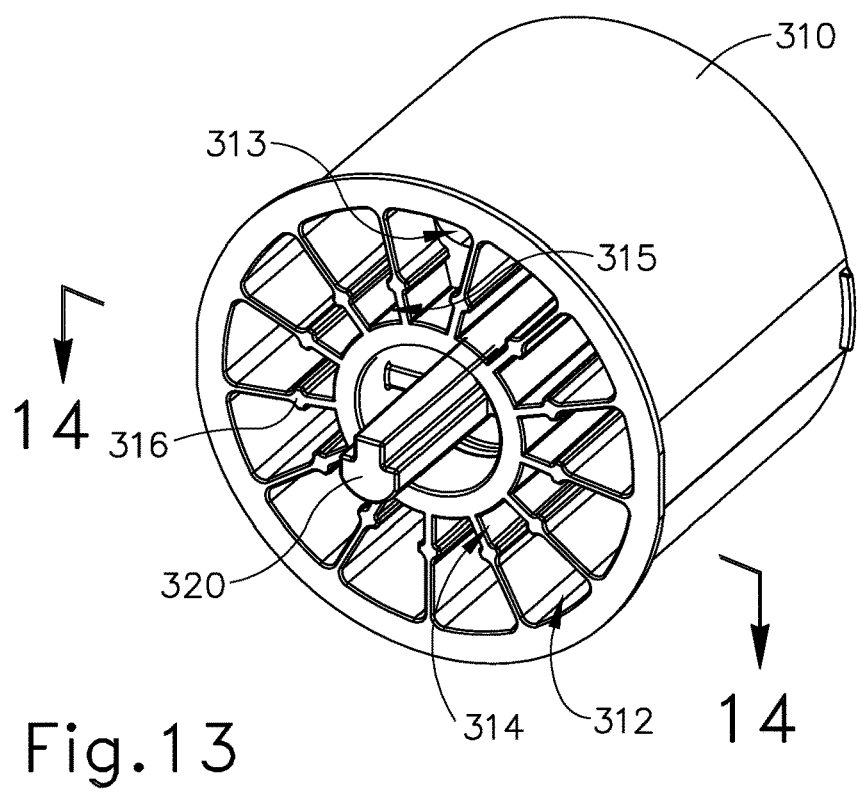
FIG. 13 depicts a perspective view of a rotatable manifold of the tissue sample holder assembly of FIG. 9.
Figure 14:
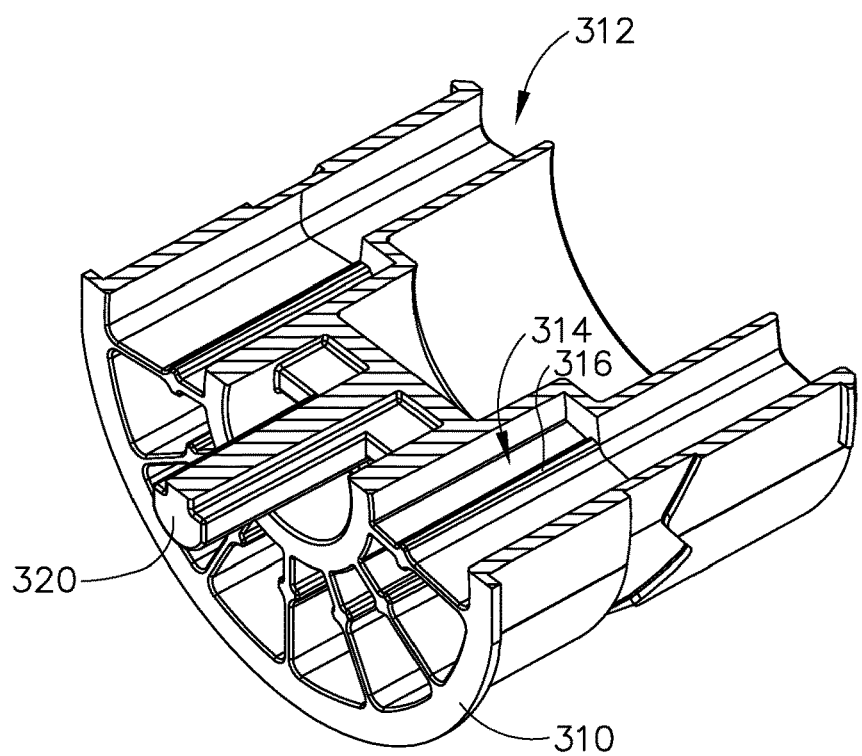
FIG. 14 depicts a cross-sectional view of the manifold of FIG. 13, taken along line 14-14 of FIG. 13.

As best seen in FIGS. 12-14, manifold (310) of the present example defines a plurality of chambers in the form of passages (312) that extend longitudinally through manifold (310) and that are angularly arrayed about the central axis of manifold (310). As best seen in FIG. 14, a lateral recess (314) is associated with a distal portion of each passage (312). Shelves (316) demarcate boundaries between each passage (312) and the associate lateral recess (314). As will be described in greater detail below, passages (312) receive trays (330) while recesses (314) provide pneumatic passages. An additional passage (313) and recess (315) are associated with a plug (370), as will also be described in greater detail below. Manifold (310) also includes a central shaft (320), which is configured to removably engage grasping feature (184). Central shaft (320) couples with grasping feature (184) upon coupling of cover (302) with chassis (106), as described above. Engagement between central shaft (320) and grasping feature (184) provides rotation of manifold (310) upon rotation of gear (182).

Figure 9:
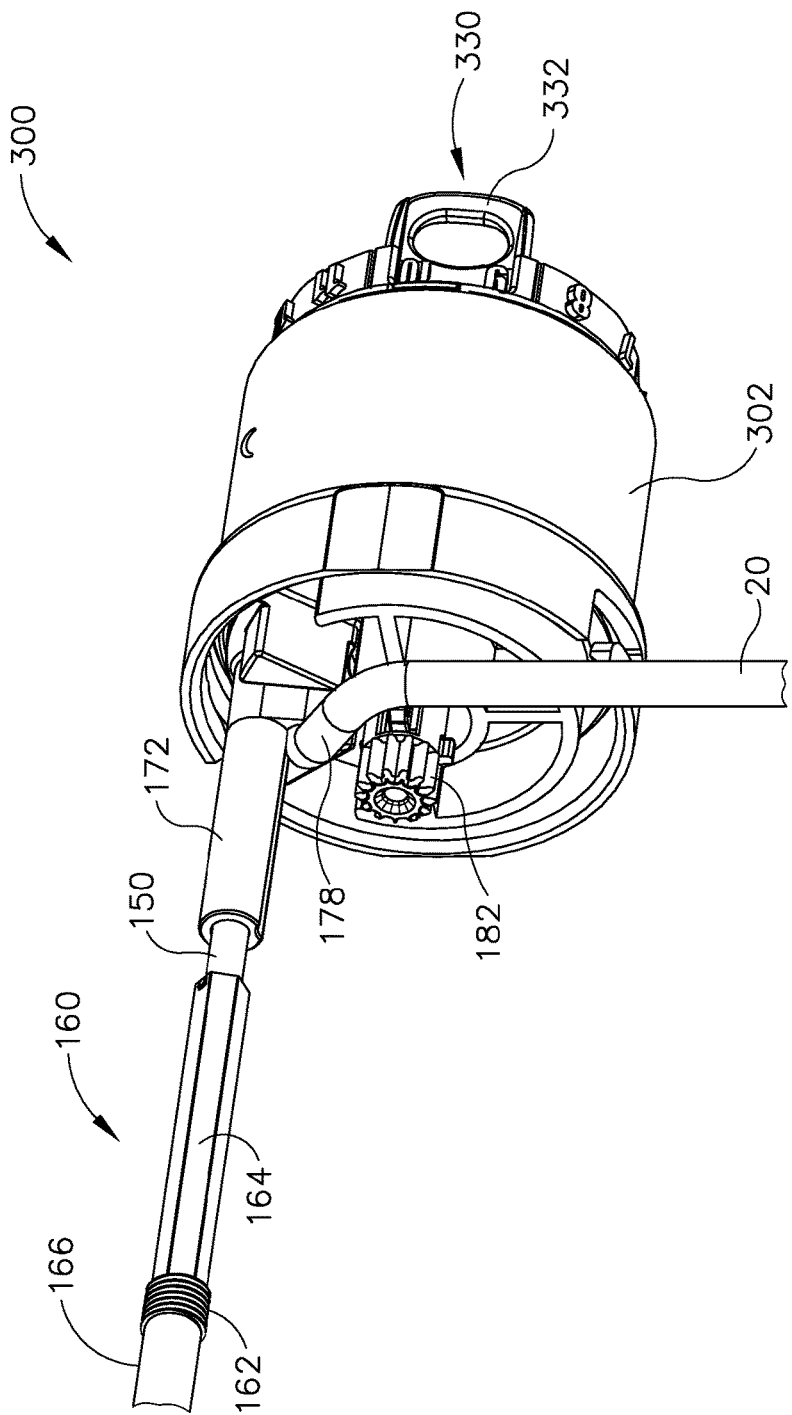
FIG. 9 depicts a perspective view of a tissue sample holder assembly of the probe of FIG. 4.
Figure 10:
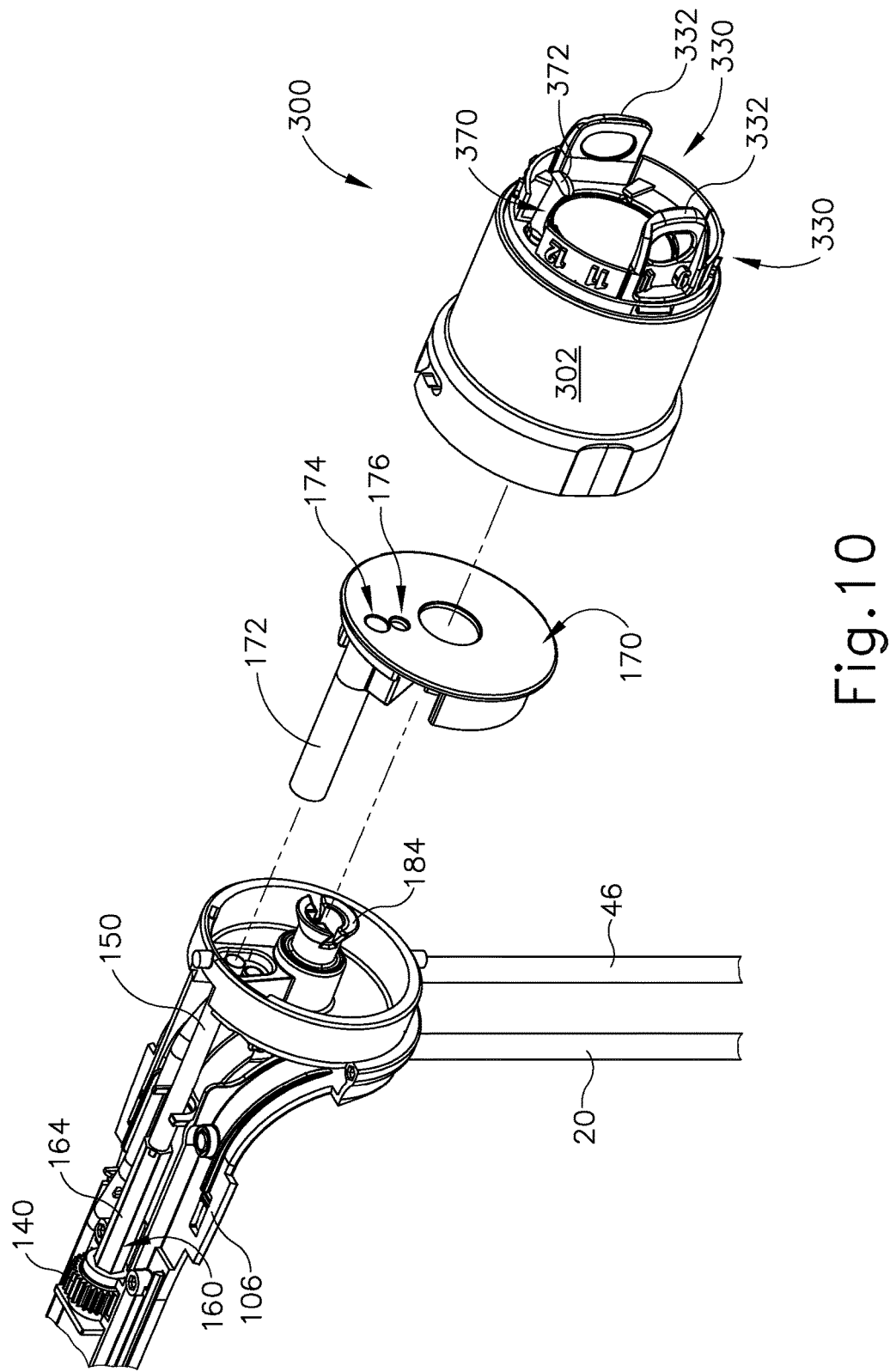
FIG. 10 depicts an exploded view of a proximal end of the probe of FIG. 4.
Figure 11:
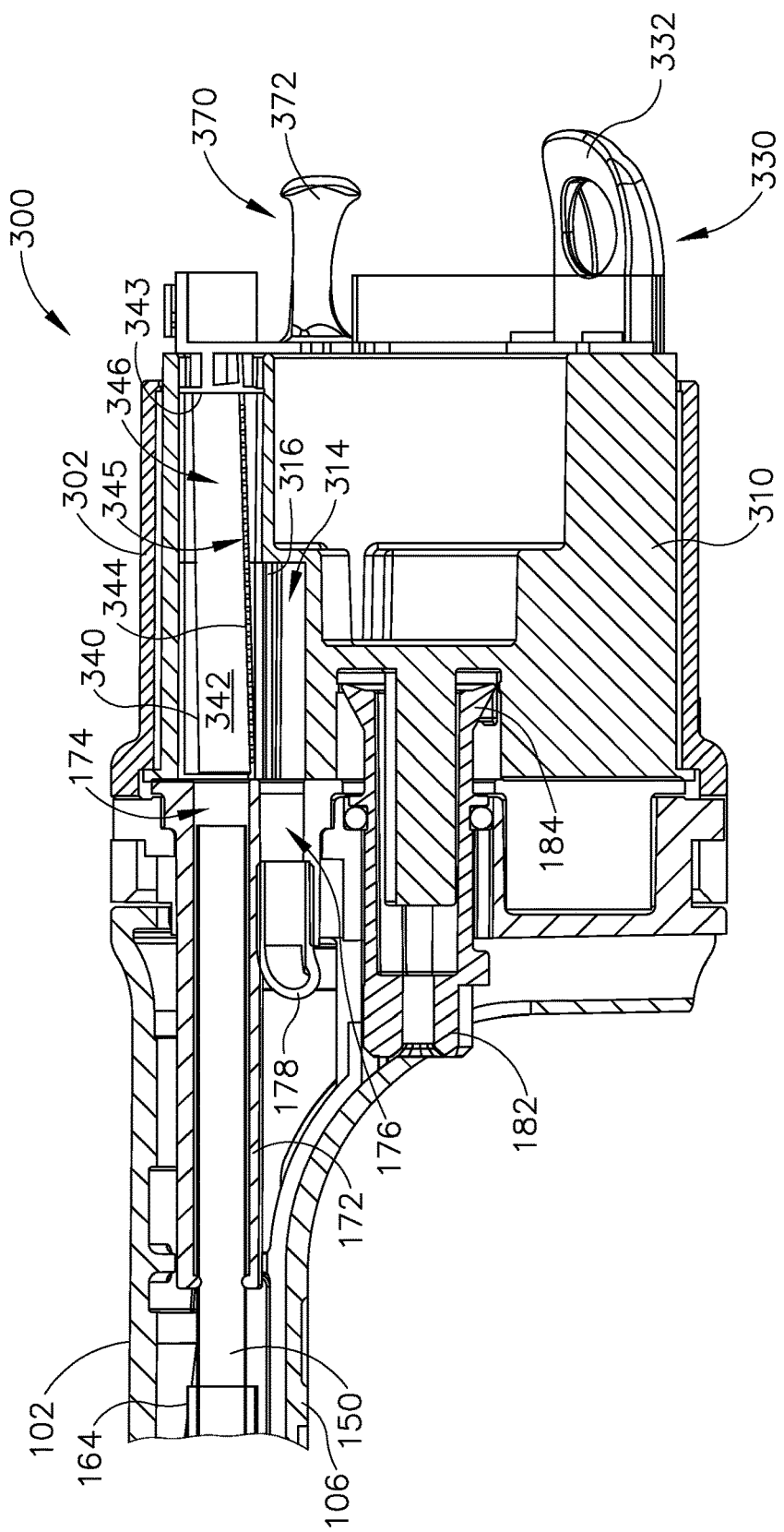
FIG. 11 depicts a side cross-sectional view of the tissue sample holder assembly of FIG. 9, with a tissue sample chamber aligned with the cutter.

As best seen in FIGS. 10-11, a sealing member (170) is provided at the proximal end of chassis (106) and interfaces with the distal face of manifold (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, manifold (310) further provides fluid communication between such recess (314, 315) and the associated passage (312, 313) at the 12 o'clock position; and thereby further to lumen (151) of cutter (150). In other words, sealing member (170) and manifold (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of manifold (310), even as manifold (310) is rotated relative to sealing member (170).

2. Exemplary Tissue Holder Trays

Figure 15:
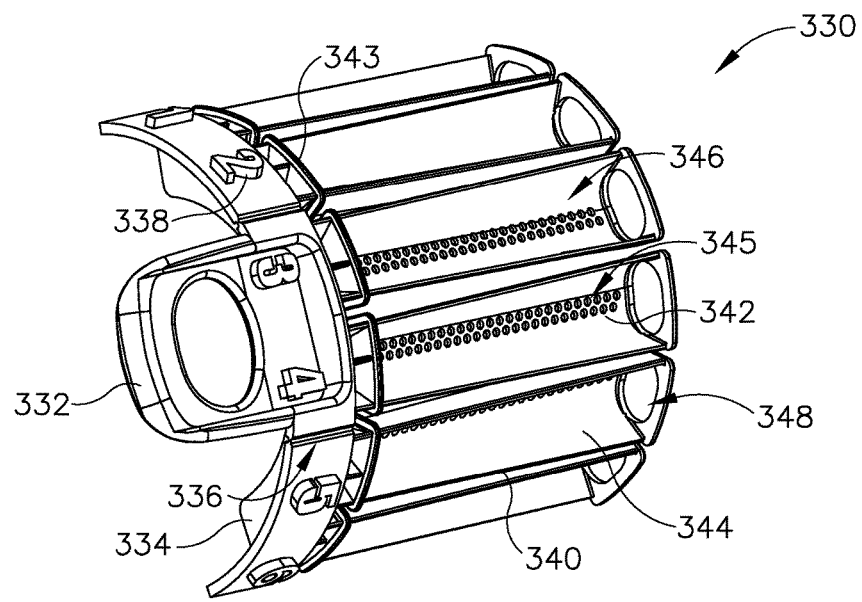
FIG. 15 depicts a perspective view of a tissue sample tray of the tissue sample holder assembly of FIG. 9.
Figure 16:
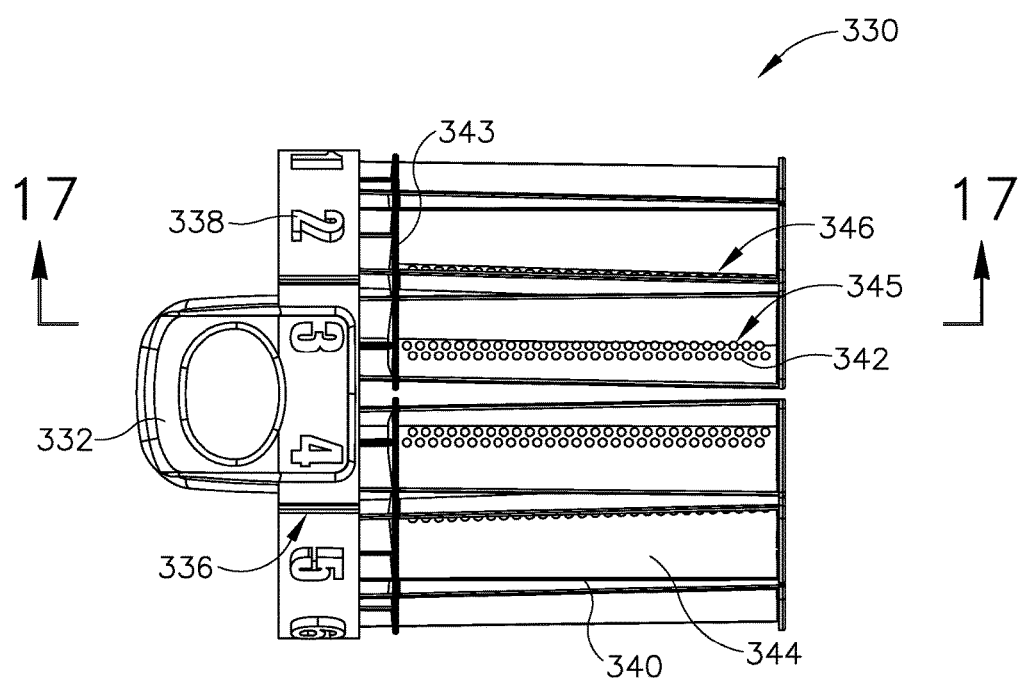
FIG. 16 depicts a top plan view of the tray of FIG. 15.
Figure 17:
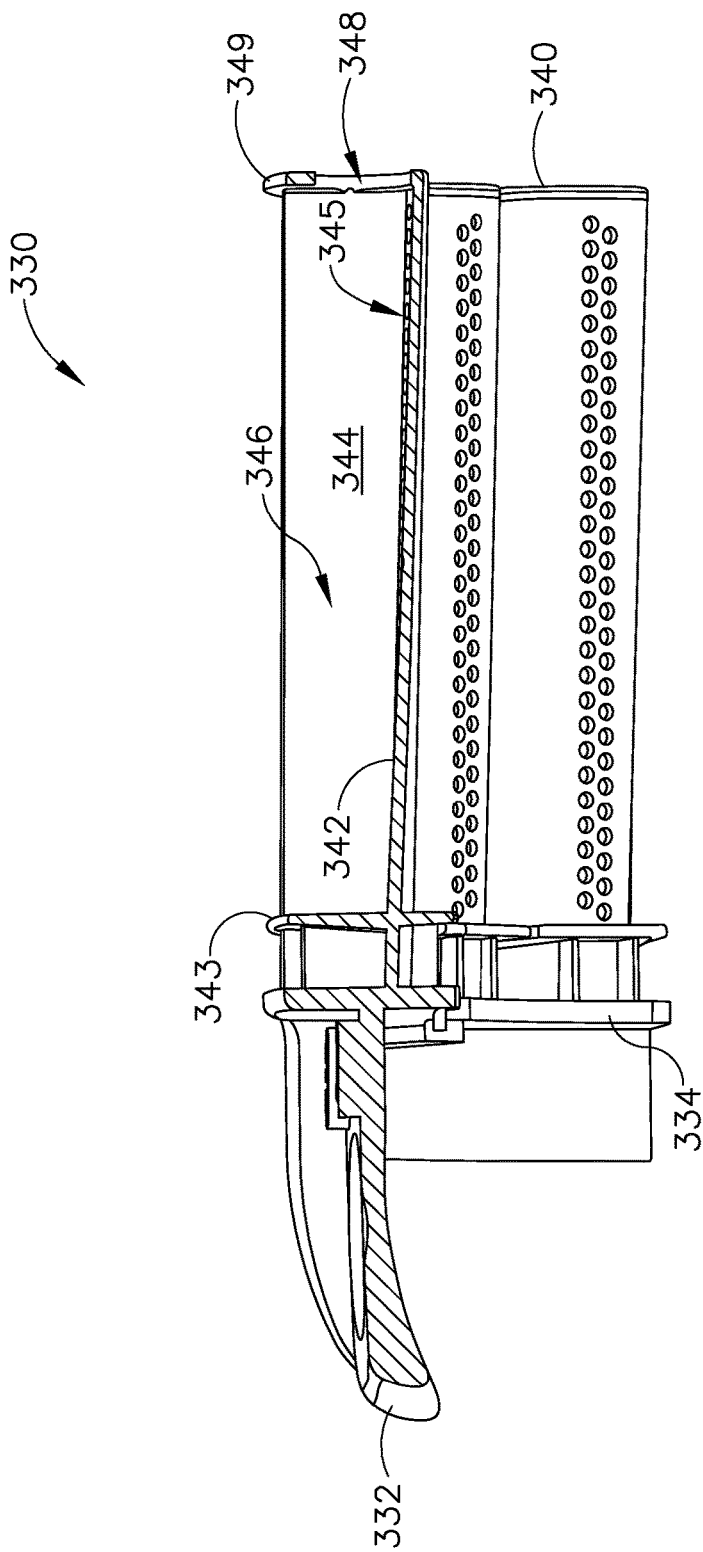
FIG. 17 depicts a cross-sectional view of the tray of FIG. 15, taken along line 17-17 of FIG. 16.

As noted above, tissue sample holder trays (330) are configured to removably engage manifold (310). As best seen in FIGS. 15-17, each tissue sample holder tray (330) of the present example includes a grip (332), a proximal wall (334), and a plurality of strips (340) extending distally from proximal wall (334). Strips (340) are sized and configured for insertion into associated passages (312) of manifold (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of manifold (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Manifold (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from manifold (310). Grips (332) are configured to facilitate removal of strips (340) from manifold (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into manifold (310); while also enabling trays (330) to form a generally flat configuration such as after trays (330) are removed from manifold (310) for inspection of tissue samples in trays (330).

It should be understood that manifold (310) and/or trays (330) may be configured in numerous other ways. By way of example only, manifold (310) and/or trays (330) may be configured in accordance with at least some of the teachings of U.S. Pub. No. 2008/0214955, the disclosure of which is incorporated by reference herein. As another merely illustrative example, manifold (310) and/or trays (330) may be configured in accordance with at least some of the teachings of U.S. Pub. No. 2010/0160824, the disclosure of which is incorporated by reference herein. It should also be understood that tissue sample holder (300) need not necessarily position chambers (346) coaxially with lumen (151) of cutter (150). Tissue sample holder (300) may index chambers (346) relative to cutter (150) in any other suitable fashion. For instance, chambers (346) may extend along axes that are always offset from the axis of lumen (151), along axes that are oblique or perpendicular relative to the axis of lumen (151), or along other axes. Similarly, it should be understood that manifold (310) may rotate about an axis that is oblique or perpendicular relative to the axis of lumen (151). Still other suitable configurations will be apparent to those of ordinary skill in the art in view of the teachings herein.

3. Exemplary Accessory Chamber and Plug

Figure 18:
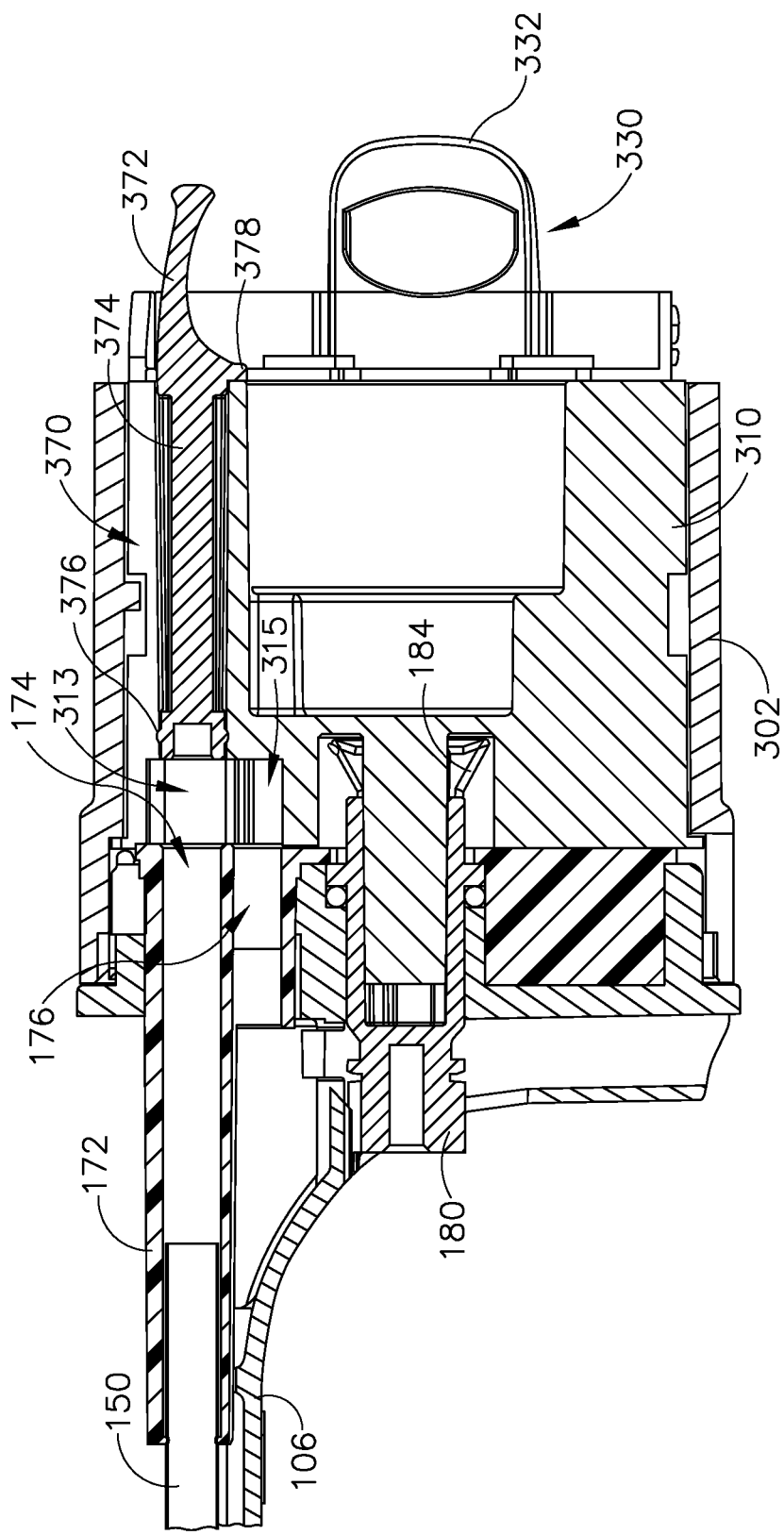
FIG. 18 depicts a side cross-sectional view of the tissue sample holder assembly of FIG. 9, with a plug aligned with the cutter.
Figure 19:
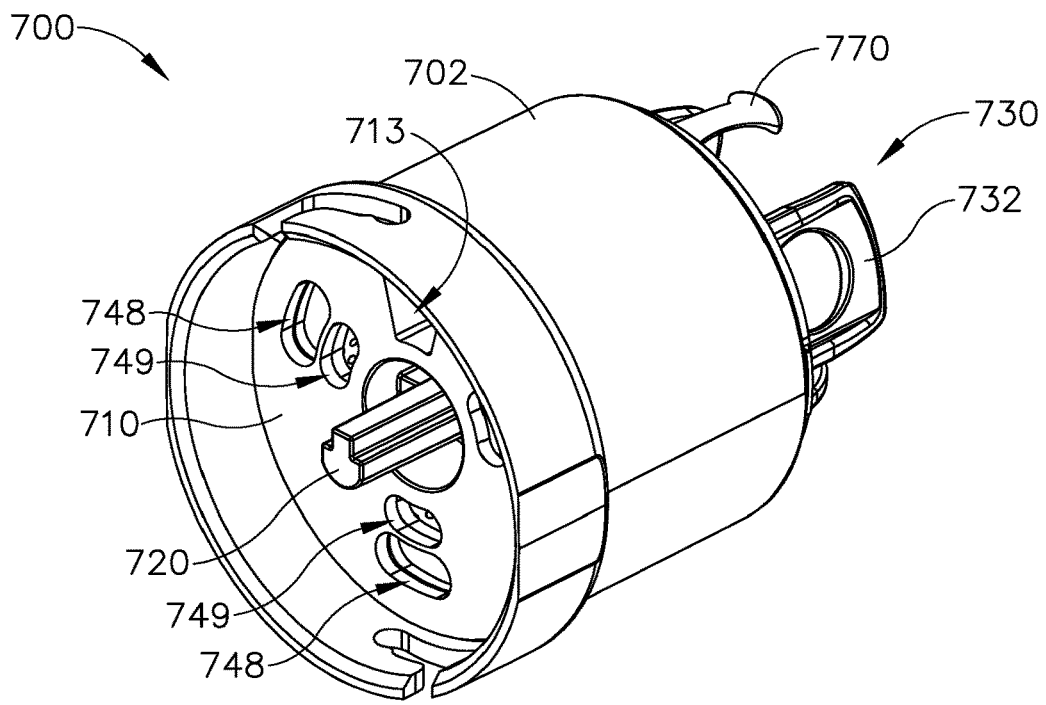
FIG. 19 depicts a perspective view of an exemplary alternative tissue sample holder assembly that may be incorporated into the probe of FIG. 4.
Figure 20:
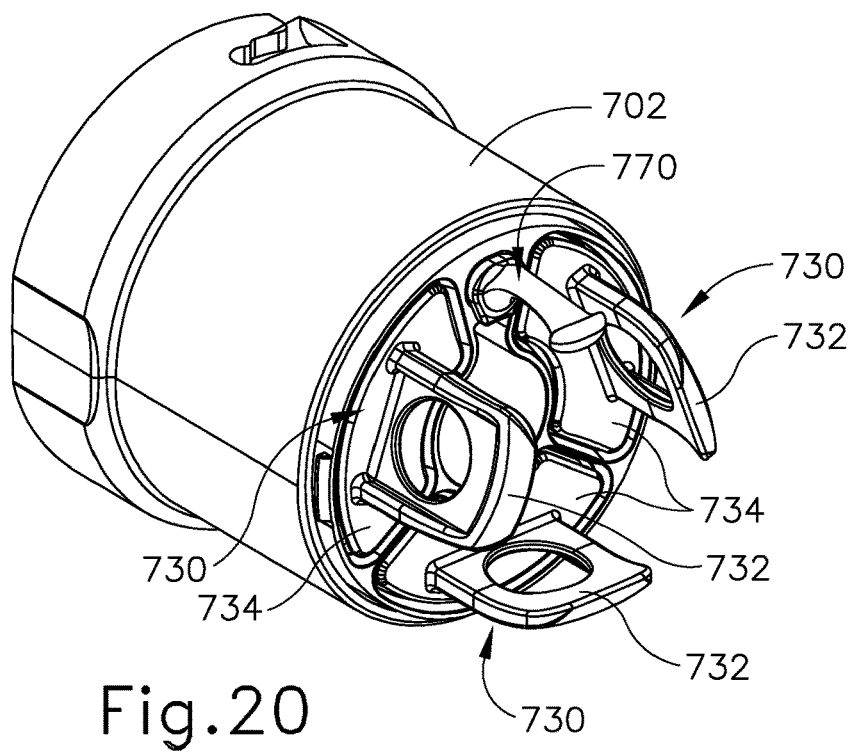
FIG. 20 depicts another perspective view of the tissue sample holder assembly of FIG. 19.
Figure 21:
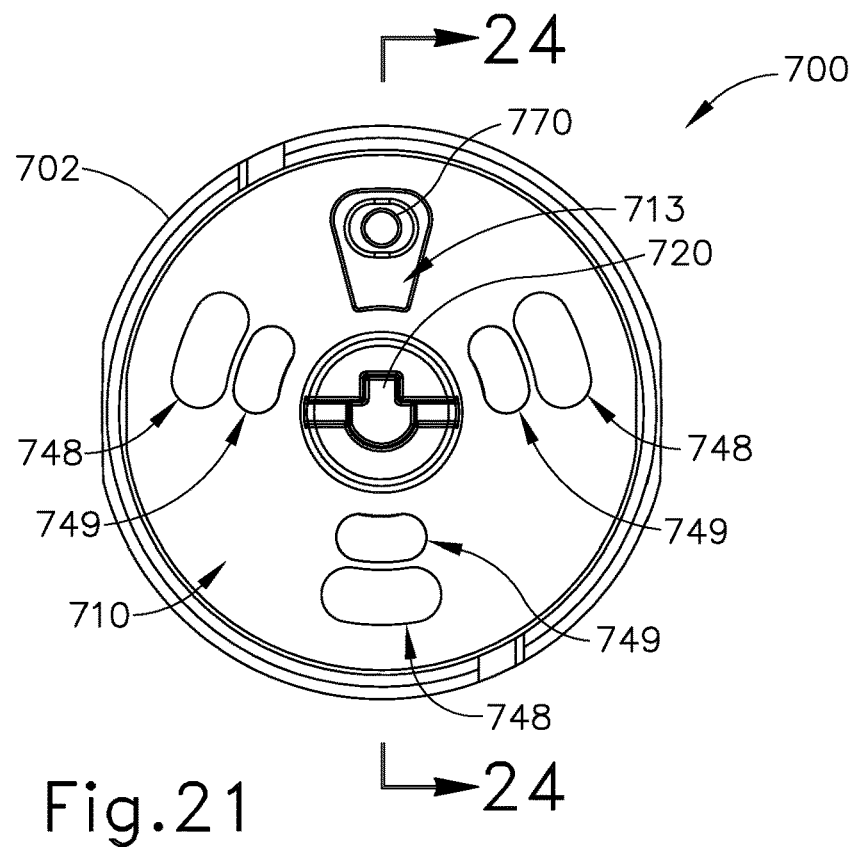
FIG. 21 depicts a front elevational view of the tissue sample holder assembly of FIG. 19.
Figure 22:
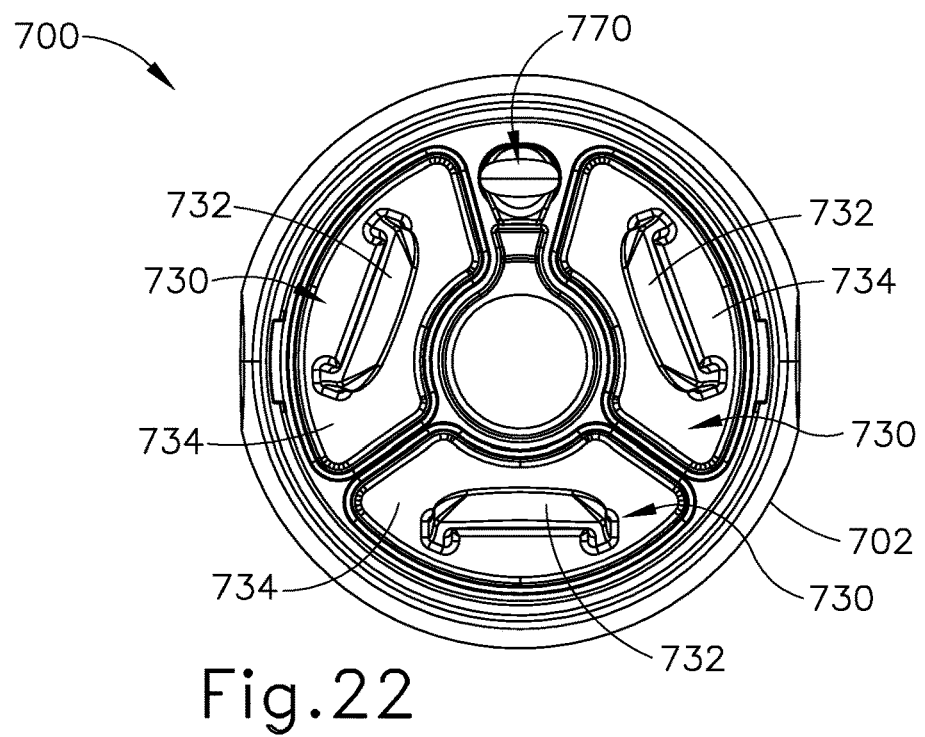
FIG. 22 depicts a rear elevational view of the tissue sample holder assembly of FIG. 19.

As best seen in FIGS. 12 and 18 and as noted above, tissue sample holder (300) of the present example includes a plug (370) that is received in a dedicated passage (313) of manifold (310). Plug (370) includes a grip (372) and a longitudinally extending body (374). Body (374) extends through part of the length of passage (313), distally terminating at the longitudinal position corresponding with the proximal end of recess (315). Plug (370) includes a pair of seals (376, 378) that seal against the interior of passage (313) when plug (370) is fully inserted in passage (313). Seals (376, 378) thus keep passage (313) fluid tight when plug (370) is inserted in passage (313). Passage (313) is configured to receive the shaft of a biopsy site marker applier. Passage (313) may also receive an instrument for delivering medicine, etc. to a biopsy site. By way of example only, passage (313) may receive an adapter configured to provide an interface between passage (313) and a conventional medicine delivery device. An example of such an adapter and other uses/configurations for a passage like passage (313) are described in U.S. Pub. No. 2008/0221480, the disclosure of which is incorporated by reference herein. Plug (370) and/or passage (313) may also be configured and operable in accordance with at least some of the teachings of U.S. Pub. No. 2013/0041256, the disclosure of which is incorporated by reference herein. Still other suitable configurations will be apparent to those of ordinary skill in the art in view of the teachings herein. In some other versions, plug (370) and/or passage (313) are simply omitted.

D. Exemplary Alternative Tissue Sample Holder Assembly

FIGS. 19-29 show an exemplary alternative tissue sample holder (700) that is similar to tissue sample holder (300) described above. Tissue sample holder (700) of the present example provides a plurality of discrete chambers that are configured to receive tissue samples that are severed by cutter (150) and communicated proximally through lumen (151) of cutter (150). In particular, and as will be described in greater detail below, tissue sample holder (700) includes tissue receiving trays (730) that are removably engaged with a manifold (710). Manifold (710) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate manifold (710) to index tissue chambers relative to lumen (151) of cutter (150) as will be described in greater detail below. A transparent cover (702) is positioned about manifold (710) and is removably secured to chassis (106). While bayonet features provide coupling between cover (702) and chassis (106), it should be understood that any suitable type of coupling may be used. Manifold (710) is freely rotatable within cover (702). However, manifold (710) is engaged with cover (702) such that manifold (710) will decouple relative to chassis (106) when cover (702) is removed from chassis (106). In other words, manifold (710) may be selectively coupled with and removed relative to chassis (106) by coupling and removing cover (702) from chassis (106).

Figure 23:
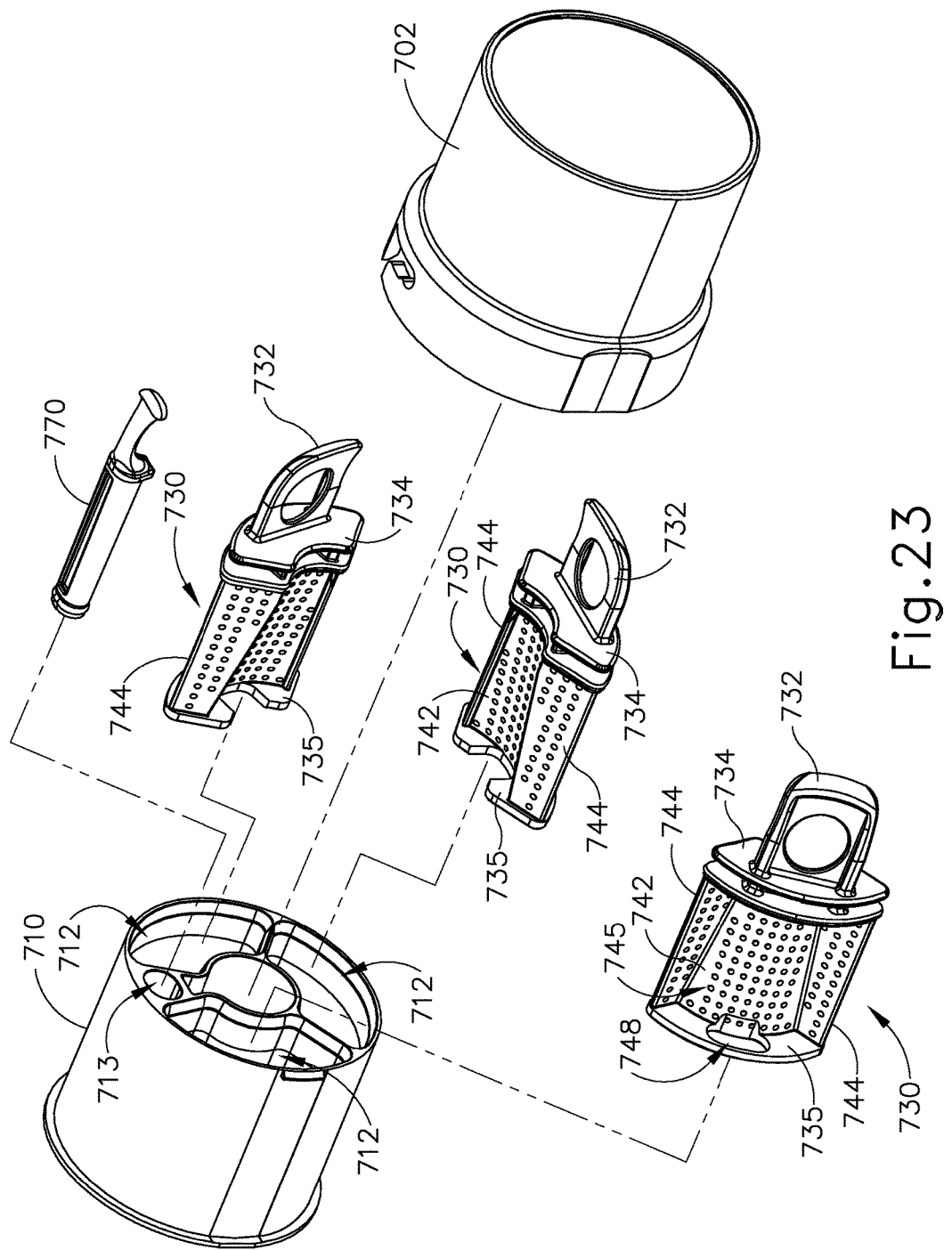
FIG. 23 depicts an exploded perspective view of the tissue sample holder assembly of FIG. 19.
Figure 24:
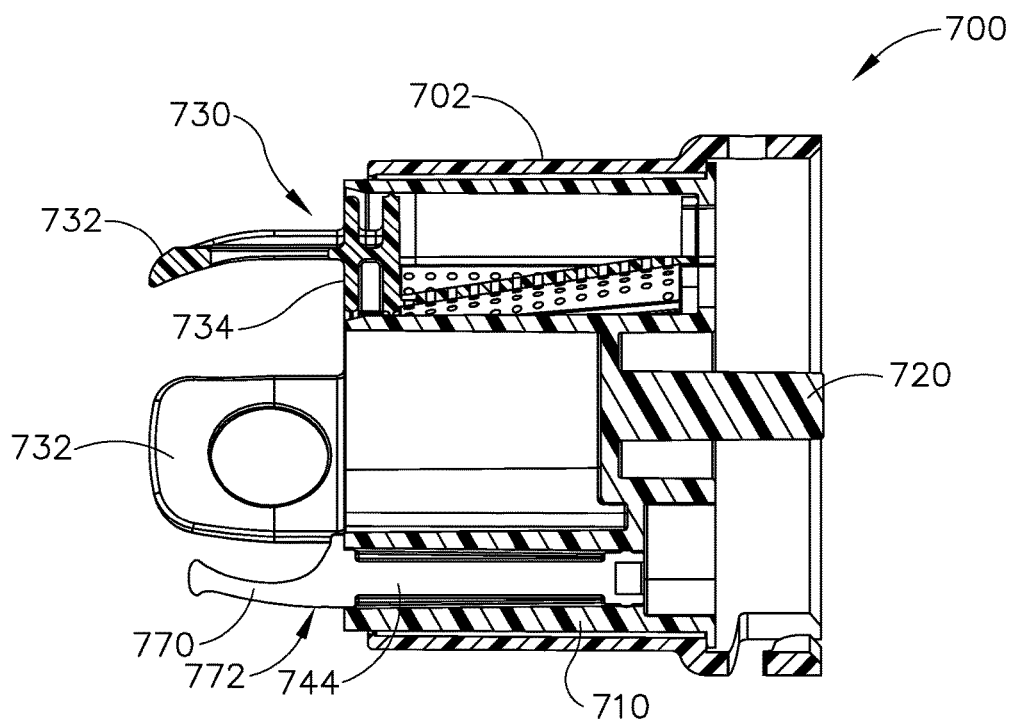
FIG. 24 depicts a cross-sectional side view of the tissue sample holder assembly of FIG. 19, taken along line 24-24 of FIG. 21.
Figure 25:
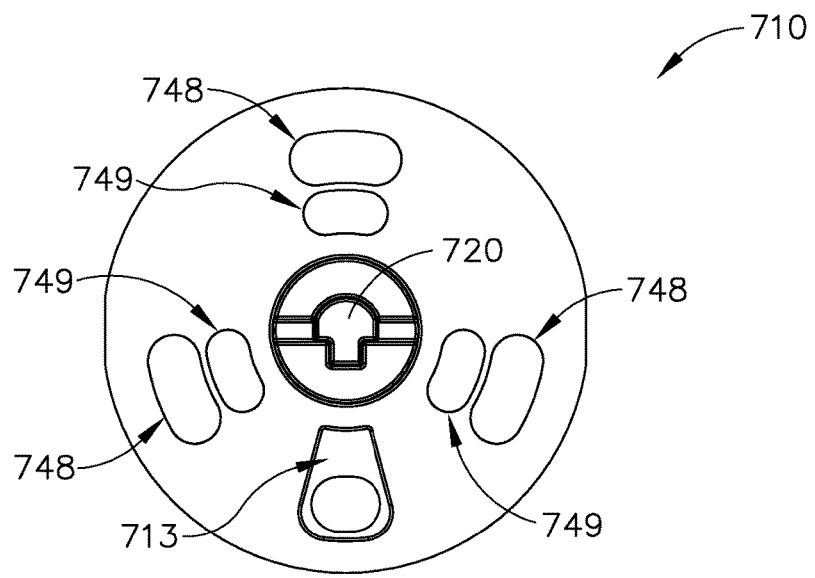
FIG. 25 depicts a front elevational view of a rotatable body of the tissue sample holder assembly of FIG. 19.
Figure 26:
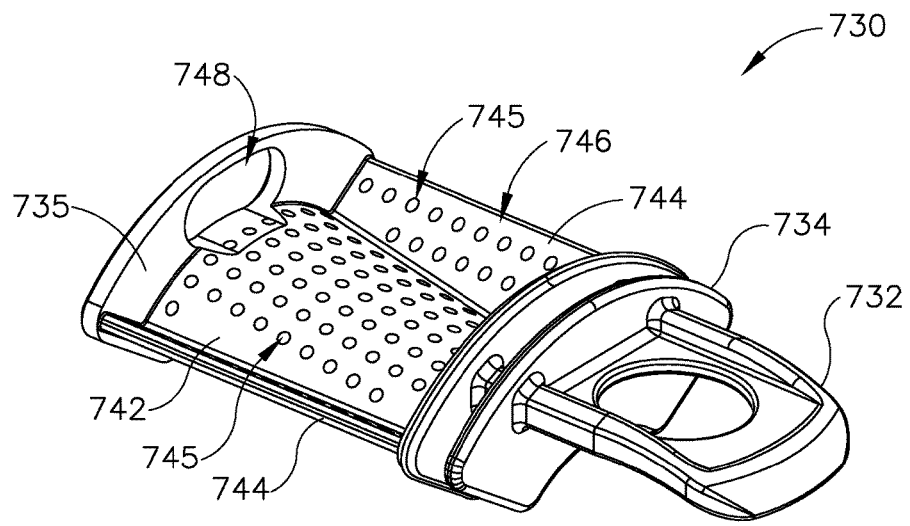
FIG. 26 depicts a perspective view of a tissue sample tray of the tissue sample holder assembly of FIG. 19.
Figure 27:
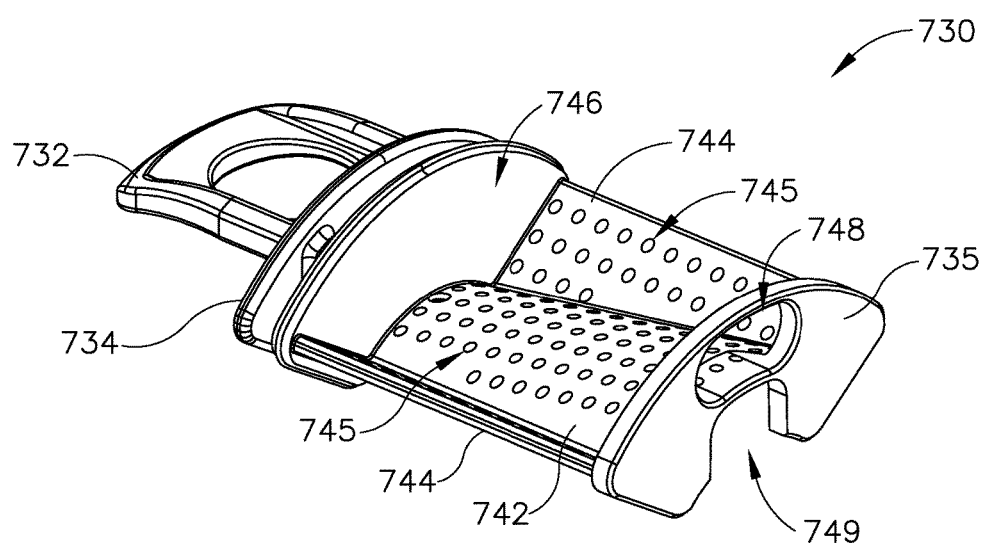
FIG. 27 depicts another perspective view of the tissue sample tray of FIG. 26.
Figure 28:
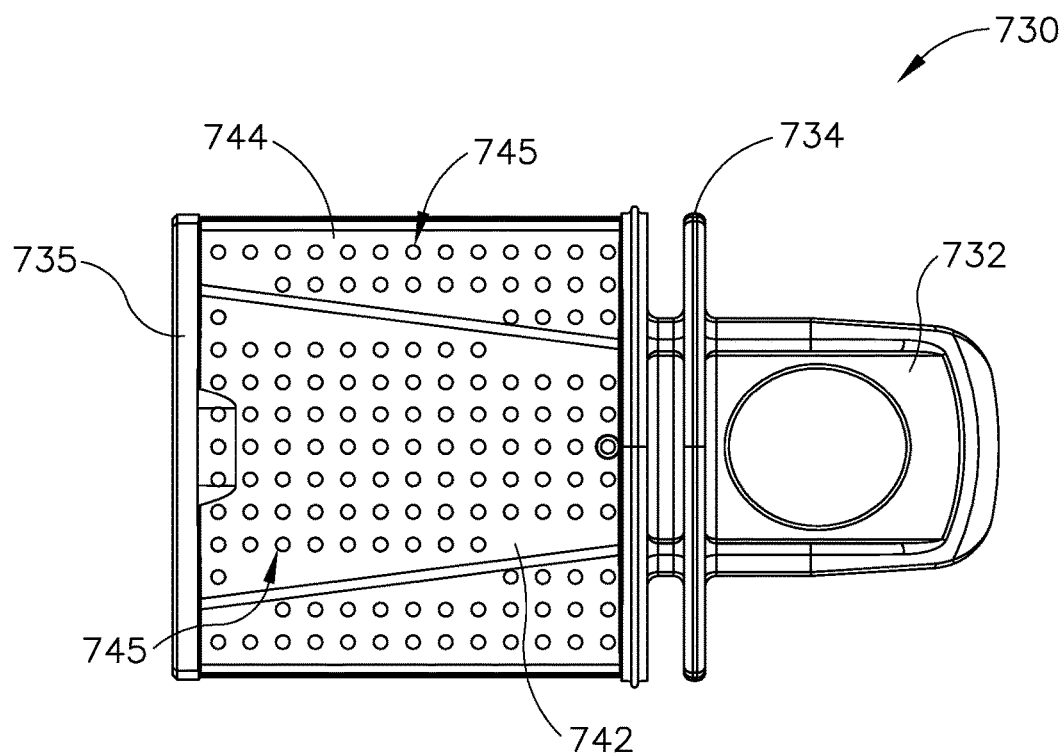
FIG. 28 depicts a top plan view of the tissue sample tray of FIG. 26.
Figure 29:
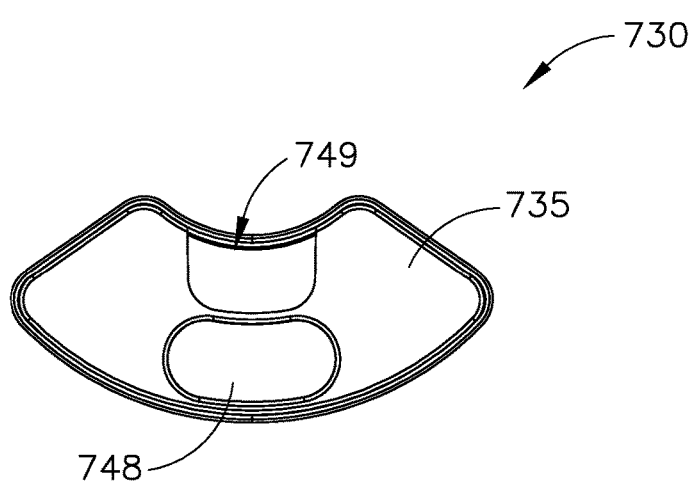
FIG. 29 depicts a front elevational view of the tissue sample tray of FIG. 26.
Figure 30:
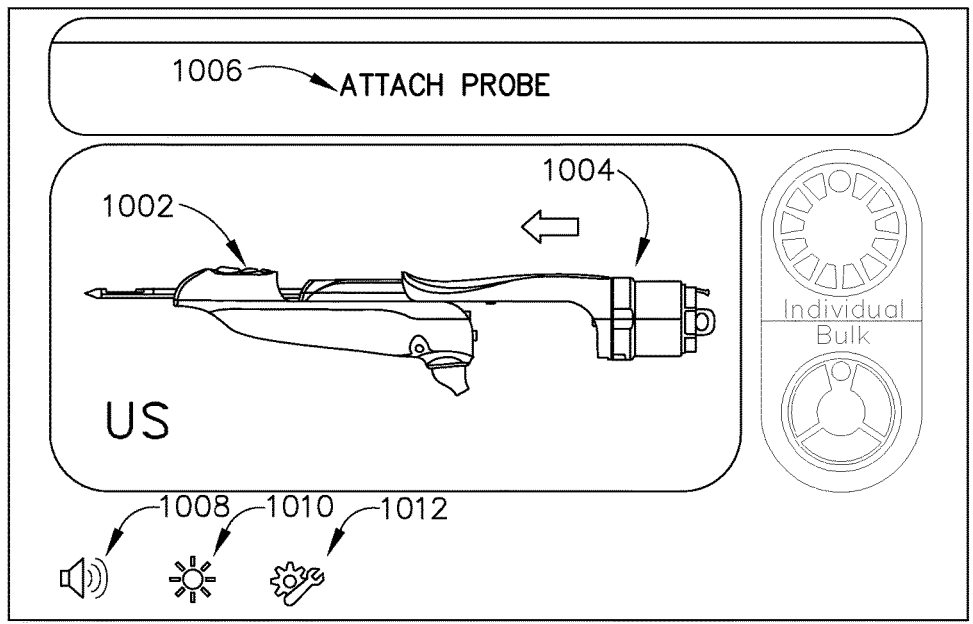
FIG. 30 depicts an exemplary first user interface screen for display on the vacuum control module of FIG. 1.

As best seen in FIGS. 23 and 24, manifold (710) of the present example defines a plurality of chambers in the form of passages (712) that extend longitudinally through manifold (710) and that are angularly arrayed about the central axis of manifold (710). Unlike manifold (310), manifold of the present example omits structures similar to recesses (314) and shelves (316) of manifold (310). Instead, as will be described in greater detail below, passages (712) receive trays (730) and trays (730) define pneumatic passages. Similarly, only a single passage (713) (but no recess) is associated with a plug (770), as will also be described in greater detail below. Manifold (710) also includes a central shaft (720), which is configured to removably engage grasping feature (184). Central shaft (720) couples with grasping feature (184) upon coupling of cover (702) with chassis (106) to provide rotation of manifold (710) upon rotation of gear (182).

As noted above, tissue sample holder trays (730) are configured to removably engage manifold (710). As best seen in FIGS. 26-29, each tissue sample holder tray (730) of the present example includes a grip (732), a proximal wall (734), and a strip (740) extending distally from proximal wall (734) to a distal wall (735). Strip (740) is sized and configured for insertion into a single passage (712) of manifold (710). Unlike tissue sample holder tray (330), tissue sample holder tray (730) occupies the entire passage (712) of manifold (710), as will be described in greater detail below. Strip (740) includes a pair of sidewalls (744) and a floor (742). Sidewalls (744) and floor (742) together define a corresponding tissue sample chamber (746). Additionally, sidewalls (744) and floor (742) together define a pneumatic passageway (714), unlike strip (340) of tissue sample holder tray (330). In particular, floor (742) slopes upwardly as floor (742) extends distally. Correspondingly, sidewalls (744) have an angled edge that joins with floor (742) to accommodate the upward slope of floor (742). Floor (742) may also include a curvature to further increase the volume of pneumatic passageway, although such a curvature is merely optional.

Distal wall (735) of tissue sample holder trays (730) provides two openings (748, 749), which may engage sealing member (170), described above. Opening (748) is sized and positioned to correspond with opening (174) of sealing member (170). Thus, the lumen (151) of cutter (150) is in fluid communication with the tissue sample chamber (746) of the strip (740) inserted in the passage (712) that is at the 12 o'clock position. Similarly, opening (749) is sized and positioned to correspond with opening (176) of sealing member (170) to communicate vacuum with pneumatic passage (714). Each sidewall (744) and floor (742) includes a plurality of openings (745) that provide fluid communication between tissue sample chamber (346) of strip (340) and pneumatic passageway (714). Thus, vacuum, atmospheric air, etc. that is communicated to opening (176) via tube (20) is further communicated to lumen (151) of cutter (150) via pneumatic passageway (714), openings (745), and tissue sample chamber (746). During operation of biopsy device (10), tissue samples severed by distal edge (152) of cutter (150) are communicated proximally through the lumen (151) of cutter (150) and are then deposited into the tissue sample chamber (746) that is aligned with lumen (151) of cutter (150). Manifold (710) is rotated to successively align tissue sample chambers (746) with lumen (151) of cutter (150), enabling several tissue samples to be separately deposited in different tissue sample chambers (746) during operation of biopsy device (10). Alternatively, each tissue sample chamber (746) may collect a predetermined number of tissue samples prior to being rotated to align a new tissue sample chamber (746) with lumen (151) of cutter (150). Regardless, bodily fluids and saline, etc. that are pulled through lumen (151) will pass through tissue sample holder (700) and tube (20) and are eventually deposited in vacuum canister (70).

It should be understood that manifold (710) and/or trays (730) may be configured in numerous other ways. By way of example only, manifold (710) and/or trays (730) may be configured in accordance with at least some of the teachings of U.S. Pub. No. 2008/0214955, the disclosure of which is incorporated by reference herein. As another merely illustrative example, manifold (710) and/or trays (730) may be configured in accordance with at least some of the teachings of U.S. Pub. No. 2010/0160824, the disclosure of which is incorporated by reference herein. It should also be understood that tissue sample holder (700) need not necessarily position chambers (746) coaxially with lumen (151) of cutter (150). Tissue sample holder (700) may index chambers (746) relative to cutter (150) in any other suitable fashion. For instance, chambers (746) may extend along axes that are always offset from the axis of lumen (151), along axes that are oblique or perpendicular relative to the axis of lumen (151), or along other axes. Similarly, it should be understood that manifold (710) may rotate about an axis that is oblique or perpendicular relative to the axis of lumen (151). Yet in other configuration, it should be understood that manifold (710) may be rotated or indexed by motors in probe (100) or holster (200). Yet in still other examples, tissue sample holder may be manually rotatable by the hand of the user. By way of example only, such a manually rotatable manifold (710) may be configured in accordance with at least some of the teachings of U.S. Pat. App. No. 62/054,523, titled "MRI Biopsy System," filed on Sep. 24, 2014, the disclosure of which is incorporated by reference herein. Still other suitable configurations will be apparent to those of ordinary skill in the art in view of the teachings herein.

As best seen in FIG. 24 and as noted above, tissue sample holder (700) of the present example includes a plug (770) that is received in a dedicated passage (713) of manifold (710). Plug (770) includes a grip (772) and a longitudinally extending body (374). Body (774) extends through part of the length of passage (713). Plug (770) may also include a plurality of seals, similar to seals (376, 378) described above, that seal against the interior of passage (713) when plug (770) is fully inserted in passage (713). Passage (713), similar to passage (313) described above, is configured to receive the shaft of a biopsy site marker applier. Passage (713) may also receive an instrument for delivering medicine, etc. to a biopsy site. By way of example only, passage (713) may receive an adapter configured to provide an interface between passage (713) and a conventional medicine delivery device. An example of such an adapter and other uses/configurations for a passage like passage (713) are described in U.S. Pub. No. 2008/0221480, the disclosure of which is incorporated by reference herein. Plug (770) and/or passage (713) may also be configured and operable in accordance with at least some of the teachings of U.S. Pub. No. 2013/0041256, the disclosure of which is incorporated by reference herein. Still other suitable configurations will be apparent to those of ordinary skill in the art in view of the teachings herein. In some other versions, plug (770) and/or passage (713) are simply omitted.

By way of example only, tissue sample holder (300, 700) may be constructed in accordance with at least some of the teachings of U.S. patent application Ser. No. 14/469,761, entitled "Tissue Collection Assembly for Biopsy Device," filed Nov. 13, 2014, the disclosure of which is incorporated by reference herein. Still other suitable forms that tissue sample holder (300, 700) may take will be apparent to those of ordinary skill in the art in view of the teachings herein.

IV. Exemplary Graphical User Interface

A. Exemplary Initial Setup Screens

FIGS. 30-34 show exemplary screens (1000, 1020, 1040, 1060, 1080) that may be displayed on touchscreen (410) during setup of biopsy system (2). In particular, screen (1000) shown in FIG. 30 includes a graphical representation (1002) of holster (200) and a graphical representation (1004) of probe (100), with a textual instruction (1006) to attach probe (100) to holster (200). Screen (1000) also includes a volume adjustment button (1008), a brightness adjustment button (1010), and a settings adjustment button (1012). It should be understood that, while the term "button" is used herein, the same should not be read as requiring an electromechanical button that has a movable feature. The term may include interactive icons and other features of a flat touchscreen, etc. If the user taps volume adjustment button (1008), a sub-screen will pop up enabling the user to select a volume level for audio feedback emitted by vacuum control module (400). If the user taps brightness adjustment button (1010), a sub-screen will pop up enabling the user to select a brightness level for touchscreen (410). If the user taps settings adjustment button (1012), a sub-screen will pop up enabling the user to adjust various settings for vacuum control module (400) (e.g., language, etc.).

Figure 31:
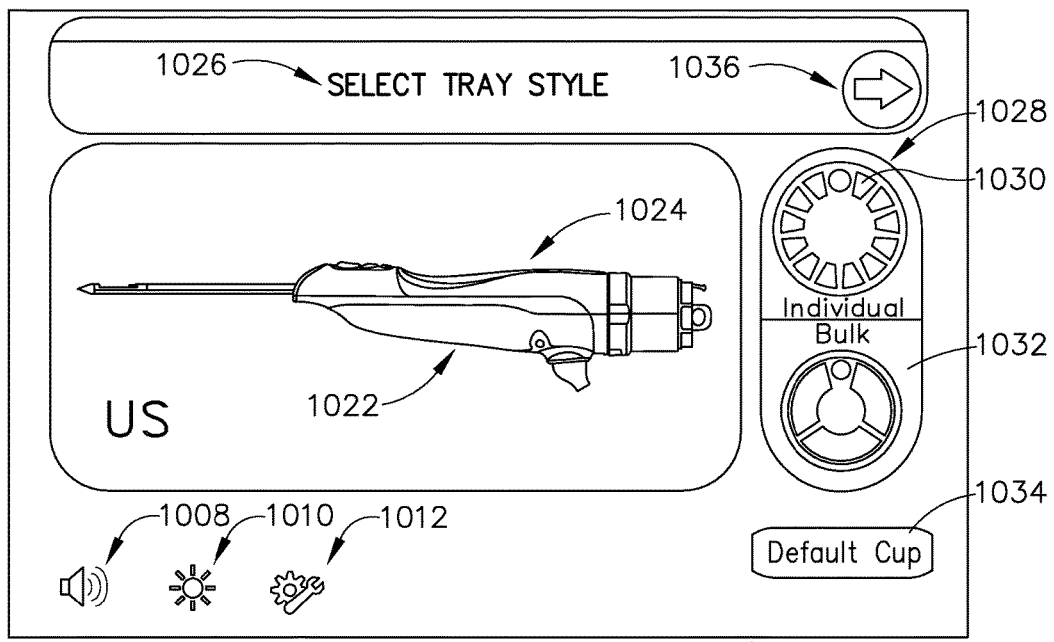
FIG. 31 depicts an exemplary second user interface screen for display on the vacuum control module of FIG. 1.

As soon as the user attaches probe (100) to holster (200), touchscreen (410) automatically transitions to screen (1020) shown in FIG. 31. It should therefore be understood that vacuum control module (400) includes circuitry configured to sense when probe (100) is attached to holster (200). For instance, in some examples probe (100) may contain a magnet and holster (200) may contain a sensor configured to detect the magnetic field generated by the magnet in probe (100). Various other forms that such circuitry may take will be apparent to those of ordinary skill in the art in view of the teachings herein. Screen (1020) includes a graphical representation (1022) of holster (200) and a graphical representation (1024) of probe (100), with a textual instruction (1026) to select tray style. In the present example, the user may select a "tray style" based on whether tissue sample holder (300) or tissue sample holder (700) is coupled with probe (100). Screen (1020) also includes volume adjustment button (1008), brightness adjustment button (1010), and settings adjustment button (1012), as described above.

With probe (100) attached to holster (200), tray selection buttons (1028) are visible on screen (1020). In particular, tray selection buttons (1028) comprise two tray style selector buttons (1030, 1032) and a default cup menu button (1034). Each tray style selector button (1030, 1032) graphically represents one of the tissue sample holder assemblies (300, 700) described above. The term "individual" thus indicates that each tissue receiving chamber in tissue sample holder assembly (300) is configured to generally hold just one individual tissue sample. Similarly, a "bulk" tray selector button (1032) graphically represents tissue sample holder assembly (700) described above. Accordingly, screen (1020) is configured to receive a user input as to which tissue sample holder assembly (300, 700) is attached to probe (100). Once the user selects a given tray style selector button (1030, 1032), the user may press a menu advance button (1036) to transition touchscreen (410) to a given sample screen (1200, 2200), as will be described in greater detail below. When the user presses on one of the style selector buttons (1030, 1032), that particular style selector button (1030, 1032) may illuminate brighter, change color, and/or other otherwise provide some visual feedback indicating that that particular style selector button (1030, 1032) has been activated. In addition or in the alternative, the non-activated style selector button (1030, 1032) may darken, change color, and/or other otherwise provide some visual feedback indicating that that particular style selector button (1030, 1032) has not been activated.

The "individual" designator used herein with respect to individual tray selector button (1030) refers to the use of tissue sample holder assembly (300) such that each tissue sample chamber (346) is configured/used to receive only one single tissue sample. Likewise, the "bulk" designator with respect to bulk tray selector button (1032) refers to the use of tissue sample holder assembly (700) such that each tissue sample chamber (746) is configured/used to receive multiple tissue samples. Although tray style selector buttons (1030, 1032) are referred to herein as corresponding to "individual" or "bulk" tray configurations, it should be understood that in other examples either tissue sample holder (300, 700) may be used in a way that may be characterized by "individual" or "bulk."

Figure 32:
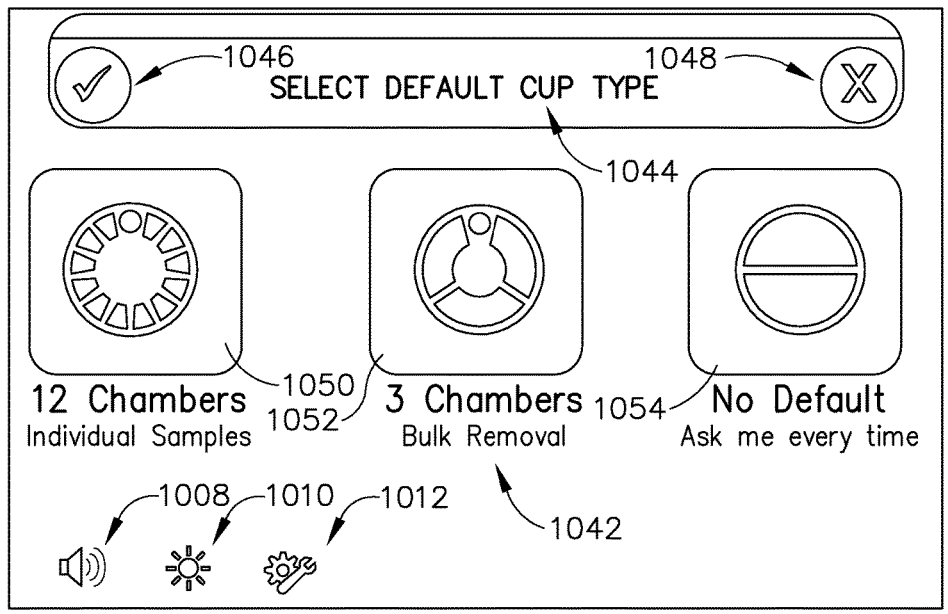
FIG. 32 depicts an exemplary third user interface screen for display on the vacuum control module of FIG. 1.

When Default cup menu button (1034) is selected by the user, touchscreen (410) transitions to screen (1040) shown in FIG. 32. Screen (1040) includes default tray style selection buttons (1042), a textual instruction (1044) to select default cup type, a confirmation button (1046), and a cancel button (1048). Screen (1040) also includes volume adjustment button (1008), brightness adjustment button (1010), and settings adjustment button (1012), as described above. Default tray style selection buttons (1042) comprise an individual default selection button (1050), a bulk default selection button (1052), and a no default selection button (1054). Individual default selection button (1050) is shown as graphically representing tissue sample holder assembly (300), while bulk default selection button (1052) is shown as graphically representing tissue sample holder assembly (700). Thus, the user may select either individual default selection button (1050) or bulk default selection button (1052) to indicate that biopsy system (2) will generally be used with tissue sample holder assembly (300) or tissue sample holder assembly (700), respectively. This may be desirable in clinical settings where the user uses tissue sample holder assembly (300) or tissue holder assembly (700) exclusively. Where a default is selected, screen (1020) may be skipped entirely and touchscreen (410) may proceed to screen (1060), described above. If the user has no preference or uses tissue sample holder assemblies (300, 700) interchangeably, then the user may select no default selection button (1050). When no default selection button (1050) is engaged by the user, touchscreen (410) will proceed to screen (1020) from screen (1000) when probe (100) is attached to holster (200). Once the user has selected a default setting, the user may press confirmation button (1046) to save the default setting and return to screen (1020). Alternatively, if the user simply desires to cancel selecting a default setting, the user may press cancel button (1048) to return to screen (1020) without saving a default setting.

Figure 33:
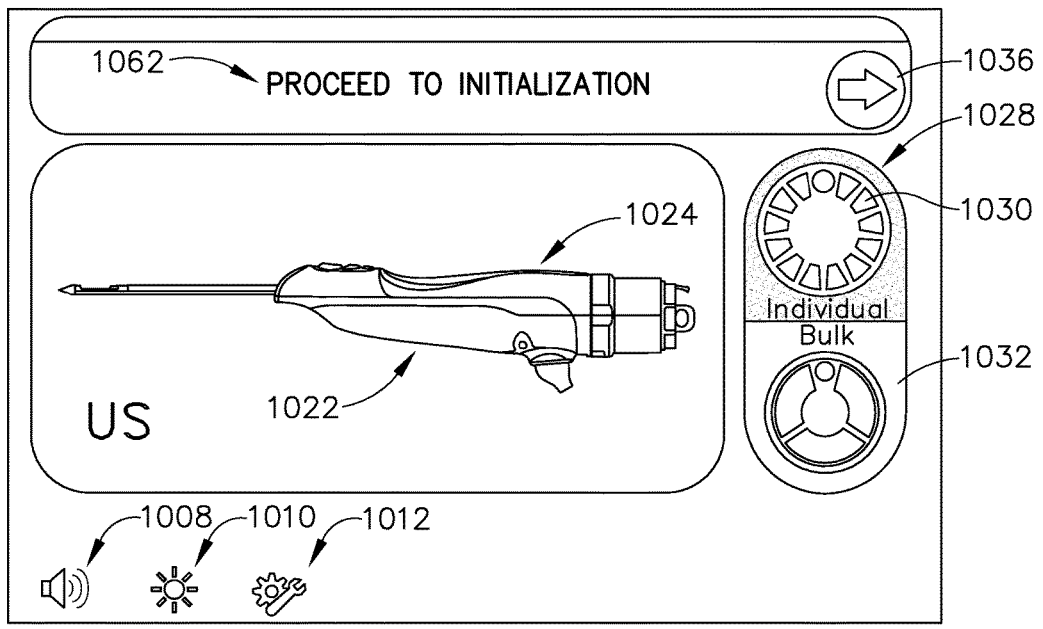
FIG. 33 depicts an exemplary fourth user interface screen for display on the vacuum control module of FIG. 1.

FIG. 33 shows screen (1060). Screen (1060) is substantially the same as screen (1020), except individual tray selector button (1030) is shown graphically as being engaged. In particular, individual tray selector button (1030) is shown as having a dark exterior to indicate that the user has selected individual tray selector button (1030). In contrast, bulk tray selector button (1032) remains as shown in FIG. 31. With individual tray selector button (1030) selected, the biopsy system is ready to be initialized as indicated by textual instruction (1062). The user may then initialize biopsy system (2) by pressing menu advance button (1036), which causes touchscreen (410) to transition to screen (1200), as will be described in greater detail below.

Figure 34:
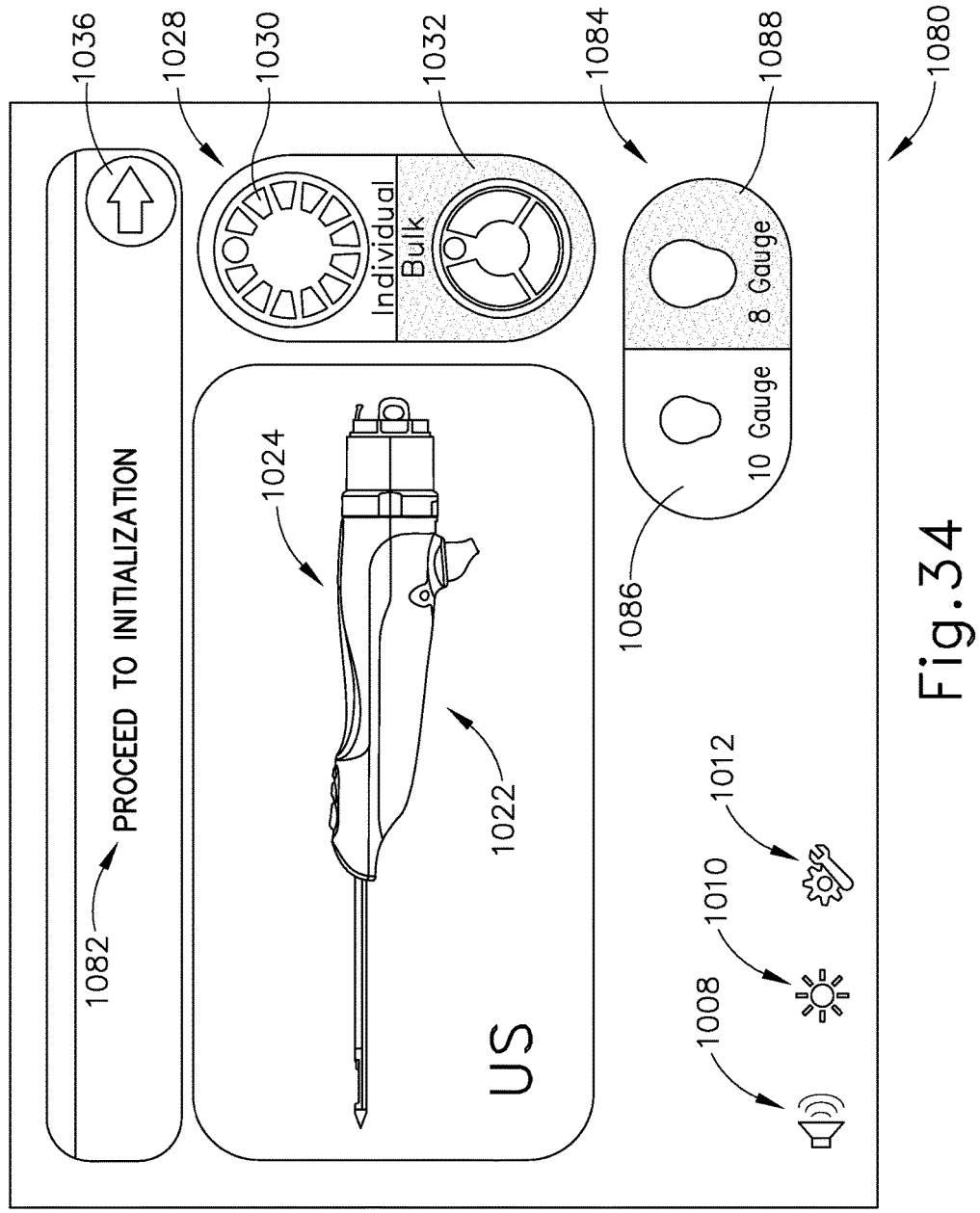
FIG. 34 depicts an exemplary fifth user interface screen for display on the vacuum control module of FIG. 1.

FIG. 34 shows screen (1080). Screen (1080) is substantially the same as screen (1020), except bulk tray selector button (1032) is shown graphically as being engaged. Additionally, screen (1080) includes a set of gauge selection buttons (1084). Bulk tray selector button (1032) is shown as having a dark exterior to indicate that the user has selected bulk tray selector button (1032). In contrast, individual tray selector button (1030) remains as shown in FIG. 31.

Gauge selection buttons (1084) includes a ten gauge selection button (1086) and an eight gauge selection button (1088). Each gauge selection button (1086, 1088) corresponds to a possible gauge size of needle (110). Accordingly, the user may select an appropriate gauge size corresponding to the actual gauge size of needle (110) that probe (100) is equipped with. The selected gauge selection button (1086, 1088) may be graphically indicated using a darkened outline around the selected gauge selection button (1086, 1088). In the present example, eight gauge selection button (1088) is shown as being selected, although ten gauge selection button (1086) may be similarly identified if selected. Although FIG. 34 specifically designates gauge selection buttons (1084) as corresponding to either a ten gauge or eight gauge needle (110), it should be understood that in other examples needle (110) may have any other gauge size and gauge selection buttons (1084) may be adjusted accordingly as will be apparent to those of ordinary skill in the art in view of the teachings herein.

With bulk tray selector button (1032) selected and the appropriate gauge selection button (1086, 1088) selected, the biopsy system is ready to be initialized as indicated by textual instruction (1082). The user may then initialize biopsy system (2) by pressing menu advance button (1036), which causes touchscreen (410) to transition to screen (2200), as will be described in greater detail below.

Figure 35:
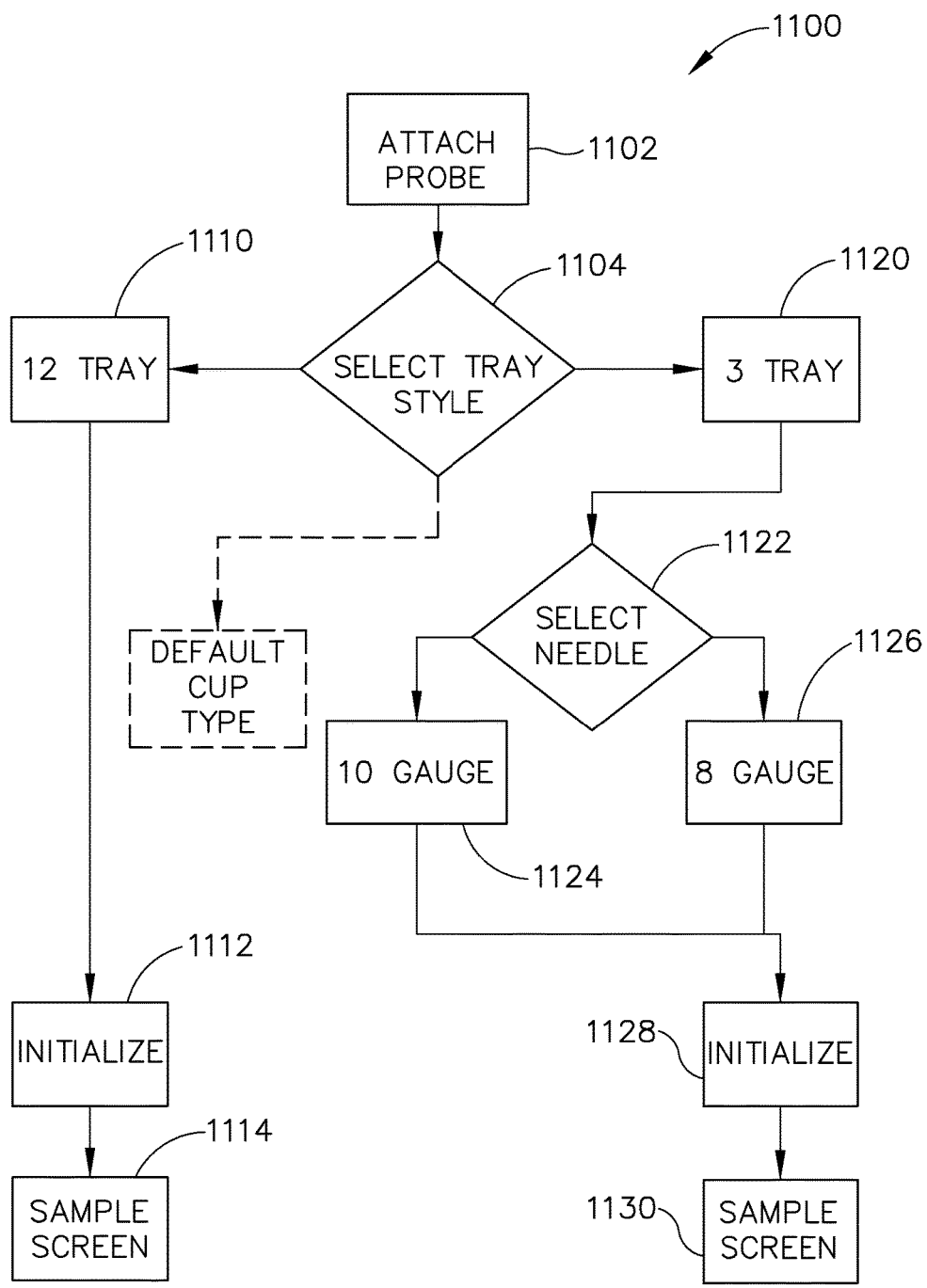
FIG. 35 depicts a flow chart showing an exemplary process for using the user interface screens of FIGS. 30-34.

FIG. 35 shows a flow chart of a setup procedure (1100) using screens (1000, 1020, 1040, 1060, 1080) described above for biopsy system (2). As can be seen, block (1102) indicates that the procedure begins when the user attaches probe (100) to holster (200) as described above with respect to screen (1000). Once probe (100) is attached, block (1104) indicates that the user may select the appropriate tissue sample assembly (300, 700) configured for either twelve tissue receiving trays (330) or three tissue receiving trays (730) as described above with respect to screen (1020). At this stage, a user may optionally select a default tissue sample assembly (300, 700) for future procedures as described above with respect to screen (1040). Such a step is indicated in FIG. 35 by block (1106), which is shown in phantom.

If use of tissue sample holder assembly (300) is selected, as indicated by block (1110), the user may proceed directly to initialization as indicated by block (1112) and as described above with respect to screen (1060). After initialization, touchscreen (410) may automatically transition to a sample screen (1200) corresponding to probe (100) when equipped with tissue sample holder assembly (300) as indicated in FIG. 35 by block (1114), and as will be described in greater detail below.

If use of tissue sample holder assembly (700) is selected, as indicated by block (1120), the user may further select the appropriate needle gauge of probe (100) as indicated by block (1122). In the present example, the user may select between either a ten gauge needle or an eight gauge needle, indicated by block (1124) and block (1126), respectively. Such a selection corresponds to screen (1080) described above. Regardless of the particular needle gauge selected, the user may start initialization as described above with respect to screen (1080) and as indicated by block (1028) in FIG. 35. Once initialization is complete, touchscreen (410) may automatically transition to a sample screen (2200) corresponding to probe (100) when equipped with tissue sample holder assembly (300) as indicated in FIG. 35 by block (1130), and as will be described in greater detail below.

B. Exemplary Sample Screen for Twelve Tray Tissue Sample Holder

Figure 36:
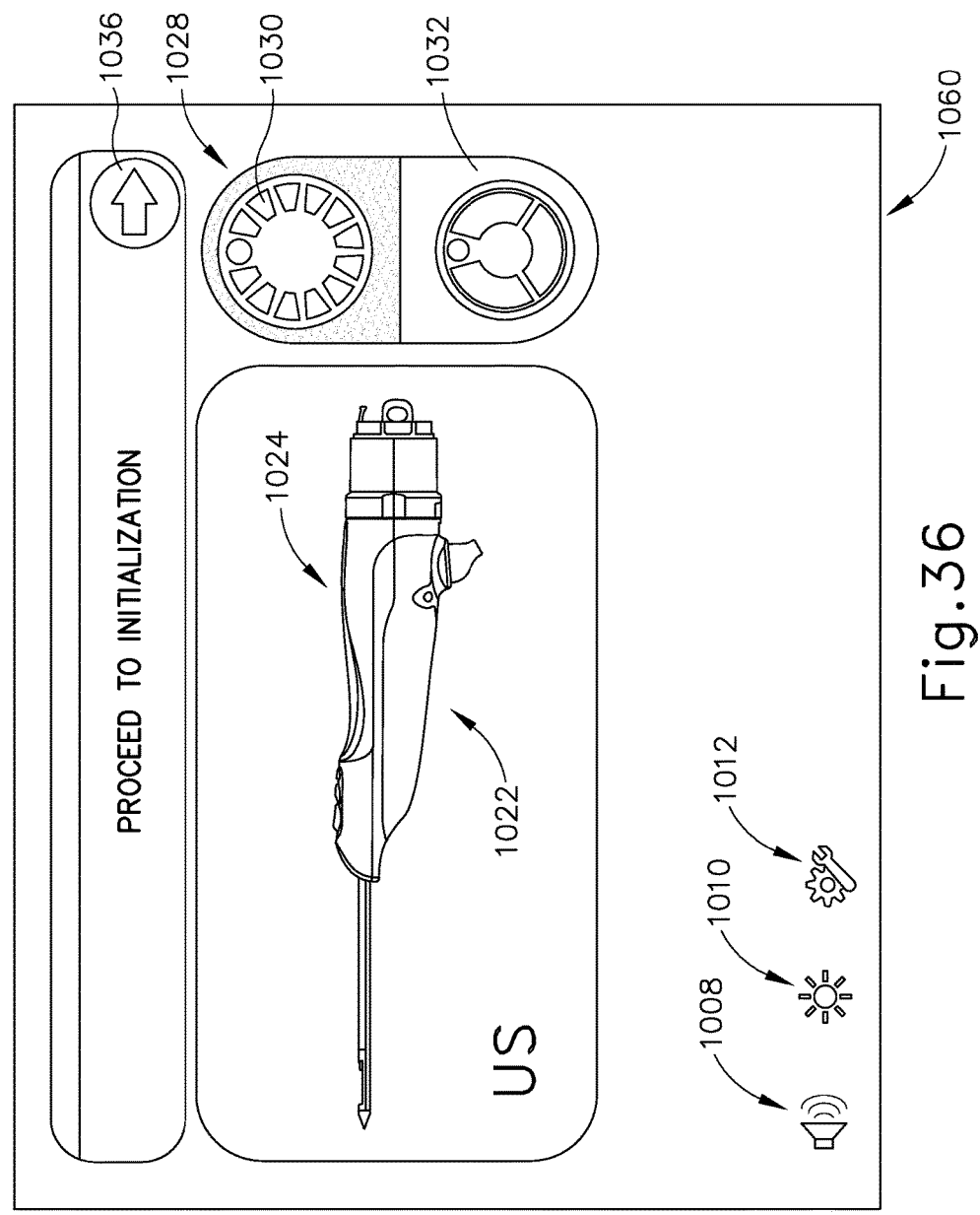
FIG. 36 depicts the fourth user interface screen of FIG. 33 in a second state.
Figure 37:
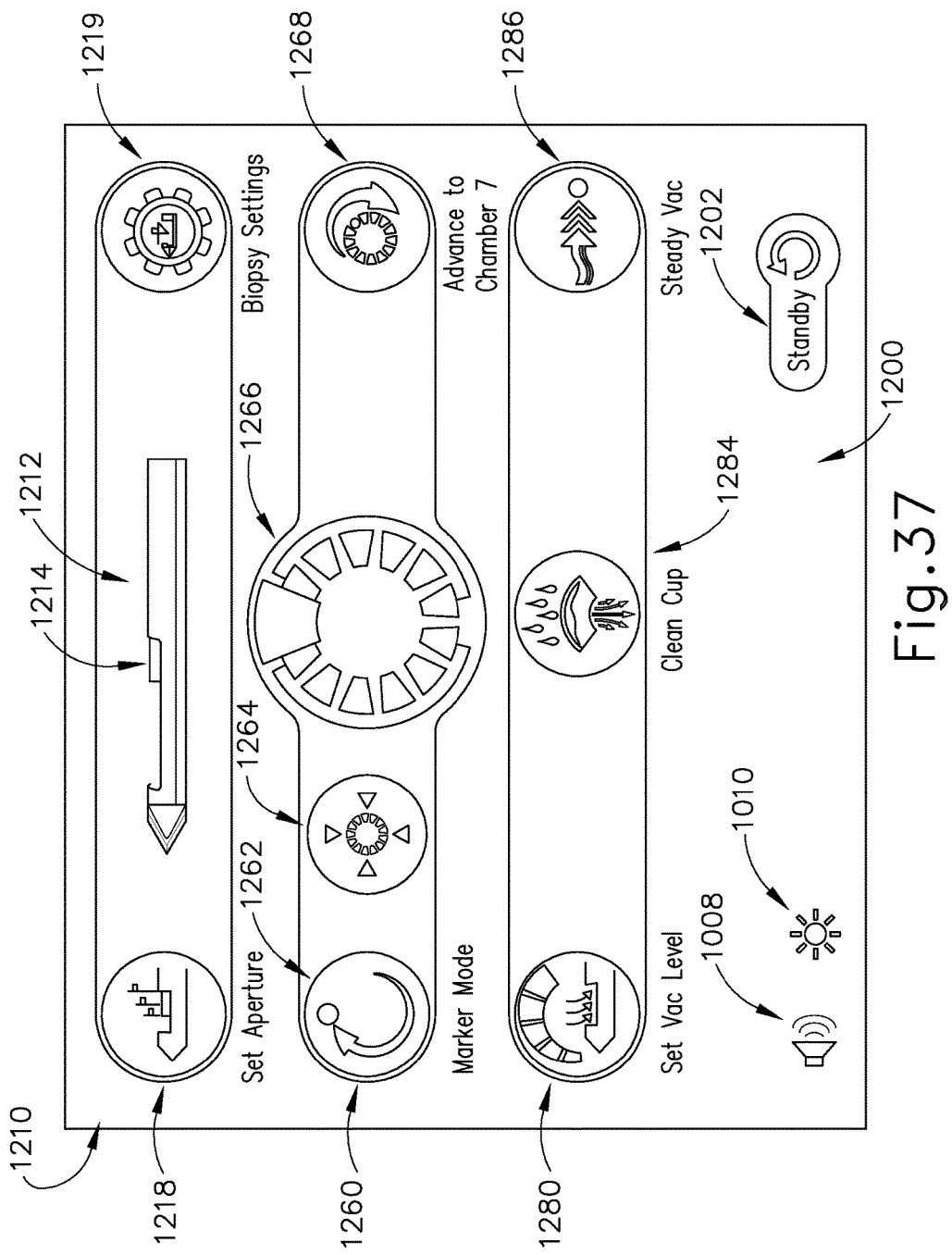
FIG. 37 depicts an exemplary sixth user interface screen for display on the vacuum control module of FIG. 1.

FIG. 36 shows screen (1060), as described above. As also described above, screen (1060) is displayed prior to initialization. To begin initialization, the user may press menu advance button (1036). Once initialization begins, touchscreen (410) automatically transitions to sample screen (1200), as shown in FIG. 37. Sample screen (1200) is configured to control probe (100) when probe (100) is equipped with tissue sample holder assembly (300). In some examples, initialization may require a predetermined amount of time. Accordingly, during initialization, sample screen (1200) may be darkened, dimmed, or otherwise blocked out to indicate to the user that the initialization process is still occurring. In some versions, such a predetermined amount of time may be five seconds. In some other versions, the predetermined amount of time may be longer, or shorter depending on a number of variables such as the particular control module (400) being used, the internal components of the particular control module (400) being used, the particular probe (100) being used, or any other variable as will be apparent to those of ordinary skill in the art.

Sample screen (1200) comprises a cutter control region (1210), a tissue sample holder control region (1260), and a vacuum control region (1280). Generally, regions (1210, 1260, 1280) group various biopsy system (2) functions according to whether the given function controls cutter (150), tissue sample holder (300), or the vacuum supplied by control module (400). Such functions of biopsy system (2) will be described in greater detail below in the context of each particular region (1210, 1260, 1280). It should be understood that although each function of biopsy system (2) is organized in a given way, in other examples alternative organizational schemes may be used. Sample screen (1200) also includes volume adjustment button (1008), brightness adjustment button (1010), and a standby button (1202). Standby button (1202) is generally operationally configured to place biopsy system (2) in standby mode and causes touchscreen (410) to transition to a standby screen (1290), as will be described in greater detail below.

1. Exemplary Cutter Interface Features

As shown in FIG. 37, cutter control region (1210) of screen (1200) includes a graphical representation (1212) of the distal end of needle (110), a graphical representation (1214) of cutter (150), a "set aperture" button (1218), and a biopsy settings button (1219).

Figure 38:
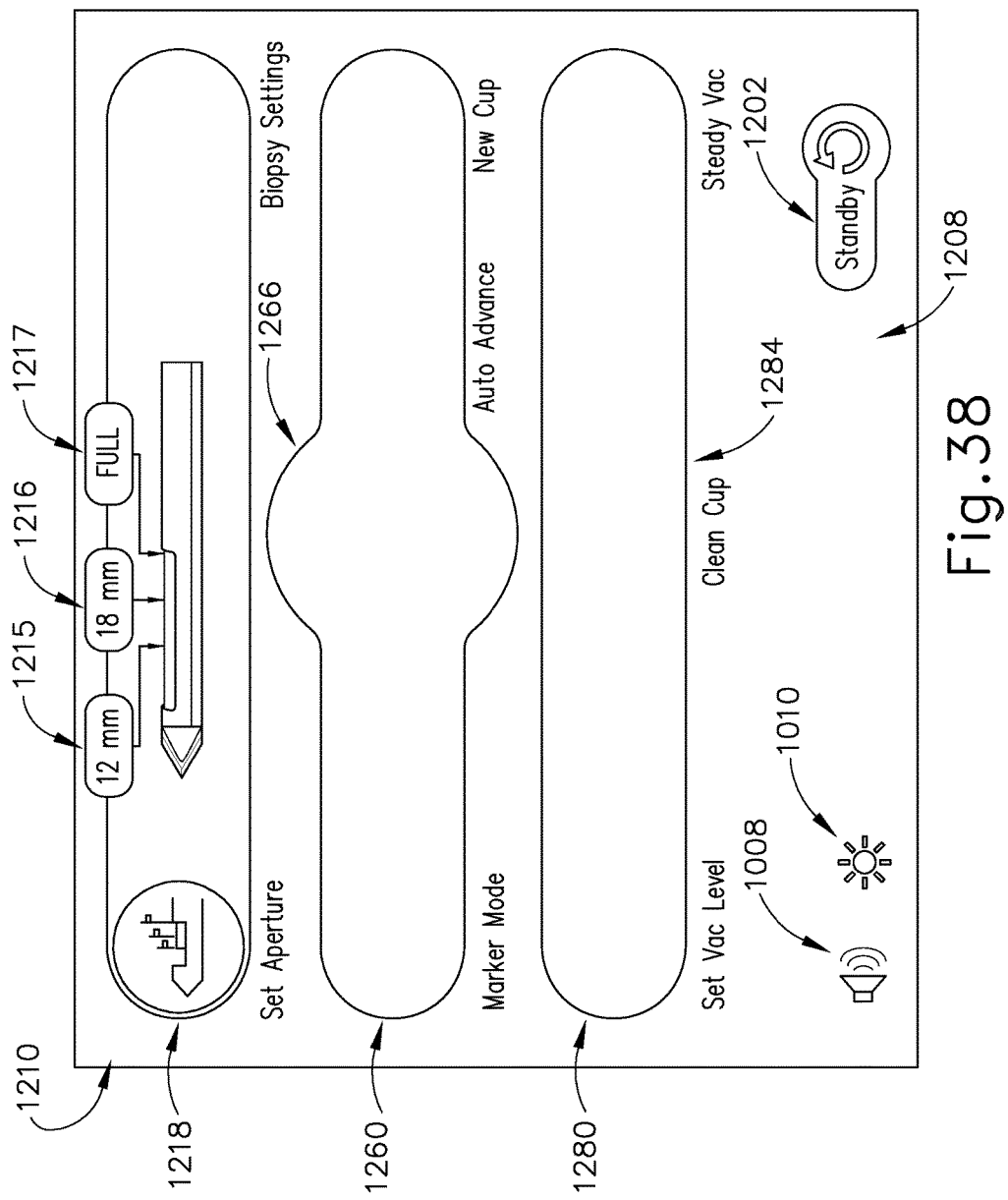
FIG. 38 depicts an exemplary seventh user interface screen for display on the vacuum control module of FIG. 1.

When the user taps on "set aperture" button (1218), touchscreen (410) transitions to screen (1208) shown in FIG. 38. Screen (1208) is generally similar to screen (1200), except that regions (1260, 1280) are dark, button (1219) is dark, and additional buttons (1215, 1216, 1217) appear over graphical representation (1212) of the distal end of needle (110). Buttons (1215, 1216, 1217) enable the user to define the effective length of lateral aperture (114) by restricting the position to which cutter (150) may proximally retract during operation of biopsy device (10). In other words, buttons (1215, 1216, 1217) enable the user to set the proximal-most position for distal edge (152) of cutter (150) during operation of biopsy device (10). In particular, button (1215) establishes a proximal-most position for distal edge (152) of cutter (150) during operation of biopsy device (10) whereby lateral aperture (114) is only opened 12 mm by cutter (150) before cutter (150) advances distally. Button (1216) establishes a proximal-most position for distal edge (152) of cutter (150) during operation of biopsy device (10) whereby lateral aperture (114) is only opened 18 mm by cutter (150) before cutter (150) advances distally. Button (1217) establishes a proximal-most position for distal edge (152) of cutter (150) during operation of biopsy device (10) whereby lateral aperture (114) is fully opened by cutter (150) before cutter (150) advances distally. Of course, these increments are mere examples, and any other suitable increments may be used. In the present example, biopsy system (2) will default to a fully opened aperture (114) setting in the event that the user does not select a different aperture size through screen (1208).

When a user taps a particular button (1215, 1216, 1217), screen (1208) provides feedback by positioning the graphical representation (1214) of cutter (150) such that the distal end of graphical representation (1214) corresponds with the position just selected by the user. This positioning of graphical representation (1214) may persist until the positioning is later changed by the user. For instance, FIG. 37 shows graphical representation (1214) in the 18 mm position during use of biopsy device (10).

By way of example only, system (2) may provide the above-described "variable aperture" functionality in accordance with at least some of the teachings of U.S. Pat. No. 7,517,322, entitled "Biopsy Device with Variable Side Aperture," issued Apr. 14, 2009, the disclosure of which is incorporated by reference herein; and/or in accordance with at least some of the teachings of U.S. Pub. No. 2008/0214955, the disclosure of which is incorporated by reference herein. In some versions, the graphical representation (1214) of cutter (150) as described above is provided in a first color; while a second graphical representation of cutter (150) is provided in a second color. This second graphical representation may show the actual position of cutter in real time.

Figure 39:
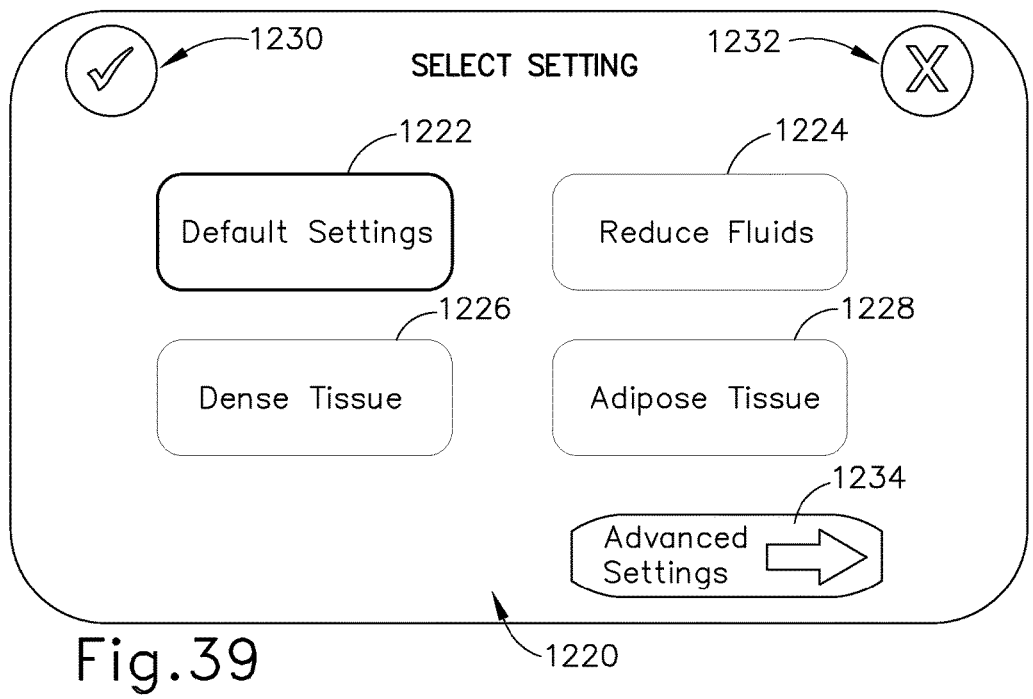
FIG. 39 depicts an exemplary eighth user interface screen for display on the vacuum control module of FIG. 1.

When the user taps biopsy settings button (1219) on screen (1200), touchscreen (410) transitions to screen (1220) shown in FIG. 39. Screen (1220) enables the user to select from four different pre-determined operational settings (1222, 1224, 1226, 1228) of biopsy system (2). Each pre-determined operational setting (1222, 1224, 1226, 1228) comprises specific biopsy system (2) settings that correspond to common clinical conditions. Such settings may include settings for vacuum duration, the amount of saline applied (if used), and/or the rate at which cutter (150) is advanced within needle (110). For instance, the user may tap a default settings button (1222) to set biopsy system (2) with pre-determined settings that may be desirable for general purposes. Similarly, the user may tap a reduce fluids button (1224) to set biopsy system (2) with pre-determined settings that may be desirable when the user wishes to minimize the amount of fluid such as saline that is delivered to the biopsy site during use of biopsy device (10). A dense tissue button (1226) may be tapped by the user to set biopsy system (2) with pre-determined settings that may be desirable for procedures where biopsy device (10) is used to biopsy relatively more dense tissue. Finally, an adipose tissue button (1228) may be tapped by the user to set biopsy system (2) with pre-determined settings that may be desirable for procedures where less dense adipose tissue may be encountered during a biopsy procedure.

Once the user selects a given pre-determined operational setting (1222, 1224, 1226, 1228), the user's selection is shown by darkening or changing the color of a given button (1222, 1224, 1226, 1228) for the selected setting. For instance, default settings button (1222) is shown as being selected in FIG. 39. Screen (1220) further includes a confirmation button (1230) and a cancelation button (1232). Upon tapping a given pre-determined operational setting (1222, 1224, 1226, 1228), the user may tap confirmation button (1230) to save the selection and return to sample screen (1200). Alternatively, the user may tap the cancelation button (1232) at any time to return to sample screen (1200) without saving a selected setting (1222, 1224, 1226, 1228) or without even making a selection.

Figure 40:
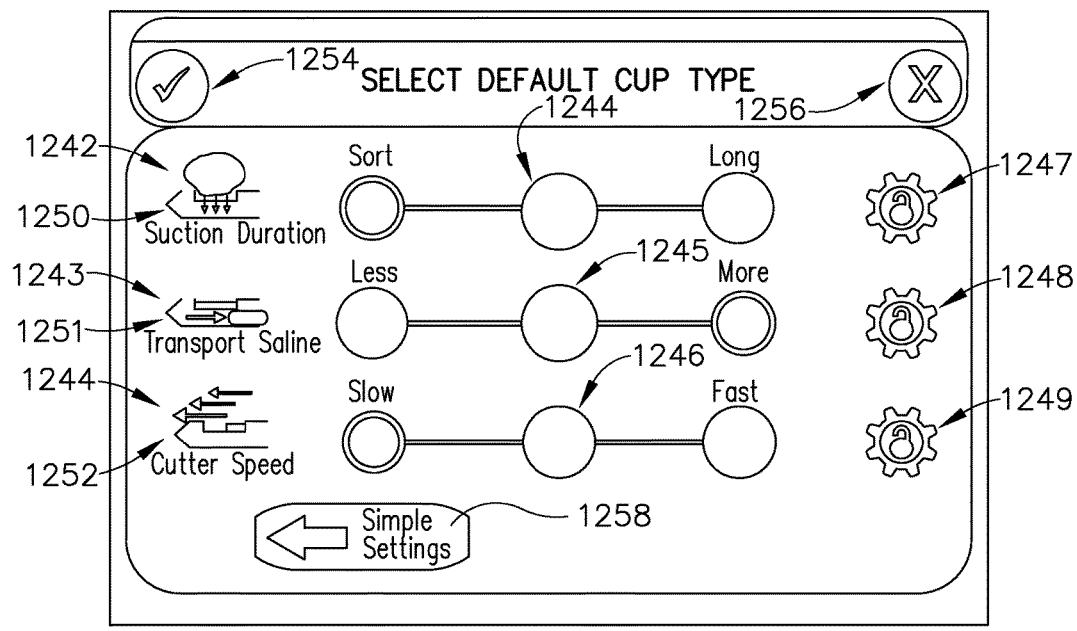
FIG. 40 depicts an exemplary ninth user interface screen for display on the vacuum control module of FIG. 1.

If the user desires additional control over the biopsy system (2) settings, the user may tap an advanced settings button (1234). When the user taps advanced settings button (1234), touchscreen (410) transitions to screen (1240) as shown in FIG. 40. Screen (1240) is configured to provide the user with more control over specific settings of biopsy system (2). In particular, screen (1240) includes a vacuum duration adjustment region (1241), a transport saline adjustment region (1242), and a cutter speed adjustment region (1243). Each region (1241, 1242, 1243) includes an adjustment slider (1244, 1245, 1246) and a lock setting button (1247, 1248, 1249). Each adjustment slider (1244, 1245, 1246) generally permits a user to adjust a given setting by sliding an indicator through a predetermined range for the given setting. Each lock setting button (1247, 1248, 1249) permits the user to store the selected setting in memory for subsequent uses of biopsy system (2) after a power down/power up cycle has occurred. Where lock setting button (1247, 1248, 1249) is not used, a given setting may remain at a given selected level until the power of biopsy system (2) is cycled off; or the given setting is adjusted to a new level.

Each region (1241, 1242, 1243) also includes a graphical representation (1250, 1251, 1253) to graphically communicate to the user what practical impact the given setting has on the biopsy procedure. For instance, vacuum duration adjustment region (1241) includes a graphical representation (1250) of tissue being pulled into lateral aperture (114) of needle (110). The amount of time during which vacuum is applied to pull tissue into lateral aperture may be adjusted by the user sliding his or her finger along the length of adjustment slider (1244). Once the user has adjusted the setting using adjustment slider (1244), the user may save the setting by tapping lock setting button (1247).

Transport saline adjustment region (1242) includes a graphical representation (1251) to indicate a tissue sample being transported through needle (110) using saline. The particular amount of saline used may be adjusted by the user by sliding his or her finger along the length of adjustment slider (1245). Once the user has adjusted the setting using adjustment slider (1245), the user may save the setting by tapping lock setting button (1248).

Cutter speed adjustment region (1243) includes a graphical representation (1252) to indicate speeds for advancement of cutter (150). Adjustment slider (1246) may enable selection from slow, standard, and fast speeds by the user sliding a finger along the length of adjustment slider (1246). By way of example only, the motor may rotate at approximately 20000 RPM during advancement of cutter (150) when slow speed is selected and at approximately 12000 RPM during retraction of cutter (150) when slow speed is selected. The motor may rotate at approximately 20000 RPM during advancement of cutter (150) when standard speed is selected and at approximately 20000 RPM during retraction of cutter (150) when standard speed is selected. The motor (244) may rotate at approximately 25000 RPM during advancement of cutter (150) when fast speed is selected and at approximately 25000 RPM during retraction of cutter (150) when fast speed is selected. Of course, any other suitable speeds may be used. The user may select one of these speeds based on the nature of the tissue being biopsied and/or based on other considerations. Once the user has adjusted the setting using adjustment slider (1246), the user may save the setting by tapping lock setting button (1248). It should be understood that the above-noted speed values are mere examples, such that any other suitable speeds may be provided.

Of course, as with other features of vacuum control module (400) described herein, vacuum duration adjustment region (1241), transport saline adjustment region (1242), and cutter speed adjustment region (1243) may be omitted if desired. For instance, some versions may provide the various settings described above with only a single setting.

Referring back to FIG. 39, screen (1220) further includes a confirmation button (1254) and a cancelation button (1256). Upon adjusting one or more settings using adjustment sliders (1244, 1245, 1246), the user may tap confirmation button (1254) to save the selection and return to sample screen (1200). Alternatively, the user may tap the cancelation button (1256) at any time to return to sample screen (1200) without saving a selected setting any adjustments made using adjustment sliders (1244, 1245, 1246). Should the user desire to return to screen (1208) for to instead use pre-determined settings (1222, 1224, 1226, 1228) described above, the user may do so by tapping a simple settings button (1258) thereby causing touchscreen (410) to transition back to screen (1208) without saving any setting adjustments made via adjustment sliders (1244, 1245, 1246).

It should be understood that the foregoing features relating to control of cutter (150) through touchscreen (410) are merely illustrative examples; and that they may be modified, substituted, supplemented, or omitted as desired. Various other features that may be used to provide control of cutter (150) through touchscreen (410) will be apparent to those of ordinary skill in the art in view of the teachings herein.

2. Exemplary Tissue Sample Holder Interface Features

Figure 41:
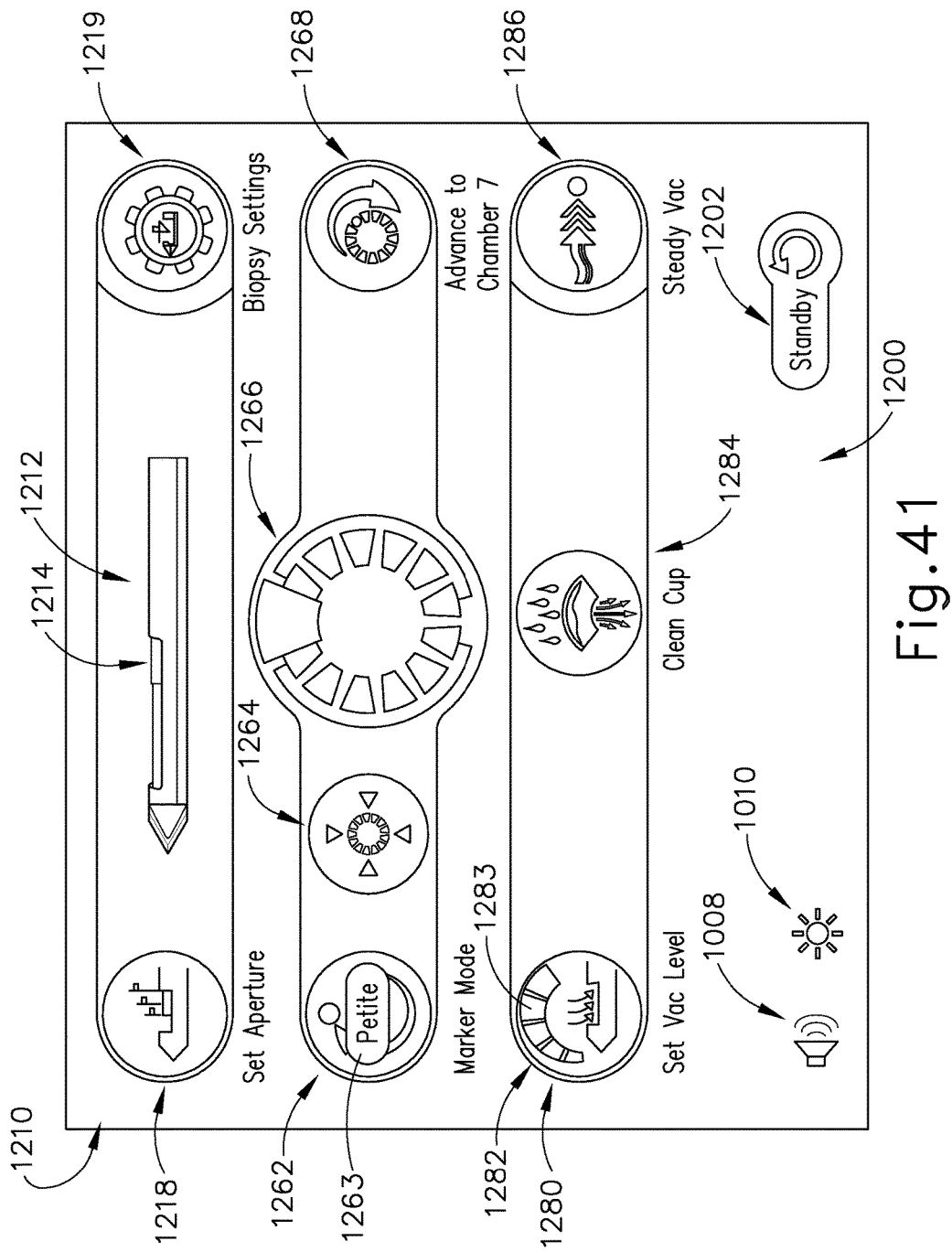
FIG. 41 depicts the sixth user interface screen of FIG. 37 in a second state.

Returning to FIG. 37, tissue sample holder control region (1260) of screen (1200) includes "marker mode" button (1262), a "set view position" button (1264), a graphical representation (1266) of tissue sample holder (300), and an "advance to chamber 7" button (1268). "Marker mode" button (1262) may be tapped by the user to advance tissue sample holder assembly (300) such that passage (313) is aligned with cutter (150). When tissue sample holder assembly (300) is advanced to such a position, the user may insert a marker delivery device through passage (313) and cutter lumen (151). In some instances, cutter (150) may be set via the set aperture button (1218) to be positioned such that distal edge (152) of cutter (150) is located between the proximal and distal ends of lateral aperture (114), such that lateral aperture (114) is only partially opened. In such instances, certain markers may not be compatible with biopsy device (10) because of the reduced opening of lateral aperture (114). Accordingly, "marker mode" button (1262) may include "petite" indicator (1263) as shown in FIG. 41 to remind the user to either only use a petite marker or to adjust cutter (150) via set aperture button (1218) to fully open lateral aperture (114).

Figure 42:
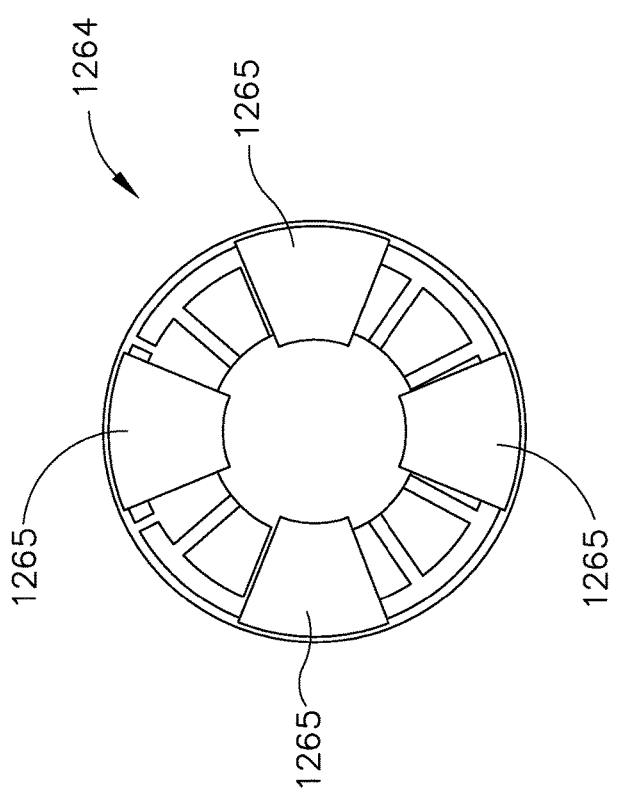
FIG. 42 depicts the sixth user interface screen of FIG. 37 in a third state.

"Set view position" button (1264) enables a user to select which side of tissue sample holder (300) will be designated for presentation of tissue samples each time a tissue sample is acquired. In particular, the user may select from four positions for tissue sample presentation—the 12 o'clock position, the 3 o'clock position, the 6 o'clock position, and the 9 o'clock position. As can be seen in FIG. 42, when the user taps "set view position" button (1264), screen (1200) may dim or otherwise indicate an inactive state while graphical representation (1266) remains fully illuminated. Additionally, selector buttons (1265) may appear. To select a given position for tissue sample presentation, the user may select a given selector button (1265) that corresponds to a given clock position. These positions correspond to the angular positions about the central axis of tissue sample holder (300). Of course, any other suitable position options may be provided. The user may select a position to provide the user with the best visibility of severed tissue samples, based on considerations such as the user's physical location in relation to biopsy device (10), the location of adjacent equipment, etc. It should be understood that one of the above-listed positions (or some other position), such as the 12 o'clock position, may be automatically selected by default, in the event that the user does not affirmatively select a presentation position through set view position" button (1264). Further details of tissue sample presentation are described in greater detail below. Additional details relating to examples of tissue sample presentation are described in U.S. Pub. No. 2008/0214955, the disclosure of which is incorporated by reference herein.

Figure 43:
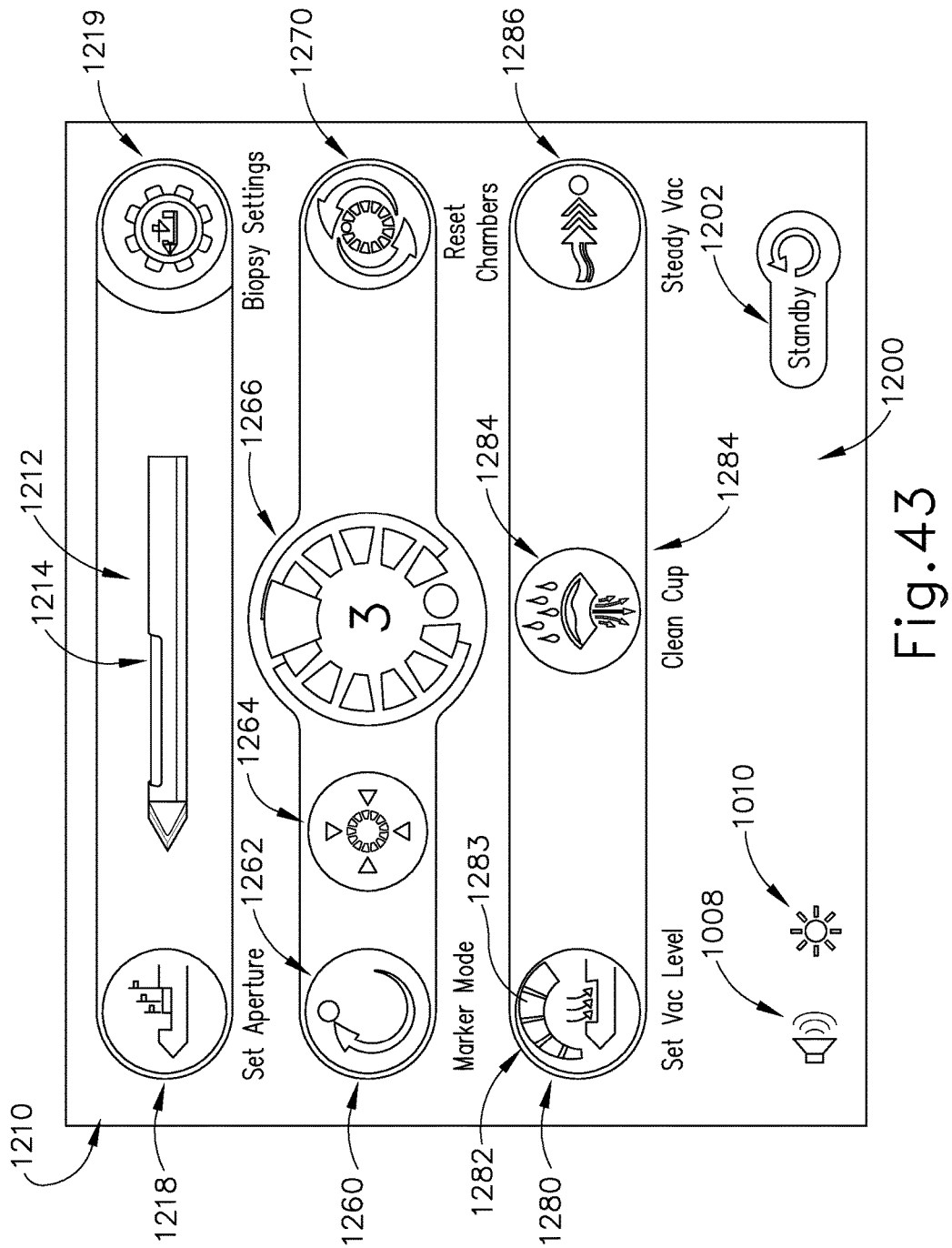
FIG. 43 depicts the sixth user interface screen of FIG. 37 in a fourth state.

During operation of biopsy device (10), tissue sample holder control region (1260) of screen (1200) as shown in FIG. 37 indicates the successive filling of each chamber (346) in the graphical representation (1266) of tissue sample holder (300). In particular, FIG. 43 shows the first six chambers (346) as being full, by illuminating those first six chambers in graphical representation (1266) in a color that is different from the color used to illuminate the rest of the chambers in graphical representation (1266). Thus, as each tissue sample is acquired, the chambers in graphical representation (1266) successively change colors to indicate the filling of tissue sample holder assembly (300). In instances where the "advance to chamber 7" button (1268) is used, tissue sample holder assembly (300) may skip the first six chambers (346). Once "advance to chamber 7" is tapped, those skipped chambers (346) may be illuminated in yet a different color in graphical representation (1266). In other words, graphical representation (1266) may show available chambers in one color, occupied chambers in another color, and skipped chambers in yet another color.

As noted above, in some instances the user may wish to skip chambers (346) in tissue sample holder assembly (300). To that end, the user may tap "advance to chamber 7" button (1268) to rotate manifold (310) in an increment corresponding to six chambers (346) in one motion. In other words, tapping the "advance to chamber 7" button (1268) will cause manifold (310) to index the seventh chamber (346) of tissue sample holder assembly (300) with lumen (151) of cutter (150), regardless of which chamber (346) was previously aligned with lumen (151) of cutter (150). Such a feature may be desirable when a user has removed a first tray (330) (providing the first six chambers (346)) from manifold (310) in the middle of a biopsy procedure where less than six tissue samples have been acquired; and the user wishes to continue the biopsy procedure beginning with the seventh chamber (346) (which would be the first chamber (346) of the second tray (330)). In some versions, tapping "advance to chamber 7" button (1268) will automatically rotate manifold (310) incrementally to skip a single chamber (346) instead of six. For instance, this may be desirable in instances where the first tissue sample is deposited in the chamber (346) at the 5 o'clock position, etc.

There may also be occasions during a biopsy procedure where the user wishes to remove tissue sample holder (300) from probe (100) and couple a new tissue sample holder (300) with probe (100) (e.g., while needle (110) is still inserted in the patient's breast) for further acquisition of tissue samples. When a user does this, the user may tap "reset chambers" button (1270) as shown in FIG. 43. The "reset chambers" button (1270) becomes visible on screen (1200) after "advance to chamber 7" button (1268) has been tapped. In the present example, "reset chambers" button (1270) is shown as replacing "advance to chamber 7" button (1268). In some other versions, "reset chambers" button (1270) may appear separately. When the user taps "reset chambers" button (1270), vacuum control module (400) resets graphical representation (1266) of tissue sample holder (300) to show all chambers (346) being empty.

It should be understood that the foregoing features relating to control of tissue sample holder (300) through touchscreen (410) are merely illustrative examples; and that they may be modified, substituted, supplemented, or omitted as desired. Various other features that may be used to provide control of tissues sample holder (300) through touchscreen (410) will be apparent to those of ordinary skill in the art in view of the teachings herein.

3. Exemplary Vacuum Interface Features

Figure 44:
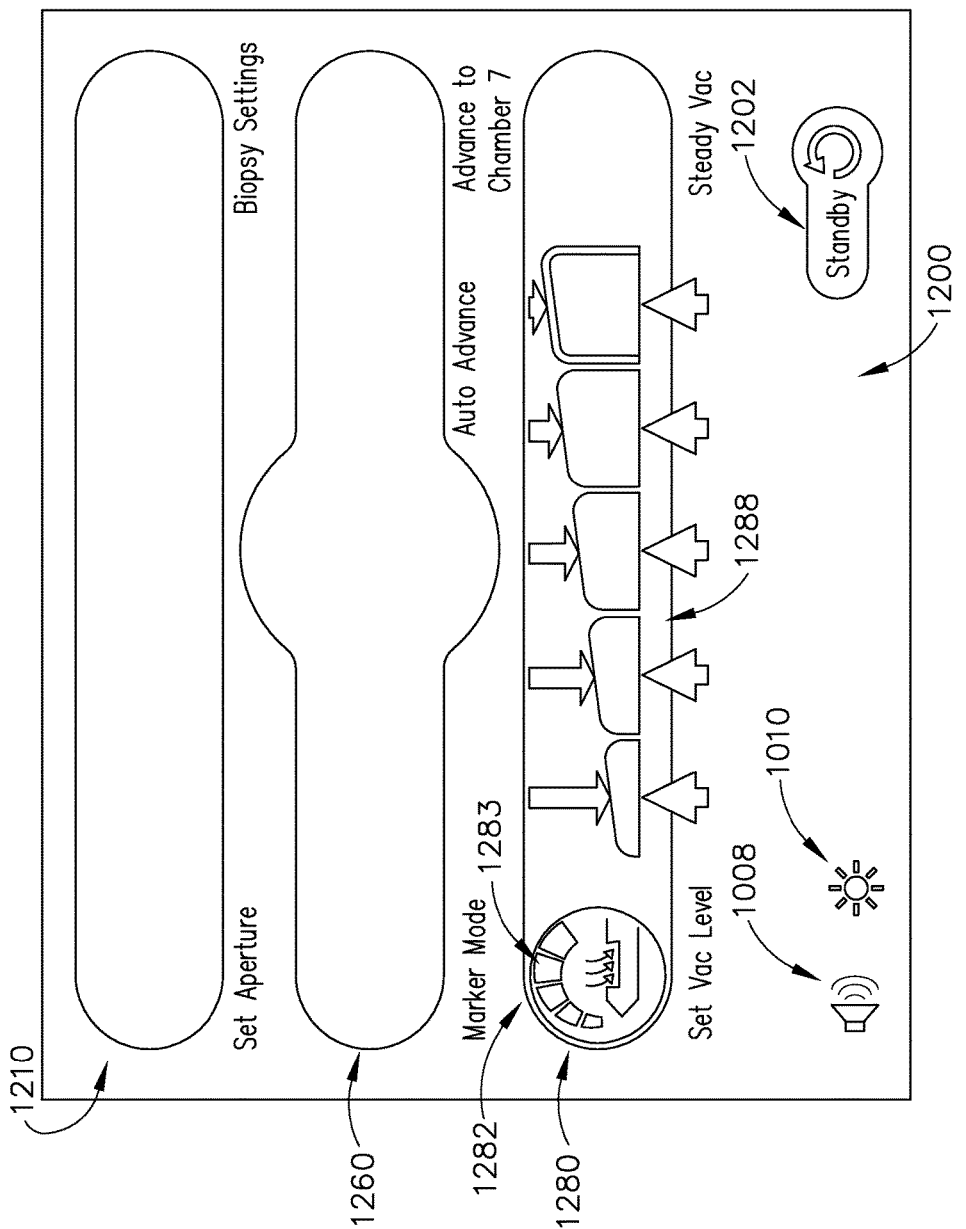
FIG. 44 depicts the sixth user interface screen of FIG. 37 in a fifth state.

Still referring to FIG. 37, vacuum control region (1280) of screen (1200) includes a "set vac level" button (1282), a "clean cup" button (1284), and a "steady vac" button (1286). When a user taps "set vac level" button (1282), screen (1200) darkens as shown in FIG. 44 such that regions (1210, 1260) are dark and buttons (1284, 1286) are dark. Additionally, a set of bars (1288) appears that generally increase in length from left to right. Button (1282) enables the user to select an amount of vacuum provided by the vacuum pump. In particular, the user may tap a particular bar in the set of bars (1288) to select the vacuum level. Alternatively, the user may slide his or her finger along bars (1288) until arriving at the desired vacuum level, then pull his or her finger away from touchscreen (410). The particular level of vacuum is illustrated graphically by the increasing length of bars (1288) from left to right. In other words, the further the user selects a bar to the right, the higher the level of vacuum. Once a desired level of vacuum has been selected, the user may return screen (1200) to the view shown in FIG. 37 by tapping "set vac level" button (1282). As shown in FIG. 37, "set vac level" button (1282) persistently displays the selected vacuum level through a set of bars (1283) integrated into "set vac level" button (1282).

Referring again to FIG. 37, the user may select "clean cup" button (1284) to initiate cleaning of any tissue contained within tissue sample holder assembly (300). For instance, when the user taps "clean cup" button (1284), biopsy system (2) may automatically deliver saline to tissue sample holder assembly (300). Next, biopsy system (2) may initiate a vacuum in tissue sample holder assembly (300) to draw the saline through any tissue samples and out of tissue sample holder assembly (300). This combination of saline and vacuum may effectively flush blood and/or other debris from the tissue samples, thereby promoting easier visualization of the tissue samples. It should be understood that in some examples, "clean cup" button (1284) may be separated into two buttons such that one button is configured to deliver saline to tissue sample holder assembly (300) while another button is configured to initiate vacuum in tissue sample holder assembly (300). Of course, as with other features described herein, "clean cup" button (1284) may be omitted if desired.

The user may tap "steady vac" button (1286) to initiate a "steady vac" cycle. The user may subsequently tap button (1286) again to stop the "steady vac" cycle. In addition or in the alternative, the "steady vac" cycle may automatically cease when the user activates biopsy device (10) to extract a tissue sample or provides some other user input. The "steady vac" cycle may be used in instances it may be desirable to provide continuous suction at a biopsy site. For instance, after obtaining a few biopsy samples, a user may wish to extract tray (330) from manifold (310) to inspect tissue samples therein. The user may wish to leave needle (110) inserted in the patient's breast during this time, particularly if the user intends to obtain more biopsy samples. Biopsy device (10) thus remains substantially idle during this time. It may be desirable to provide some sort of pneumatic flow within biopsy device (10) during this idle time. By way of example only, it may be desirable to provide suction at the biopsy site in instances where the biopsy site is bleeding significantly, such that the suction will draw away the blood. In addition or in the alternative, maintaining a pneumatic flow through biopsy device (10) may reduce the likelihood of blood and/or other bodily fluids coagulating on certain internal components of probe (100); and/or may reduce the likelihood of a hematoma forming at the biopsy site.

It should be understood that the foregoing features relating to control of vacuum through touchscreen (410) are merely illustrative examples; and that they may be modified, substituted, supplemented, or omitted as desired. Various other features that may be used to provide control of vacuum through touchscreen (410) will be apparent to those of ordinary skill in the art in view of the teachings herein. Similarly, various other features of system (2) that may be controlled through touchscreen (410), and ways in which such features may be controlled through touchscreen (410), will be apparent to those of ordinary skill in the art in view of the teachings herein.

4. Exemplary Standby Mode

Figure 45:
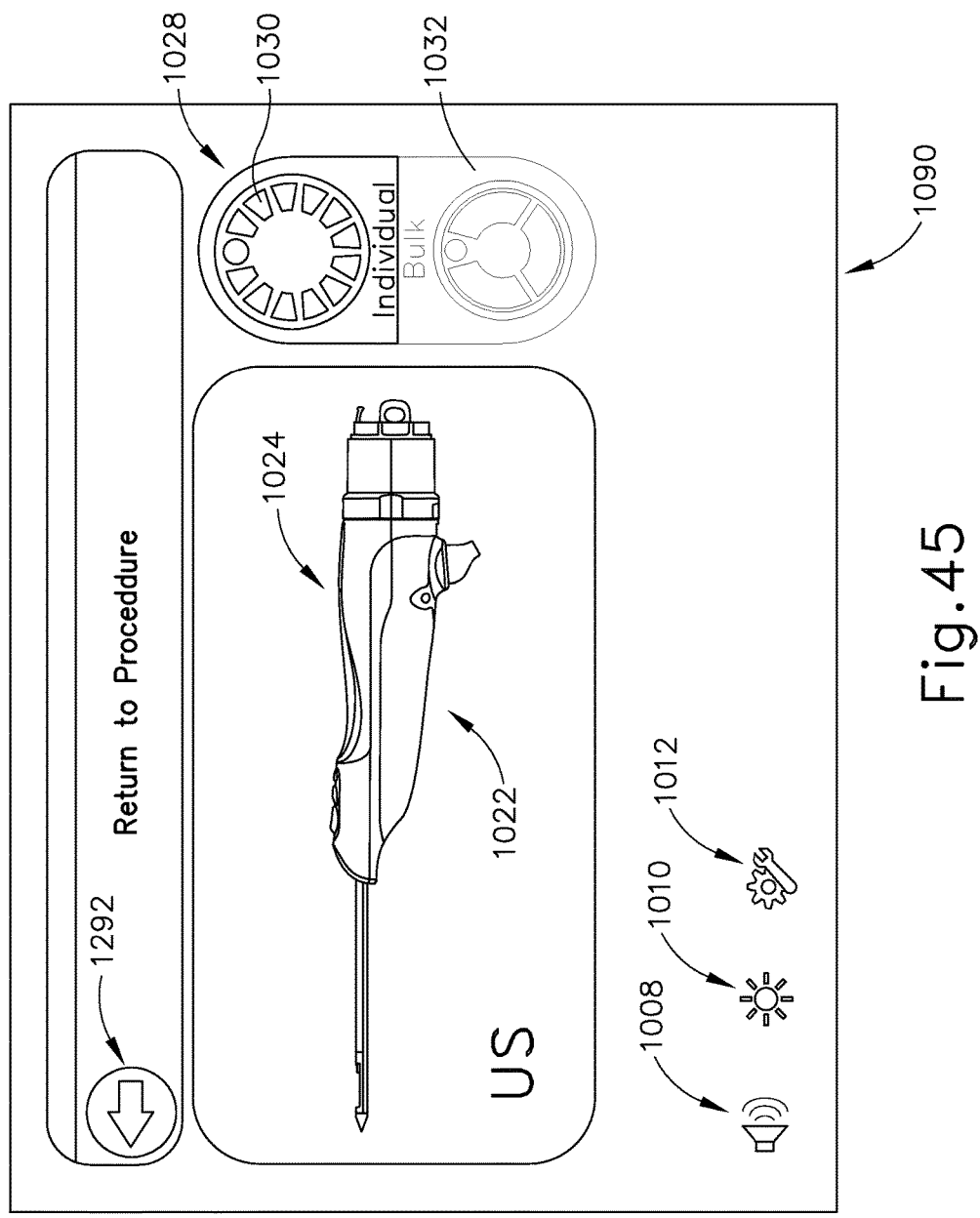
FIG. 45 depicts an exemplary tenth user interface screen for display on the vacuum control module of FIG. 1.

As described above, sample screen (1200) includes a standby button (1202). Standby button (1202) may be tapped by the user to enter standby model. In particular, when standby button (1202) is tapped, touchscreen (410) transitions from to screen (1290), thereby entering standby mode. As can be seen in FIG. 45, screen (1290) is substantially similar to screen (1060) described above, except screen (1290) includes a back button (1292) that permits the user to return to an active mode of biopsy system (2) where sample screen (1200) is displayed by touchscreen (410). It should be understood that other screens may also include standby button (1202); or that standby button (1202) may simply be omitted.

5. Exemplary Operation of Biopsy System in "Individual" Mode

Figure 46:
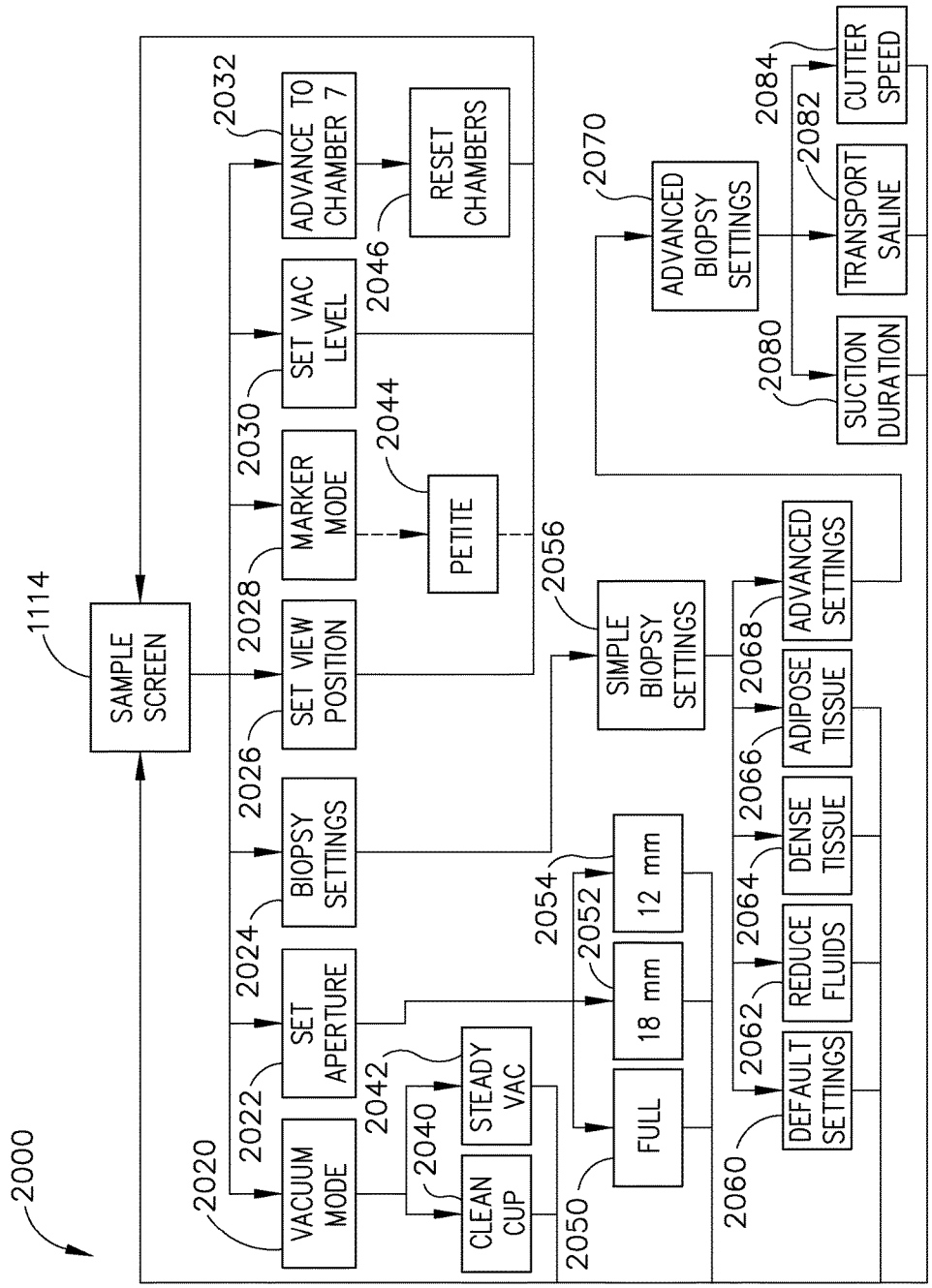
FIG. 46 depicts an exemplary process for using the user interface screens of FIGS. 36-45.

FIG. 46 shows the operational states of control module (400), described above, in a flow chart (2000). It should be understood that flow chart (2000) is a continuation of flow chart (1100) shown in FIG. 35. In particular, flow chart (1100) ends with block (1114) when tissue sample holder assembly (300) is attached to probe (100). As described above, block (1114) corresponds to sample screen (1200), described above. Sample screen (1200) is similarly indicated by block (1114) in FIG. 46, with flow chart (2000) beginning at block (1114) in FIG. 46. As described above, screen (1200) provides several potential options for the user to proceed. For instance, the user may set the aperture defined by cutter (150) relative to lateral aperture (114) by taping set aperture button (1218) as indicated by block (2022). In such instances, buttons (1215, 1216, 1217) may be used to select between a plurality of different aperture settings as indicated by blocks (2050, 2052, 2054). Once a given aperture size has been selected, a user may return to sample screen (1200) as indicated by block (1114).

The user may enter biopsy settings screen (1220) by pressing biopsy settings button (1219) as indicated by blocks (2024, 2056). Once touchscreen (410) has been transitioned to screen (1220) as indicated by block (2056), the user may select pre-determined settings (1222, 1224, 1226, 1228) as indicated by blocks (2060, 2062, 2064, 2066). Alternatively, the user may elect to enter screen (1240) to adjust advanced biopsy settings as indicated by block (2070). As described above, the user may selectively adjust vacuum duration, transport saline, and cutter speed using adjustment sliders (1244, 1245, 1246) as indicated by blocks (2080, 2082, 2084). Regardless of which screen (1220, 1240) is used by the user, the user may return to sample screen (1200) as indicated by block (1114) once any desired changes to the settings are made.

The user may initiate marker mode by pressing "marker mode" button (1262) as indicated by block (2028). Illumination of "petite" indicator (1263) is indicated by block (2044). Regardless of whether "petite" indicator (1263) is illuminated, sample screen (1200) remains displayed when biopsy system (2) is in marker mode, as described above.

From sample screen (1200) the user may also press "set view position" button (1264) as indicated by block (2026). As can be seen, touchscreen (410) continues to display sample screen (1200) when "set view position" button (1264) is pressed. However, as described above, graphical representation (1266) of tissue sample holder assembly (300) may become highlighted relative to the rest of sample screen (1200) (e.g., by other features of sample screen (1200) being dimmed or darkened). Selector buttons (1265) may also appear so that the user may select the desired view position as described above.

The user may also press "advance to chamber 7" button (1268) from sample screen (1200) as indicated by block (2032). As described above, pressing "advance to chamber 7" button (1268) causes tissue sample holder assembly (300) to advance to the seventh chamber (346). Block (2046) indicates, as was described above, that "reset chambers" button (1270) appears after "advance to chamber 7" button (1268) has been pressed, thereby permitting the user to re-set graphical representation (1266).

The user may also set the level of vacuum of the biopsy system (2) from sample screen (1200) by pressing "set vac level" button (1282) as indicated by block (2030). As described above, when "set vac level" button (1282) is pressed, sample screen (1200) remains on touchscreen (410), yet various features are darkened or dimmed to highlight a set of bars (1288) that permit adjustment of the vacuum level. Once the desired level of vacuum has been set, the user can re-activate the rest of sample screen (2010) by pressing "set vac level" button (1282) again.

Block (2020) indicates that two vacuum modes may be activated from sample screen (1200). For instance, block (2040) indicates that "clean cup" button (1284) may be pressed to activate the procedure for providing saline and vacuum to tissue sample holder assembly (300) described above. Block (2042) indicates that steady vac mode may be activated by pressing "steady vac" button (1286). Regardless of whether "clean cup" button (1284) or "steady vac" button (1286) is pressed, it should be understood that in both instances sample screen remains visible on touchscreen (410).

Of course the foregoing operational sequences are merely illustrative examples. Various other operational sequences may be provided in addition to or in lieu of those described above. Other suitable operational sequences will be apparent to those of ordinary skill in the art in view of the teachings herein.

C. Exemplary Sample Screen for Three Tray Tissue Sample Holder

Figure 47:
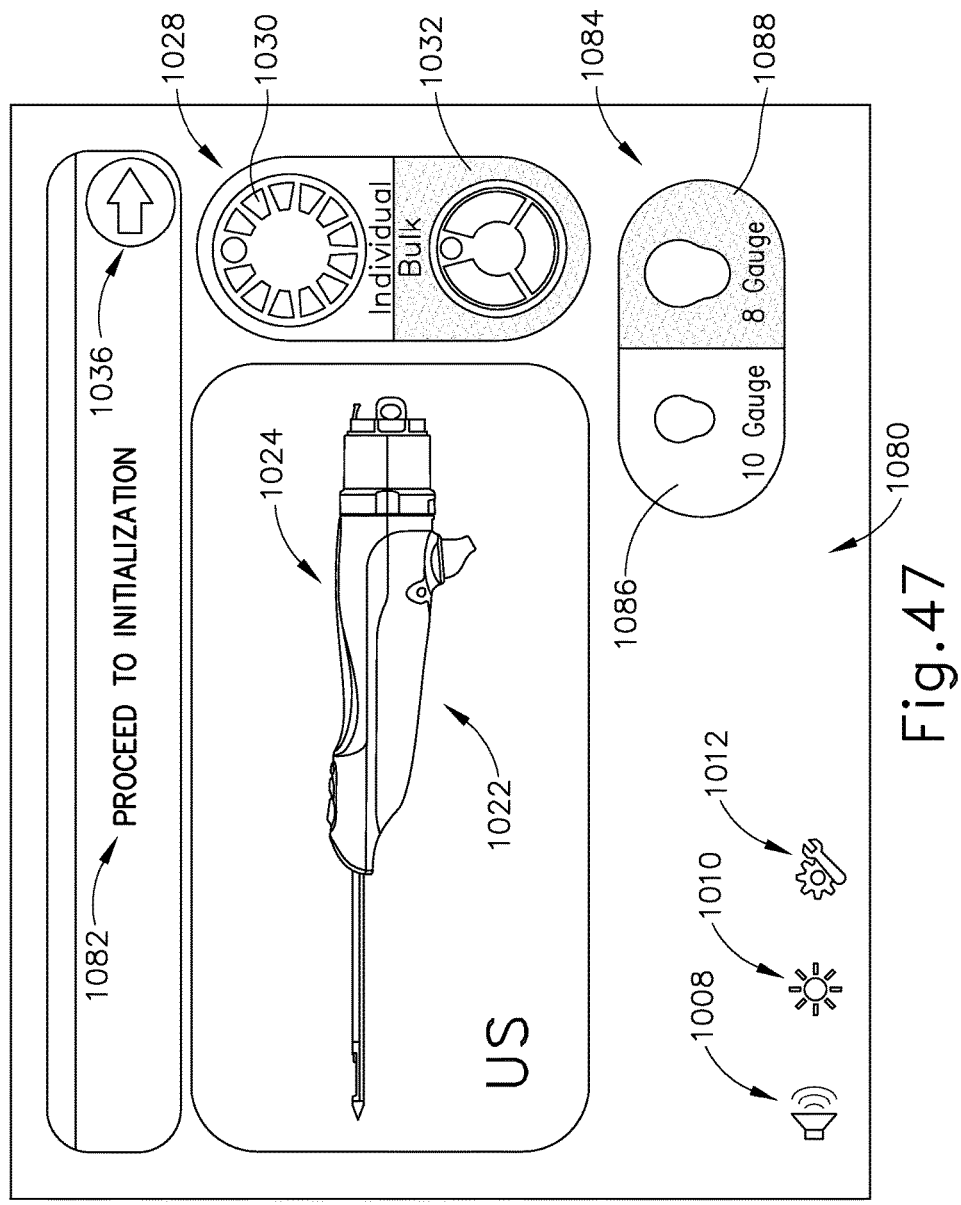
FIG. 47 depicts the fifth user interface screen of FIG. 34 in a second state.
Figure 48:
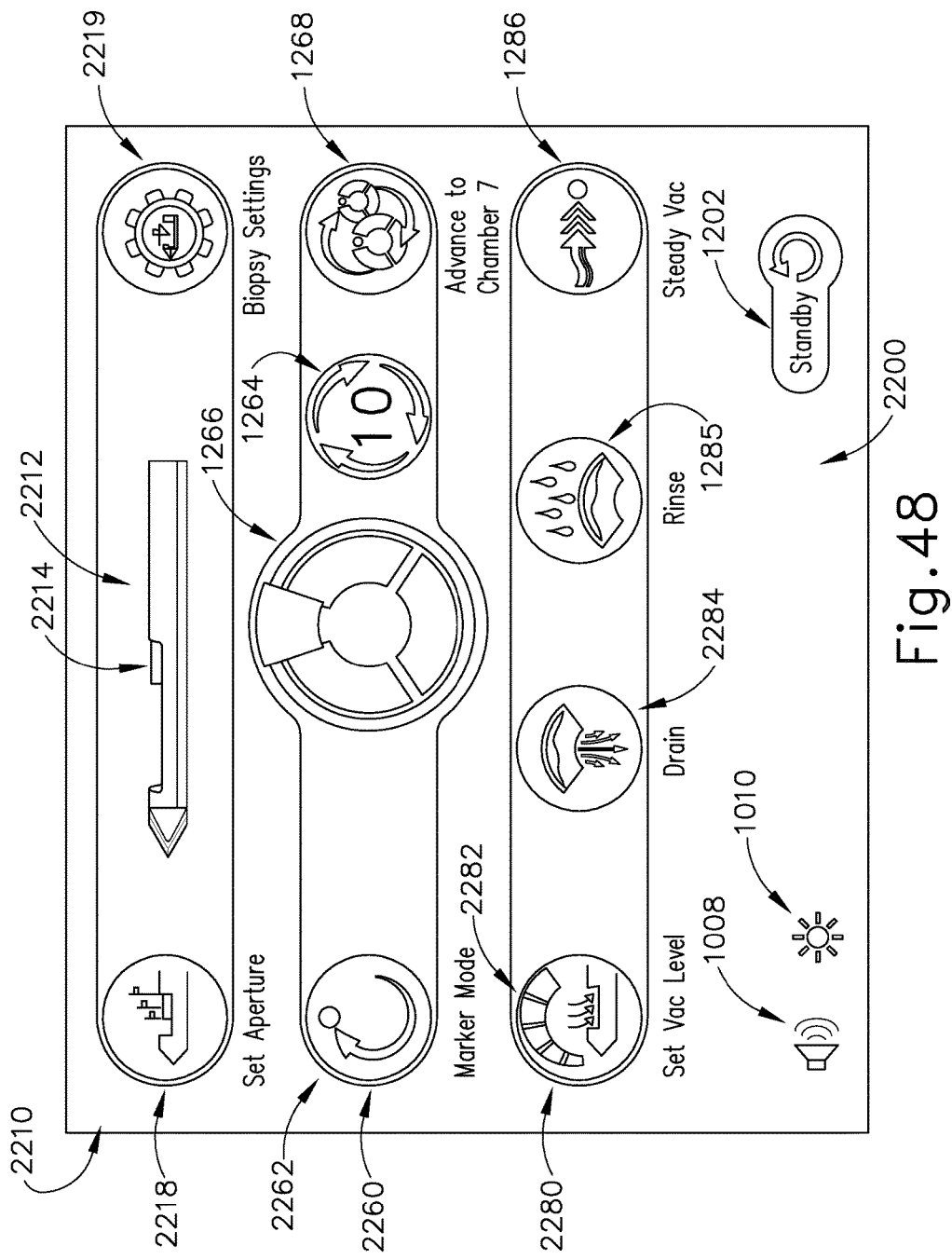
FIG. 48 depicts an exemplary eleventh user interface screen for display on the vacuum control module of FIG. 1.

FIG. 47 shows screen (1080), as described above. As also described above, screen (1080) is displayed prior to initialization. At this stage, a bulk sampling mode is selected via bulk tray selector button (1032), such that tissue sample holder (700) is being used with biopsy device (100). To begin initialization, the user may press menu advance button (1036). Once initialization begins, touchscreen (410) automatically transitions to sample screen (2200), as shown in FIG. 48. Sample screen (2200) is configured to control probe (100) when probe (100) is equipped with tissue sample holder assembly (700). It should be understood that sample screen (2200) is substantially the same as sample screen (1200) described above, except where otherwise noted herein.

Sample screen (2200) comprises a cutter control region (2210), a tissue sample holder control region (2260), and a vacuum control region (2280). Generally, regions (2210, 2260, 2280) are similar to regions (1210, 1260, 1280) described above. It should be understood that although each function of biopsy system (2) is organized in a particular way in this example, alternative organizational schemes may be used in other examples. Sample screen (2200) also includes volume adjustment button (1008), brightness adjustment button (1010), and a standby button (2202). Standby button (2202) is generally operationally configured to place biopsy system (2) in standby mode and causes touchscreen (410) to transition to a standby screen (2290), as will be described in greater detail below.

1. Exemplary Cutter Interface Features

As shown in FIG. 48, cutter control region (2210) of screen (2200) includes a graphical representation (2212) of the distal end of needle (110), a graphical representation (2214) of cutter (150), a "set aperture" button (2218), and a biopsy settings button (2219).

Figure 49:
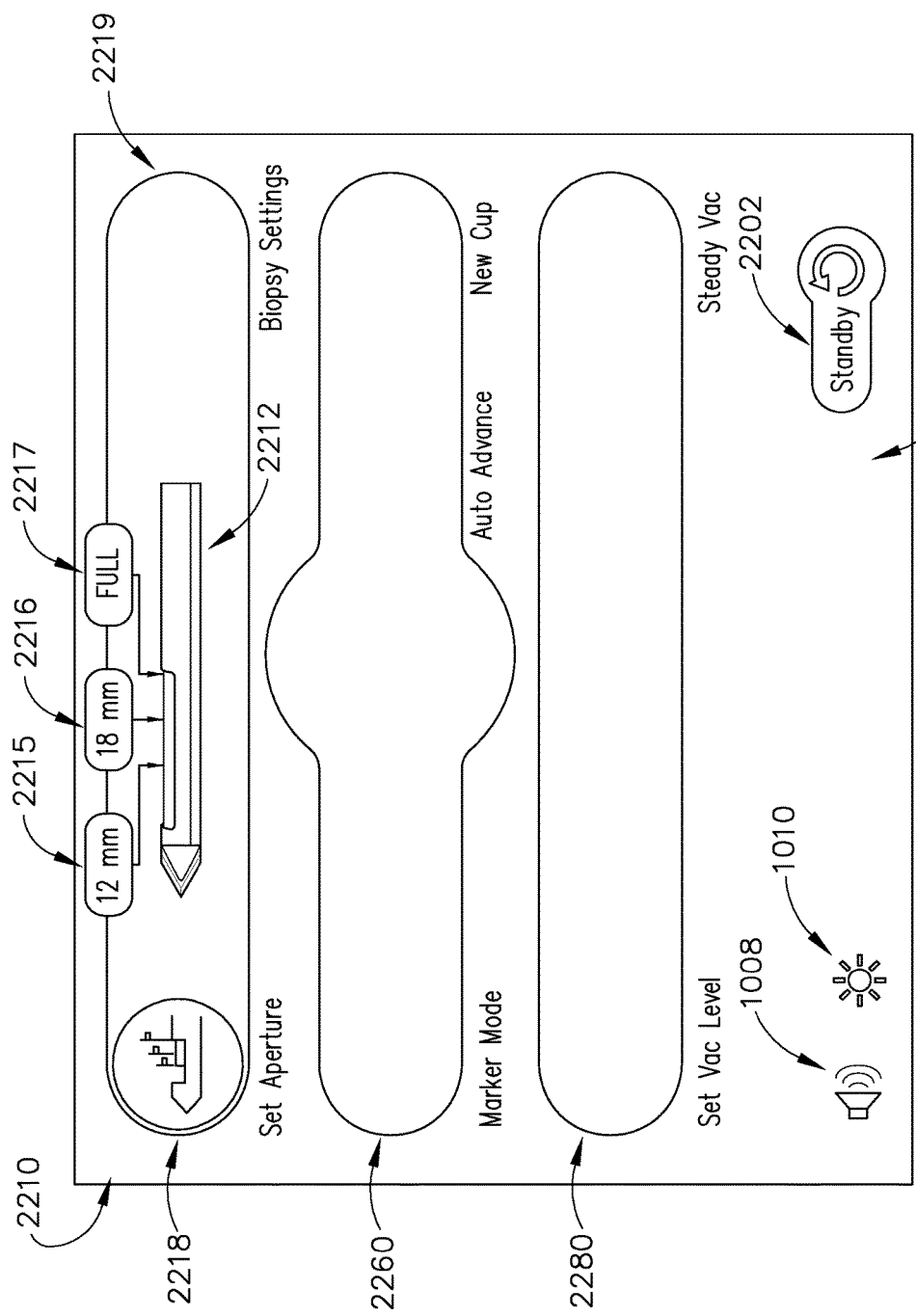
FIG. 49 depicts an exemplary twelfth user interface screen for the display on the vacuum control module of FIG. 1.

When the user taps on "set aperture" button (2218), touchscreen (410) transitions to screen (2208) shown in FIG. 49. Screen (2208) is generally similar to screen (2200), except that regions (2260, 2280) are dark, button (2219) is dark, and additional buttons (2215, 2216, 2217) appear over graphical representation (2212) of the distal end of needle (110). Buttons (2215, 2216, 2217) enable the user to set the proximal-most position for distal edge (152) of cutter (150) during operation of biopsy device (10). In particular, button (2215) establishes a proximal-most position for distal edge (152) of cutter (150) during operation of biopsy device (10) whereby lateral aperture (114) is only opened 12 mm by cutter (150) before cutter (150) advances distally. Button (2216) establishes a proximal-most position for distal edge (152) of cutter (150) during operation of biopsy device (10) whereby lateral aperture (114) is only opened 18 mm by cutter (150) before cutter (150) advances distally. Button (2217) establishes a proximal-most position for distal edge (152) of cutter (150) during operation of biopsy device (10) whereby lateral aperture (114) is fully opened by cutter (150) before cutter (150) advances distally. Of course, these increments are mere examples, and any other suitable increments may be used. In the present example, biopsy system (2) will default to a fully opened aperture (114) setting in the event that the user does not select a different aperture size through screen (2208).

When a user taps a particular button (2215, 2216, 2217), screen (2208) provides feedback by changing the position of the graphical representation (2214) of cutter (150) such that the distal end of graphical representation (2214) corresponds with the position just selected by the user. This positioning of graphical representation (2214) may persist until the positioning is later changed by the user. For instance, FIG. 49 shows graphical representation (2214) in the 18 mm position during use of biopsy device (10).

By way of example only, system (2) may provide the above-described "variable aperture" functionality in accordance with at least some of the teachings of U.S. Pat. No. 7,517,322, entitled "Biopsy Device with Variable Side Aperture," issued Apr. 14, 2009, the disclosure of which is incorporated by reference herein; and/or in accordance with at least some of the teachings of U.S. Pub. No. 2008/0214955, the disclosure of which is incorporated by reference herein. In some versions, the graphical representation (2214) of cutter (150) as described above is provided in a first color; while a second graphical representation of cutter (150) is provided in a second color. This second graphical representation may show the actual position of cutter in real time.

Figure 50:
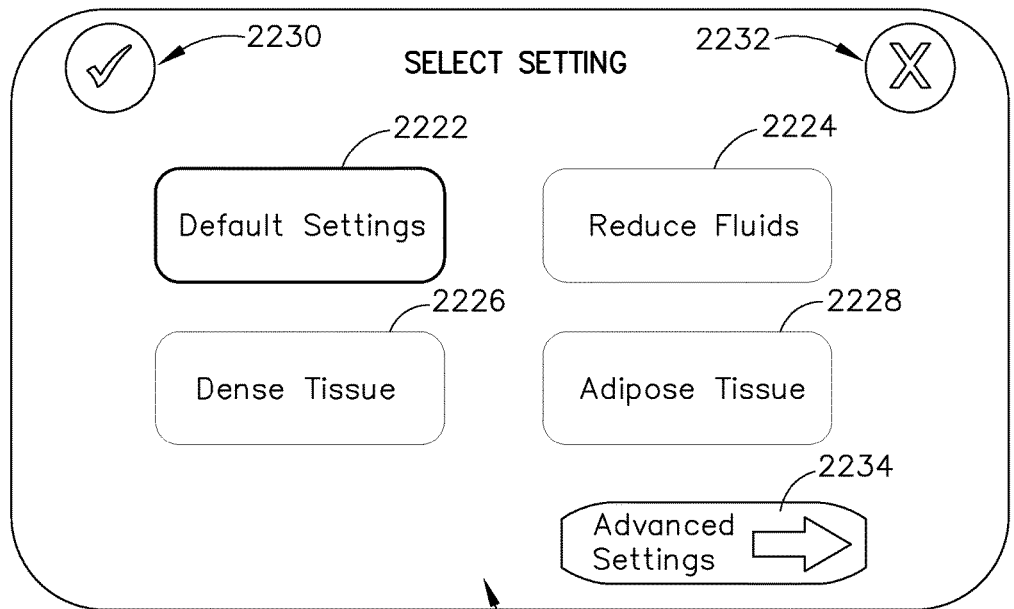
FIG. 50 depicts an exemplary thirteenth user interface screen for the display on the vacuum control module of FIG. 1.

Referring back to FIG. 48, when the user taps biopsy settings button (2219), touchscreen (410) transitions to screen (2220) shown in FIG. 50. Screen (2220) enables the user to select from four different pre-determined operational settings (2222, 2224, 2226, 2228) of biopsy system (2). Each pre-determined operational setting (2222, 2224, 2226, 2228) is substantially the same as pre-determined operational settings (1222, 1224, 1226, 1228) described above, such that the particular details of each pre-determined operational setting (2222, 2224, 2226, 2228) will not be repeated here. Once the user selects a given pre-determined operational setting (2222, 2224, 2226, 2228), the users selection is shown by darkening or changing the color of a given button (2222, 2224, 2226, 2228) for the selected setting. For instance, default settings button (2222) is shown as being selected in FIG. 50. Screen (2220) further includes a confirmation button (2230) and a cancelation button (2232). Upon tapping a given pre-determined operational setting (2222, 2224, 2226, 2228), the user may tap confirmation button (2230) to save the selection and return to sample screen (2200). Alternatively, the user may tap the cancelation button (2232) at any time to return to sample screen (2200) without saving a selected setting (2222, 2224, 2226, 2228) or without even making a selection.

Figure 51:
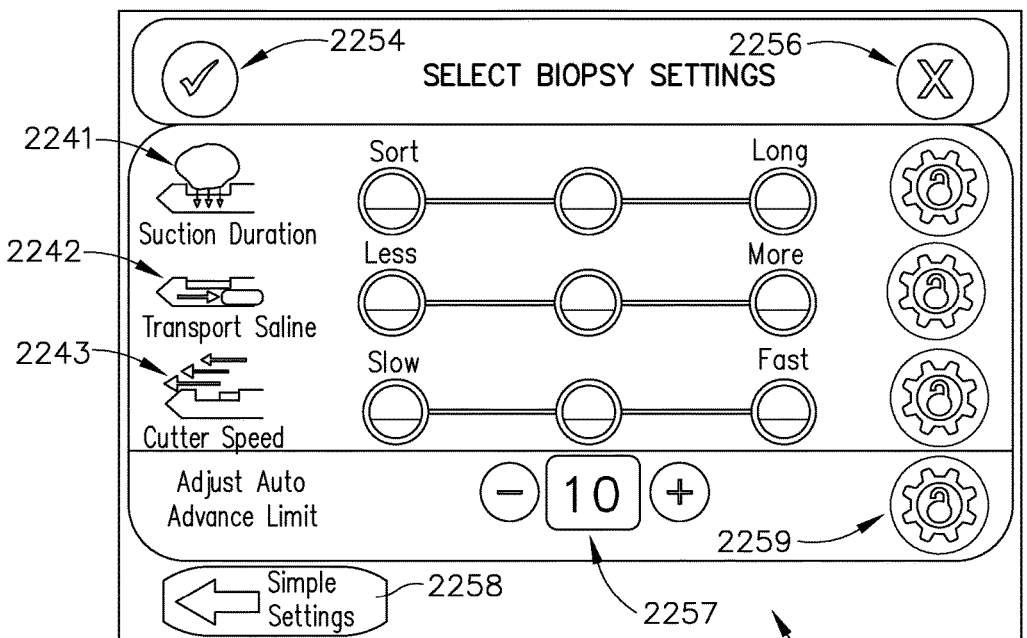
FIG. 51 depicts an exemplary fifteenth user interface screen for the display on the vacuum control module of FIG. 1.

If the user desires additional control over the biopsy system (2) settings, the user may tap an advanced settings button (2234). When the user taps advanced settings button (2234), touchscreen (410) transitions to screen (2240) as shown in FIG. 51. Screen (2240) is similar to screen (1240) described above. In particular, screen (2240) includes a vacuum duration adjustment region (2241), a transport saline adjustment region (2242), and a cutter speed adjustment region (2243). However, unlike screen (1240), screen (2240) further includes an auto advance limit adjustment feature (2257), which will be described in greater detail below.

Each region (2241, 2242, 2243) includes an adjustment slider (2244, 2245, 2246) and a lock setting button (2247, 2248, 2249). Adjustment sliders (2244, 2245, 2246) and lock setting buttons (2247, 2248, 2249) are substantially the same as adjustment slider (1244, 1245, 1246) and a lock setting button (1247, 1248, 1249), described above, such that detailed discussion of these features will not be repeated here. Additionally, each region (2241, 2242, 2243) also includes a graphical representation (2250, 2251, 2253) that is substantially similar to graphical representations (1250, 1251, 1253), described above, such that the details of graphical representations (2250, 2251, 2253) will not be repeated here.

As noted above, screen (2240) further includes auto advance limit adjustment feature (2257). The term "auto advance limit" refers to a feature used with tissue sample holder assembly (700) to collect multiple tissue samples. Generally, noted elsewhere herein, each tissue sample chamber (746) is configured to receive a multiple tissue samples. Accordingly, a given chamber (746) may remain indexed with cutter (150) for a predetermined number of tissue sample acquisition cycles. Once the predetermined number of tissue acquisition cycles is reached, the tissue sample holder assembly may be advanced to the next chamber (746). Thus, auto advance limit adjustment feature (2257) may be used to adjust the predetermined number of tissue acquisition cycles used to determine when tissue sample holder assembly will be advanced to index the next chamber (746) with cutter (150). A lock setting button (2259) may also be associated with auto advance limit adjustment feature (2257) to store the setting in memory for later procedures.

Of course, as with other features of vacuum control module (400) described herein, vacuum duration adjustment region (2241), transport saline adjustment region (2242), cutter speed adjustment region (2243) and auto advance limit adjustment feature (2257) may be omitted if desired. For instance, some versions may provide the various settings described above with only a single setting.

Screen (2220) further includes a confirmation button (2254) and a cancelation button (2256). Upon adjusting one or more settings using adjustment sliders (2244, 2245, 2246) and/or auto advance limit adjustment feature (2257), the user may tap confirmation button (2254) to save the selection and return to sample screen (2200). Alternatively, the user may tap the cancelation button (2256) at any time to return to sample screen (2200) without saving a selected setting any adjustments made using adjustment sliders (2244, 2245, 2246) and/or auto advance limit adjustment feature (2257). Should the user desire to return to screen (2208) to instead use pre-determined settings (2222, 2224, 2226, 2228) described above, the user may do so by tapping a simple settings button (2258), thereby causing touchscreen (410) to transition back to screen (1208) without saving any setting adjustments made via adjustment sliders (2244, 2245, 2246) and auto advance limit adjustment feature (2257).

It should be understood that the foregoing features relating to control of cutter (150) through touchscreen (410) are merely illustrative examples; and that they may be modified, substituted, supplemented, or omitted as desired. Various other features that may be used to provide control of cutter (150) through touchscreen (410) will be apparent to those of ordinary skill in the art in view of the teachings herein.

2. Exemplary Tissue Sample Holder Interface Features

Figure 52:
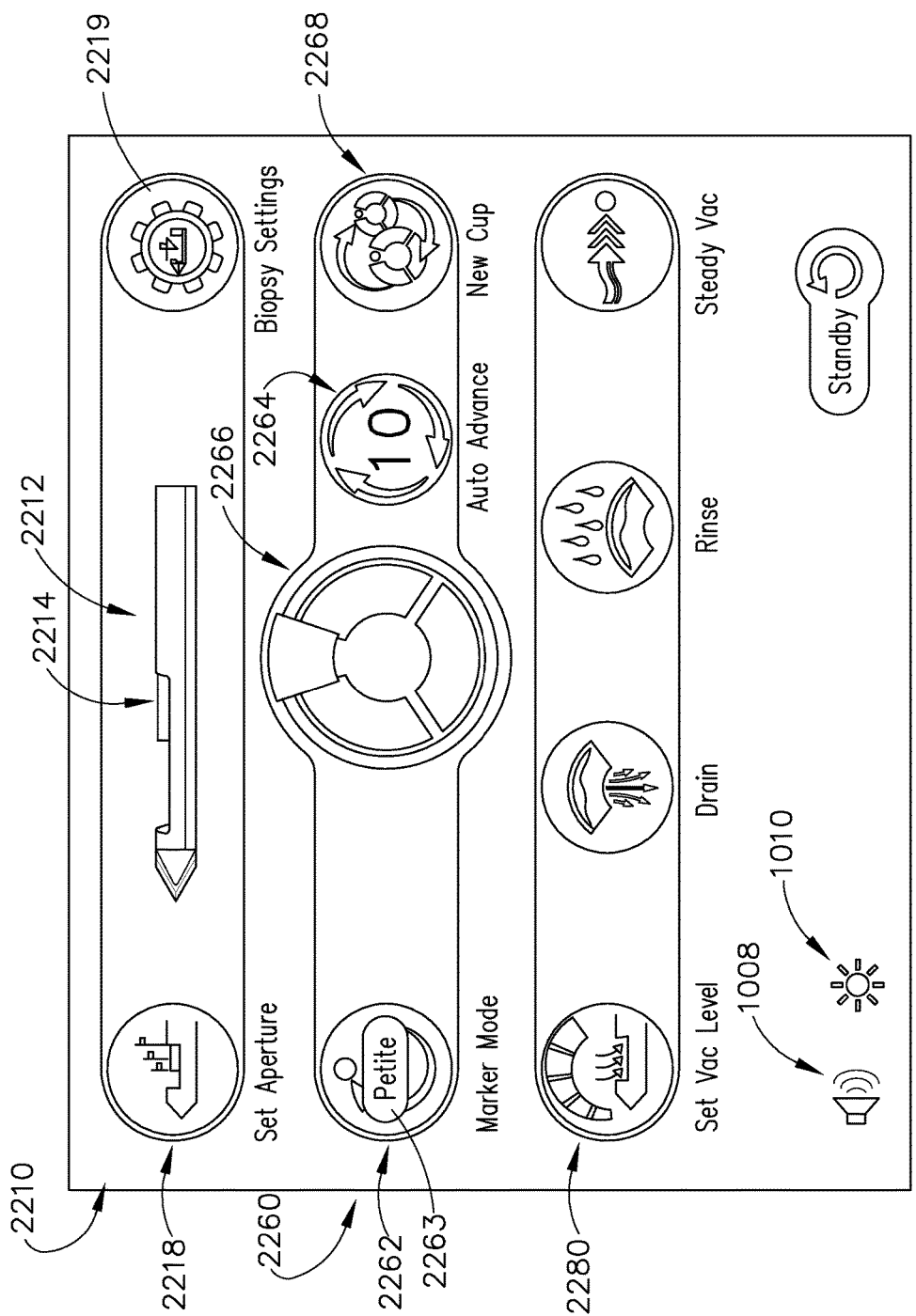
FIG. 52 depicts the eleventh user interface screen of FIG. 48 in a second state.

Returning to FIG. 48, tissue sample holder control region (2260) of screen (2200) includes "marker mode" button (2262), an "auto advance" button (2264), a graphical representation (2266) of tissue sample holder (300), and a "new cup" button (2268). "Marker mode" button (2262) may be tapped by the user to advance tissue sample holder assembly (700) such that passage (713) is aligned with cutter (150). When tissue sample holder assembly (700) is advanced to such a position, the user may insert a marker delivery device through passage (713) and cutter lumen (151) to deliver a marker to the biopsy site via needle (110). In some instances, cutter (150) may be set via the set aperture button (1218) to be positioned such that distal edge (152) of cutter (150) is located between the proximal and distal ends of lateral aperture (114), such that lateral aperture (114) is only partially opened. In such instances, certain markers may not be compatible with biopsy device (10) because of the reduced opening of lateral aperture (114). Accordingly, "marker mode" button (2262) may include "petite" indicator (2263) as shown in FIG. 52 to remind the user to either only use a petite marker or to adjust cutter (150) via set aperture button (2218) to fully open lateral aperture (114).

"Auto advance" button (2264) enables a user to select auto advance mode. As described above, auto advance mode permits a predetermined number of tissue samples to be collected in a single chamber (746) of tissue sample holder assembly (700) before tissue sample holder assembly (700) is indexed with the next chamber (746). Such a feature may be desirable for procedures requiring the removal of a bulk amount of tissue. When auto advance mode is inactive, tissue sample holder assembly (700) may advance incrementally, as described above with respect to tissue holder assembly (300). When "auto advance" button (2264) is pressed by the user, "auto advance" button (2264) is illuminated. Additionally, the particular number of tissue sample collection cycles to be performed prior to advancement may be displayed directly on "auto advance" button (2264). As described above, the particular number of tissue sample collection cycles may be adjusted by the user entering advanced biopsy settings via biopsy settings button (2219).

Once a particular chamber (746) has been filled to a desired level, or all chambers (746) have been filled to a desired level, the user may remove one or more tissue receiving trays (730) from tissue sample holder assembly (700). To reset graphical representation (2266), the user may tap "new cup" button (2268). Once graphical representation (2266) is reset, the user may begin taking additional tissue samples using the new tissue receiving trays (730).

It should be understood that the foregoing features relating to control of tissue sample holder (300) through touchscreen (410) are merely illustrative examples; and that they may be modified, substituted, supplemented, or omitted as desired. Various other features that may be used to provide control of tissues sample holder (300) through touchscreen (410) will be apparent to those of ordinary skill in the art in view of the teachings herein.

3. Exemplary Vacuum Interface Features

Still referring to FIG. 48, vacuum control region (2280) of screen (2200) includes a "set vac level" button (2282), a "drain" button (2284), a "rinse" button (2285), and a "steady vac" button (2286). Generally, "set vac level" button (2282) and "steady vac" button (2286) are substantially the same as "set vac level" button (1282) and "steady vac" button (1286) described above such that the particular details of "set vac level" button (2282) and "steady vac" button (2286) will not be repeated here.

However, unlike screen (1200), screen (2200) includes separate buttons (2284, 2285) for clean cup mode, as described above with respect to "clean cup" button (1284). In particular, a user may engage in clean cup mode by first tapping "drain" button (2284). Tapping "drain" button (2284) may clear chamber (746) of any excess fluid such as saline and/or bodily fluid. "Rinse" button (2285) may then be tapped to provide saline to chamber (746) of tissue sample holder assembly (700), thereby irrigating any tissue samples contained within chamber (746). The saline delivered to chamber (746) may then be removed by again tapping "drain" button (2284). Of course, the above procedure is merely exemplary, and in other examples buttons (2284, 2285) may be used in any sequence as desired, or not at all.

It should be understood that the foregoing features relating to control of vacuum through touchscreen (410) are merely illustrative examples; and that they may be modified, substituted, supplemented, or omitted as desired. Various other features that may be used to provide control of vacuum through touchscreen (410) will be apparent to those of ordinary skill in the art in view of the teachings herein. Similarly, various other features of system (2) that may be controlled through touchscreen (410), and ways in which such features may be controlled through touchscreen (410), will be apparent to those of ordinary skill in the art in view of the teachings herein.

4. Exemplary Standby Mode

Figure 53:
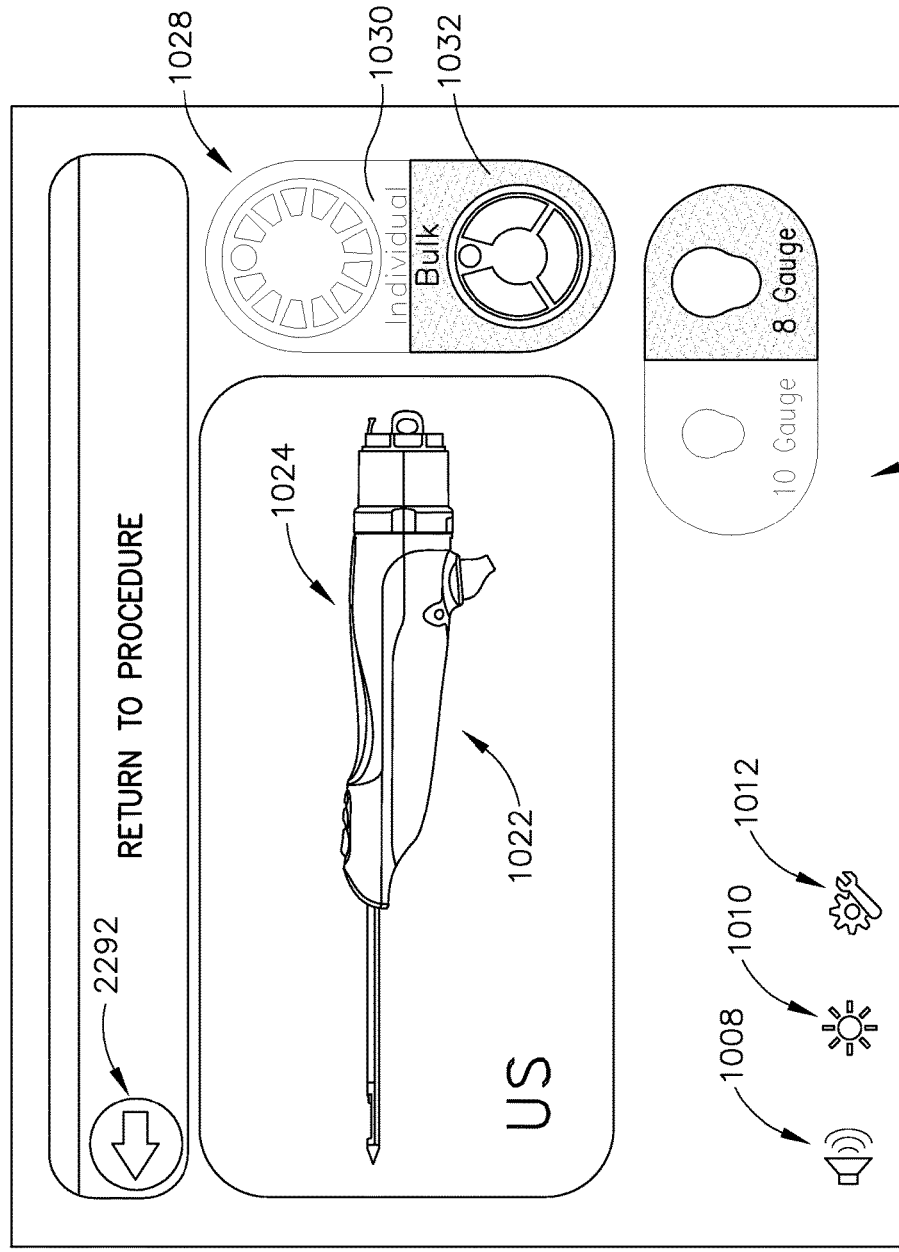
FIG. 53 depicts an exemplary sixteenth user interface screen for the display on the vacuum control module of FIG. 1.

As described above, sample screen (2200) includes a standby button (2202). Standby button (2202) may be tapped by the user to enter standby model. In particular, when standby button (2202) is tapped, touchscreen (410) transitions to screen (2290), thereby entering standby mode. As can be seen in FIG. 53, screen (2290) is substantially similar to screen (1080) described above, except screen (2290) includes a back button (2292) that permits the user to return to an active mode of biopsy system (2) where sample screen (2200) is displayed by touchscreen (410). It should be understood that other screens may also include standby button (2202); or that standby button (2202) may simply be omitted.

5. Exemplary Operation of Biopsy System in "Bulk" Mode

Figure 54:
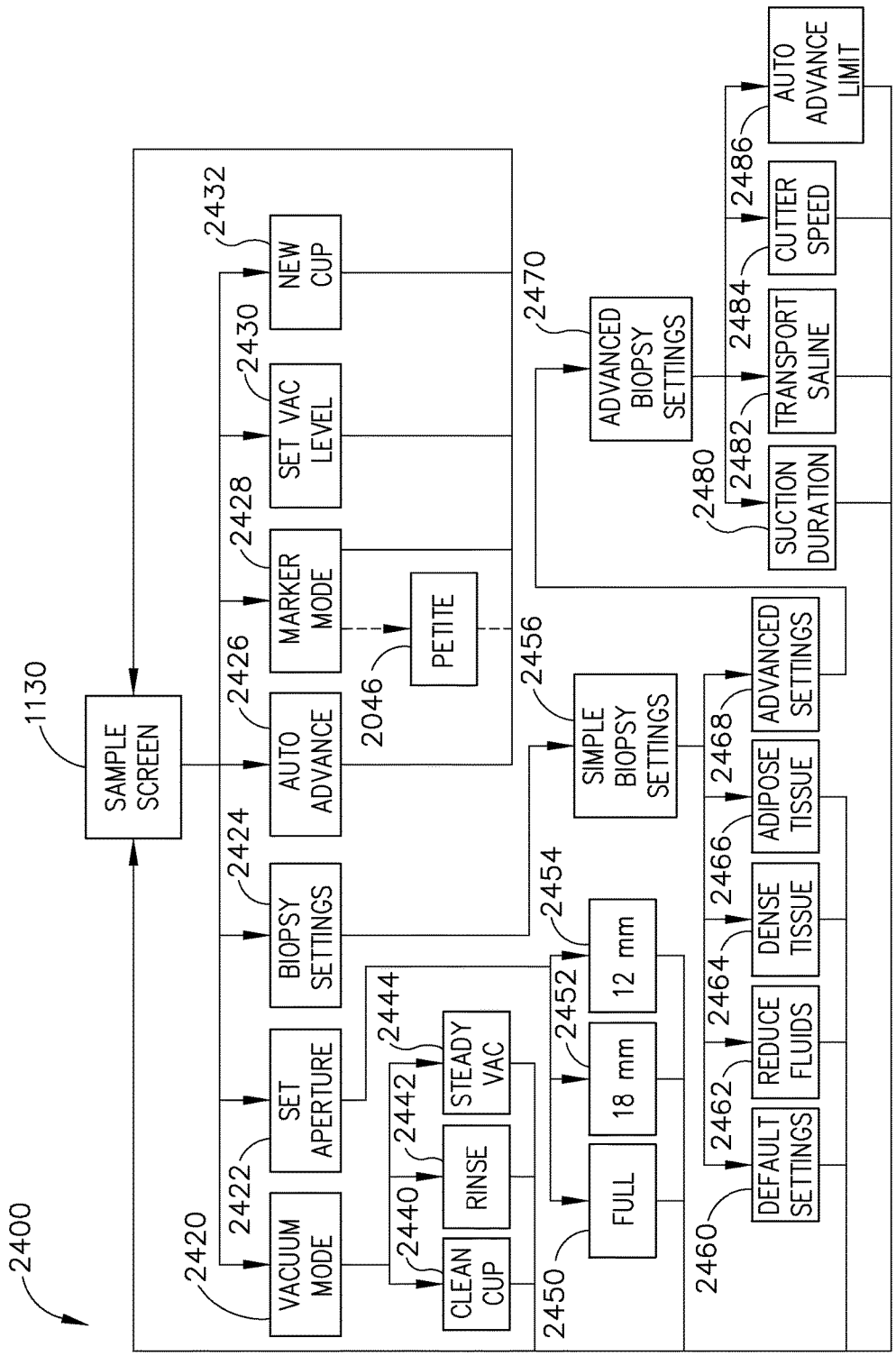
FIG. 54 depicts a flow chart showing an exemplary process for using the user interface screens of FIGS. 47-53.

FIG. 54 shows the operational states of control module (400), described above, in a flow chart (2400). It should be understood that flow chart (2400) is a continuation of flow chart (1100) shown in FIG. 35. In particular, flow chart (1100) ends with block (1130) when tissue sample holder assembly (700) is attached to probe (100). As described above, block (1130) corresponds to sample screen (2200), described above. Sample screen (2200) is similarly indicated by block (1130) in FIG. 54, with flow chart (2000) beginning at block (1130) in FIG. 54. As described above, screen (2200) provides several potential options for the user to proceed. For instance, the user may set the aperture defined by cutter (150) relative to lateral aperture (114) by tapping set aperture button (2218) as indicated by block (2422). In such instances, buttons (2215, 2216, 2217) may be used to select between a plurality of different aperture settings as indicated by blocks (2450, 2452, 2454). Once a given aperture size has been selected, a user may return to sample screen (2200) as indicated by block (1130).

The user may enter biopsy settings screen (2220) by pressing biopsy settings button (2219) as indicated by blocks (2424, 2456). Once touchscreen (410) has been transitioned to screen (2220) as indicated by block (2456), the user may select pre-determined settings (2222, 2224, 2226, 2228) as indicated by blocks (2460, 2462, 2464, 2466). Alternatively, the user may elect to enter screen (2240) to adjust advanced biopsy settings as indicated by block (2470). As described above, the user may selectively adjust vacuum duration, transport saline, and cutter speed using adjustment sliders (1244, 1245, 1246), and auto advance limit using auto advance limit adjustment feature (2257) as indicated by blocks (2480, 2482, 2484, 2486). Regardless of which screen (2220, 2240) is used by the user, the user may return to sample screen (2200) as indicated by block (1130) once any desired changes to the settings are made.

The user may initiate marker mode by pressing "marker mode" button (2262) as indicated by block (2428). Illumination of "petite" indicator (2263) is indicated by block (2446). Regardless of whether "petite" indicator (2263) is illuminated, sample screen (2200) remains displayed when biopsy device (2) is in marker mode, as described above.

From sample screen (2200) the user may also press "auto advance" button (2264) as indicated by block (2026). As can be seen, touchscreen (410) continues to display sample screen (2200) when "auto advance" button (2264) is pressed. However, as described above, "auto advance" button (2264) itself may become illuminated or highlighted to indicate activation of auto advance mode. Furthermore, once the user has completely filled a single chamber (746) or all chambers (746), one or more tissue receiving trays (730) may be removed from tissue sample holder assembly (700). Upon removal, the user may insert new trays (730) and press "new cup" button (2268) to reset graphical representation (2266) as indicated by block (2432).

The user may also set the level of vacuum of the biopsy system (2) from sample screen (2200) by pressing "set vac level" button (2282) as indicated by block (2430). As described above, when "set vac level" button (2282) is pressed, sample screen (2200) remains on touchscreen (410), yet various features are darkened or dimmed to highlight a set of bars (2288) that permit adjustment of the vacuum level. Once the desired level of vacuum has been set, the user can re-activate the rest of sample screen (2200) by pressing "set vac level" button (2282) again.

Block (2420) indicates that three vacuum modes may be activated from sample screen (2200). For instance, block (2440) indicates that "drain" button (2284) may be pressed to activate the procedure for providing vacuum to tissue sample holder assembly (700) described above. Block (2442) indicates that "rinse" button (2285) may be pressed to activate the procedure for providing saline to tissue sample holder assembly (700) described above. Block (2444) indicates that steady vac mode may be activated by pressing "steady vac" button (2286). Regardless of whether "drain" button (1284), "rinse" button (2285), or "steady vac" button (1286) is pressed, it should be understood that in both instances sample screen remains visible on touchscreen (410).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A biopsy system, comprising: (a) a probe set comprising a plurality of probes, wherein each probe of the probe set comprises: (i) a probe body, (ii) a needle, (iii) a cutter, and (iv) a tissue sample holder, wherein the tissue sample holder is in communication with the cutter to receive one or more tissue samples, (b) a holster, wherein the holster is selectively securable to each probe of the probe set; and (c) a user interface, wherein the user interface is in communication with the holster, wherein the user interface comprises a display, wherein the user interface is configured to identify which probe of the probe set is secured to the holster when a selected probe of the probe set is secured to the holster.

EXAMPLE 2

The biopsy system of Example 1, wherein the tissue sample holder of each probe of the probe set comprises a tissue sampling attribute.

EXAMPLE 3

The biopsy system of Example 2, wherein the tissue sampling attribute for at least one probe comprises an individual tissue collection configuration, wherein the tissue sampling attribute for at least one probe comprises a bulk tissue collection configuration.

EXAMPLE 4

The biopsy system of any one or more of Examples 2 and 3, wherein the user interface is configured to provide a plurality of graphical tissue sample holder representations, wherein each graphical tissue sample holder representation corresponds to the tissue sample holder of each probe of the probe set.

EXAMPLE 5

The biopsy system of Example 4, wherein the user interface is configured to identify a particular graphical tissue sample holder representation when a particular probe of the probe set is attached to the holster.

EXAMPLE 6

The biopsy system of Example 1, wherein the probe set comprises a first probe and a second probe, wherein the first probe comprises a first tissue sample holder, wherein the second probe comprises a second tissue sample holder.

EXAMPLE 7

The biopsy system of Example 6, wherein the first tissue sample holder has a first tissue collection attribute, wherein the second tissue sample holder has a second tissue collection attribute.

EXAMPLE 8

The biopsy system of Example 7, wherein the first tissue collection attribute corresponds to the first tissue sample holder being configured in an individual tissue collection configuration, wherein the second tissue collection attribute corresponds to the second tissue sample holder being configured in a bulk tissue collection configuration.

EXAMPLE 9

The biopsy system of Example 8, wherein the first tissue sample holder defines a plurality of individual tissue chambers, wherein each individual tissue chamber is configured to receive an individual tissue sample.

EXAMPLE 10

The biopsy system of Example 9, wherein the first tissue sample holder comprises twelve individual tissue chambers.

EXAMPLE 11

The biopsy system of Example 8, wherein the second tissue sample holder defines at least one bulk tissue sample chamber, wherein the at least one bulk tissue sample chamber is configured to receive a plurality of tissue samples.

EXAMPLE 12

The biopsy system of Example 11, wherein the second tissue sample holder comprises at least one discrete sample tray, wherein the sample tray is configured to be slidably disposed in a single bulk tissue chamber.

EXAMPLE 13

The biopsy system of Example 12, wherein the at least one sample tray comprises a floor and a pair of sidewalls extending from a base, wherein the floor and the pair of sidewalls define a tissue receiving chamber, wherein the tissue receiving chamber is configured to receive a plurality of tissue samples.

EXAMPLE 14

The biopsy system of Example 13, wherein each sidewall of the pair of sidewalls tapers upwardly as each sidewall extends distally from the base.

EXAMPLE 15

The biopsy device of Example 13, wherein each tray of the plurality of trays includes a plurality of vacuum openings, wherein the plurality of vacuum openings are configured to communicate vacuum therethrough.

EXAMPLE 16

A biopsy system, comprising: (a) a biopsy device, wherein the biopsy device comprises a needle extending from a body; (b) a control module, wherein the control module comprises a user interface, wherein the control module is in communication with the biopsy device; and (c) a tissue sample holder set, wherein the tissue sample holder set comprises: (i) a first tissue sample holder, wherein the first tissue sample holder comprises a plurality of tissue collection members, wherein the plurality of tissue collection members define a first tissue collection attribute; and (ii) a second tissue sample holder, wherein the second tissue sample holder comprises a plurality of tissue collection members, wherein the plurality of tissue collection members define a second tissue collection attribute, wherein the first tissue sample holder and the second tissue sample holder are selectably interchangeably associable with the biopsy device.

EXAMPLE 17

The tissue sample holder of Example 16, wherein the user interface of the control module is configured to indicate whether the first tissue sample holder or the second tissue sample holder is associated with the biopsy device.

EXAMPLE 18

The tissue sample holder of Example 16, wherein the user interface of the control module comprises a tissue sample holder indicator, wherein the tissue sample holder indicator is configured to selectably graphically depict each of the first tissue collection attribute and the second tissue collection attribute of the tissue sample holder set.

EXAMPLE 19

The tissue sample holder of Example 16, wherein the user interface of the control module comprises a first sample collection control and a second sample collection control, wherein the control module is configured to activate the first sample collection control in response to association of the first tissue sample holder with the biopsy device, wherein the control module is configured to activate the second sample collection control in response to association of the second tissue sample holder with the biopsy device.

EXAMPLE 20

A method for using a biopsy system to collect a plurality of tissue samples, wherein the biopsy system comprises a biopsy device, a control module and a tissue sample holder set, wherein the biopsy device comprises a needle extending from a body, and a cutter movably disposed relative to the needle to sever a plurality of tissue samples, wherein the control module comprises a user interface, and wherein the tissue sample holder set comprises a plurality of tissue sample holders interchangeably associated with the biopsy device, wherein the method comprises the steps of: (a) associating a selected tissue sample holder with the biopsy device, wherein the selected tissue sample holder has a tissue collection attribute; (b) identifying a single sampling mode indicator of a plurality of sample mode indicators associated with the user interface in response to associating the selected tissue sample holder with the biopsy device; (c) transporting a tissue sample through the cutter of the biopsy device into the selected tissue sample holder; (d) indexing the selected tissue sample holder relative to the biopsy device based on based on the tissue collection attribute of the selected tissue sample holder; and (e) repeating steps (c) and (d) until a predetermined number of tissue samples have been deposited in the selected tissue sample holder.

EXAMPLE 21

A biopsy device, comprising: (a) a body; (b) a needle; (c) a cutter; and (d) a tissue sample holder, wherein the tissue sample holder comprises: (i) an outer cup, (ii) an inner member, wherein the inner member defines a plurality of cavities, wherein the inner member is rotatable relative to the outer cup to index a single cavity of the plurality of cavities with the cutter, and (iii) a plurality of discrete sample trays, wherein each tray of the plurality of trays is configured to be slidably disposed in a separate cavity of the plurality of cavities, wherein each sample tray comprises a floor, and a pair of sidewalls extending distally from a base, wherein the floor and the pair of sidewalls define a tissue receiving chamber, wherein the tissue receiving chamber is configured to receive a plurality of tissue samples.

EXAMPLE 22

The biopsy device of claim 21, wherein the floor of each sample tray slopes upwardly as the floor extends distally from the base.

EXAMPLE 23

The biopsy device of Example 22, wherein each sidewall of the pair of sidewalls tapers upwardly as each sidewall extends distally from the base.

EXAMPLE 24

The biopsy device of Example 21, wherein each tray of the plurality of trays includes a plurality of vacuum openings, wherein the plurality of vacuum openings are configured to communicate vacuum therethrough.

EXAMPLE 25

The biopsy device of Example 24, wherein the plurality of vacuum openings are disposed on the floor of each sample tray.

EXAMPLE 26

The biopsy device of Example 25, wherein the plurality of vacuum openings are further disposed on each sidewall of the plurality of sidewalls.

EXAMPLE 27

The biopsy device of Example 21, wherein the floor of each sample tray comprises an arcuate lateral cross-sectional shape.

EXAMPLE 28

The biopsy device of Example 21, wherein each sample tray of the plurality of sample trays further comprises a distal wall and a proximal wall, wherein the distal wall is disposed at a distal end of the floor and the pair of sidewalls, wherein the proximal wall is associated with the base, wherein the floor and the pair of sidewalls extend distally from the proximal wall.

EXAMPLE 29

The biopsy device of Example 28, wherein the distal wall includes a first opening and a second opening, wherein the first opening is configured to receive a tissue sample therethrough, wherein the second opening is configured to receive vacuum therethrough.

EXAMPLE 30

The biopsy device of Example 28, wherein the proximal wall is disposed adjacently to a base wall.

EXAMPLE 31

The biopsy device of Example 30, wherein one or more of the proximal wall and the base wall are configured to sealingly engage an inner wall defining the plurality of cavities of the inner member.

EXAMPLE 32

The biopsy device of Example 30, wherein a grip extends proximally from the base wall.

EXAMPLE 33

The biopsy device of Example 21, wherein the floor of each sample tray is configured to partially define a vacuum cavity when each sample tray is disposed in a respective cavity of the inner member.

EXAMPLE 34

The biopsy device of Example 33, wherein the vacuum cavity is in communication with a vacuum source, wherein the floor is configured to communicate vacuum between the tissue receiving chamber and the vacuum cavity.

EXAMPLE 35

The biopsy device of Example 21, wherein each sidewall of the pair of sidewalls is disposed at an obtuse angle relative to the floor.

EXAMPLE 36

A tissue sample holder, wherein the tissue sample holder is configured for use in connection with a biopsy device, wherein the biopsy device comprises a needle extending from a body, and a cutter movably disposed relative to the needle to sever a plurality of tissue samples, the tissue sample holder comprising: (a) a cup; (b) a rotatable member, wherein the rotatable member defines a plurality of tissue cavities, and an instrument port; (c) a plurality of tissue collection members, wherein each tissue collection member comprises: (i) a base, (ii) a floor extending distally from the base, (iii) a pair of sidewalls extending distally from the base, and (iv) a distal wall, wherein the floor, the pair of sidewalls, and the distal wall collectively define a tissue collection chamber, wherein the tissue collection chamber is configured to receive a plurality of tissue samples, wherein each tissue collection member is configured to be removably secured in a respective cavity of the rotatable member.

EXAMPLE 37

The tissue sample holder of Example 36, further comprising a plug, wherein the plug is configured to be removably disposed in the instrument port of the rotatable member.

EXAMPLE 38

The tissue sample holder of Example 36, wherein the rotatable member is configured to rotate relative to the cup to index a single tissue cavity or the instrument port with the cutter of the biopsy device.

EXAMPLE 39

The tissue sample holder of Example 38, wherein the rotatable member is configured to be manually rotatable relative to the cup.

EXAMPLE 40

A method for using a tissue sample holder to collect a plurality of tissue samples from a biopsy device, wherein the biopsy device comprises a needle extending from a body, and a cutter movably disposed relative to the needle to sever a plurality of tissue samples, wherein the tissue sample holder comprises: (a) a cup; (b) a rotatable member, wherein the rotatable member defines a plurality of tissue cavities, and an instrument port; (c) a plurality of tissue collection members, wherein each tissue collection member comprises: (i) a base, (ii) a floor extending distally from the base, (iii) a pair of sidewalls extending distally from the base, and (iv) a distal wall, wherein the method comprises the steps of: (a) rotating the rotatable member relative to the cup to index a first tissue cavity of the plurality of tissue cavities with the cutter of the biopsy device; (b) transporting a tissue sample through the cutter of the biopsy device into the first tissue cavity of the rotatable member, and depositing the tissue sample in a corresponding first tissue collection member; (c) repeating step (b) until a predetermined number of tissue samples have been deposited in the first tissue collection member, (d) rotating the rotatable member relative to the cup to index a second tissue cavity of the plurality of tissue cavities with the cutter of the biopsy device; (e) transporting a tissue sample through the cutter of the biopsy device into the second tissue cavity of the rotatable member, and depositing the tissue sample in a corresponding second tissue collection member; and (f) repeating step (e) until the predetermined number of tissue samples have been deposited in the second tissue collection member.

EXAMPLE 41

The biopsy system of Example 1, wherein the display of the user interface comprises a probe set selection interface and one or more sampling interfaces.

EXAMPLE 42

The biopsy system of Example 41, wherein the probe selection interface is configured to receive a plurality of probe selection inputs, wherein each probe selection inputs corresponds to each probe of the probe set.

EXAMPLE 43

The biopsy system of Example 41, wherein the one or more sampling interfaces comprises a needle control, a tissue sample holder display, and a sample mode selector, wherein the sample mode selector is configured to manipulate a plurality of tissue sample collection attributes.

EXAMPLE 44

The biopsy system of Example 43, wherein the sample mode selector comprises a set vacuum level selector, a clean cup selector, and a steady vacuum selector.

EXAMPLE 45

The biopsy system of Example 44, wherein the set vacuum level selector is configured to transition a level of vacuum supplied to the probe between a plurality of predetermined vacuum levels.

EXAMPLE 46

The biopsy system of Example 44, wherein the clean cup selector is configured to initiate a clean cup mode, wherein the clean cup mode is configured to supply saline to the tissue sample holder of the probe.

EXAMPLE 47

The biopsy system of Example 44, wherein the steady vacuum selector is configured to initiate a steady vacuum mode, wherein the steady vacuum mode is configured to correspond to a steady flow of vacuum through the needle of a particular probe of the probe set.

VI. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system, comprising:
   (a) a probe set comprising a plurality of probes, wherein each probe of the probe set comprises:
      (i) a probe body,
      (ii) a needle,
      (iii) a cutter, and
      (iv) a tissue sample holder, wherein the tissue sample holder is in communication with the cutter to receive one or more tissue samples;
   (b) a holster, wherein the holster is selectively securable to each probe of the probe set; and
   (c) a user interface, wherein the user interface is in communication with the holster, wherein the user interface includes a display, wherein the user interface is configured to identify which probe of the probe set is secured to the holster when a selected probe of the probe set is secured to the holster.

2. The biopsy system of claim 1, wherein the tissue sample holder of each probe of the probe set includes a tissue sampling attribute.

3. The biopsy system of claim 2, wherein the tissue sampling attribute for at least one probe includes an individual tissue collection configuration, wherein the tissue sampling attribute for at least one probe includes a bulk tissue collection configuration.

4. The biopsy system of claim 2, wherein the user interface is configured to provide a plurality of graphical tissue sample holder representations, wherein each graphical tissue sample holder representation corresponds to the tissue sample holder of each probe of the probe set.

5. The biopsy system of claim 4, wherein the user interface is configured to identify a particular graphical tissue sample holder representation when a particular probe of the probe set is attached to the holster.

6. The biopsy system of claim 1, wherein the probe set includes a first probe and a second probe, wherein the first probe includes a first tissue sample holder, wherein the second probe includes a second tissue sample holder.

7. The biopsy system of claim 6, wherein the first tissue sample holder has a first tissue collection attribute, wherein the second tissue sample holder has a second tissue collection attribute.

8. The biopsy system of claim 7, wherein the first tissue collection attribute corresponds to the first tissue sample holder being configured in an individual tissue collection configuration, wherein the second tissue collection attribute corresponds to the second tissue sample holder being configured in a bulk tissue collection configuration.

9. The biopsy system of claim 8, wherein the first tissue sample holder defines a plurality of individual tissue chambers, wherein each individual tissue chamber is configured to receive an individual tissue sample.

10. The biopsy system of claim 9, wherein the first tissue sample holder defines twelve individual tissue chambers.

11. The biopsy system of claim 8, wherein the second tissue sample holder defines at least one bulk tissue sample chamber, wherein the at least one bulk tissue sample chamber is configured to receive a plurality of tissue samples.

12. The biopsy system of claim 11, wherein the second tissue sample holder includes at least one discrete sample tray, wherein the sample tray is configured to be slidably disposed in a single bulk tissue chamber.

13. The biopsy system of claim 1, wherein the display of the user interface includes a probe set selection interface and one or more sampling interfaces.

14. The biopsy system of claim 13, wherein the probe selection interface is configured to receive a plurality of probe selection inputs, wherein each probe selection input corresponds to each probe of the probe set.

15. The biopsy system of claim 13, wherein the one or more sampling interfaces comprises a needle control, a tissue sample holder display, and a sample mode selector, wherein the sample mode selector is configured to manipulate a plurality of tissue sample collection attributes.

* * * * *